United States Patent
Kobayashi et al.

(10) Patent No.: US 7,423,185 B2
(45) Date of Patent: Sep. 9, 2008

(54) AMINO ALCOHOL DERIVATIVES, PHARMACEUTICAL COMPOSITIONS CONTAINING THE SAME, AND USE THEREOF

(75) Inventors: Junichi Kobayashi, Hotaka-machi (JP); Tetsuya Nakamura, Matsumoto (JP); Ritsu Suzuki, Toyoshina-machi (JP); Hideyuki Muranaka, Toyoshina-machi (JP); Tomonaga Ozawa, Matsumoto (JP); Yuichiro Kai, Toyoshina-machi (JP); Takehiro Ishikawa, Toyoshina-machi (JP); Tatsuhiro Kondo, Matsumoto (JP); Tetsuro Tamai, Misato-mura (JP); Satoshi Akahane, Mtsumoto (JP)

(73) Assignee: Kissei Pharmaceutical Co., Ltd., Nagano (JP)

( * ) Notice: Subject to any disclaimer, the term of this patent is extended or adjusted under 35 U.S.C. 154(b) by 120 days.

(21) Appl. No.: 10/545,380

(22) PCT Filed: Jan. 30, 2004

(86) PCT No.: PCT/JP2004/000893

§ 371 (c)(1), (2), (4) Date: Aug. 12, 2005

(87) PCT Pub. No.: WO2004/072016

PCT Pub. Date: Aug. 26, 2004

(65) Prior Publication Data

US 2006/0128807 A1 Jun. 15, 2006

(30) Foreign Application Priority Data

Feb. 14, 2003 (JP) ............... 2003-035847
Feb. 20, 2003 (JP) ............... 2003-041931

(51) Int. Cl.
- C07C 217/14 (2006.01)
- C07C 217/20 (2006.01)
- C07D 307/79 (2006.01)
- A61K 31/195 (2006.01)
- A61P 1/00 (2006.01)
- A61P 1/16 (2006.01)
- A61P 3/04 (2006.01)

(52) U.S. Cl. ............. 568/585; 568/586; 514/646

(58) Field of Classification Search ............ None
See application file for complete search history.

(56) References Cited

U.S. PATENT DOCUMENTS

| | | |
|---|---|---|
| 6,037,362 A | 3/2000 | Miyoshi et al. |
| 2003/0212063 A1 | 11/2003 | Lafontaine et al. |
| 2005/0137236 A1 | 6/2005 | Hattori et al. |

FOREIGN PATENT DOCUMENTS

| | | |
|---|---|---|
| DE | 4130918 A1 | 3/1993 |
| EP | 882707 A1 | 12/1998 |
| WO | WO 99/65877 A1 | 12/1999 |
| WO | WO 02/094770 A2 | 11/2002 |
| WO | WO 2005/061433 A2 | 7/2005 |

OTHER PUBLICATIONS

Bristol, Annual Reports in Medicinal Chemistry. 1998, vol. 33, pp. 193-202.*
Arbeeny, Obesity Research, 2004, vol. 12, No. 8, pp. 1191-1196.*

* cited by examiner

*Primary Examiner*—Yvonne Eyler
*Assistant Examiner*—Yevgeny Valenrod
(74) *Attorney, Agent, or Firm*—Sughrue Mion, PLLC

(57) ABSTRACT

The present invention provides compounds represented by general formula (I):

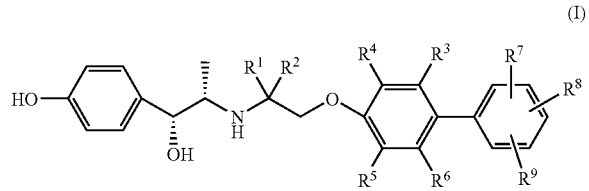

(I)

or pharmaceutical acceptable salts thereof, wherein $R^1$ and $R^2$ are each hydrogen or lower alkyl; $R^3$, $R^4$, $R^5$ and $R^6$ are each hydrogen, halogen, lower alkyl or lower alkoxy; $R^7$ and $R^8$ are each hydrogen, halogen, lower alkyl, halo-lower alkyl, lower alkoxy, cycloalkyl, aryl, heteroaryl, cyano, a hydroxyl group, lower acyl, carboxy or the like; $R^9$ is —C(O)—$R^{10}$, -$A^1$-C(O)—$R^{10}$, —O-$A^2$-C(O)—$R^{10}$ or a tetrazol-5-yl group, which exhibit potent and selective β3-adrenoceptor stimulating activities. The present invention also provides pharmaceutical compositions containing said compound, and uses thereof.

18 Claims, No Drawings

AMINO ALCOHOL DERIVATIVES, PHARMACEUTICAL COMPOSITIONS CONTAINING THE SAME, AND USE THEREOF

TECHNICAL FIELD

The present invention relates to novel amino alcohol derivatives, which exhibit β3-adrenoceptor stimulating activities, pharmaceutical compositions containing the same, and their uses.

BACKGROUND ART

Sympathetic β-adrenoceptors have been classified into β1-, β2- and β3-subtypes. The β-adrenoceptors are each distributed in specific tissues and have different functions.

β1-adrenoceptors are located predominantly on heart, and stimulation of β1-adrenoceptors invokes increases in heart rate and potentiation of cadiac contractility. β2-adrenoceptors are found abundantly on smooth muscles of blood vessels, bronchi and uterus, and stimulation of β2-adrenoceptors leads to vasodilation, bronchodilation and inhibition of uterine contraction. A variety of β1- and β2-adrenoceptor stimulants have been developed so far and utilized as cardiotonics, bronchodilators, prophylactic agents for threatened, abortion or premature labor and the like.

It has been reported that β3-adrenoceptors are located in adipocytes, brain, gall bladder, prostate, urinary bladder, intestinal tract and the like (see nonpatent literatures 1, 2, 3 and 4), and stimulation of β3-adrenoceptors promotes lipolysis, increased thermogenesis, hypoglycemic activities; hypolipidemic activities such as triglyceride lowering activities, hypocholesterolemic activities, HDL-cholesterol increasing activities and the like; antidepressive activities; gall bladder relaxing activities; suppression of intestinal motilities and the like (see nonpatent literatures 2, 5, 6 and 7). Accordingly, β3-adrenoceptor agonists are expected to be useful for treating or preventing obesity, diabetes mellitus, hyperlipidemia, depression, urinary dysfunctions, diseases caused by biliary tract hypermotility, or diseases caused by intestinal hypermotility.

Recent studies on β3-adrenoceptor agonists have been focused mainly on developing an anti-obesity or anti-diabetic agent. However, many of such β3-adrenoceptor agonists have been accompanied with adverse reactions such as increased heart rate, muscle tremors, hypokalemia and the like, which are resulted from simulation of β1- and/or β2-adrenoceptor. It has also been reported that activities of β3-adrenoceptor agonist differ markedly among species, and some compounds exhibit less potent stimulating activities on human β3-adrenoceptors than on rodent such as rat β3-adrenoceptors (see nonpatent literature 8). Accordingly, it has been greatly desired for novel agents exhibiting potent stimulating activities on human β3-adrenoceptors with less adverse reactions caused by stimulation of β1- and β2-adrenoceptors.

Donaldson K. H. et al disclose compounds represented by the following general formula:

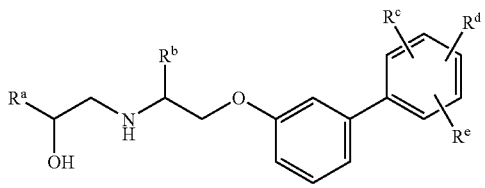

wherein $R^a$ is a phenyl group optionally substituted with one or more substituents selected from the group consisting of halogen, hydroxyl, $C_{1-6}$ alkoxy, $C_{1-6}$ alkyl, nitro, cyano, hydroxymethyl, trifluoromethyl, —$NR^fR^f$ and —$NHSO_2R^f$ in which $R^f$ is hydrogen or $C_{1-4}$ alkyl; $R^b$ is hydrogen or $C_{1-6}$ alkyl; $R^c$ is cyano, tetrazol-5-yl or —$CO_2R^g$ in which $R^g$ is hydrogen or $C_{1-6}$ alkyl; $R^d$ and $R^e$ are independently hydrogen, $C_{1-6}$ alkyl, —$CO_2H$, —$CO_2C_{1-6}$ alkyl, cyano, tetrazol-5-yl, halogen, trifluoromethyl or $C_{1-6}$ alkoxy (see patent literature 1). However, these compounds have unsatisfactory stimulating activities and selectivity on β3-adrenoceptors.

Nonpatent Literature:
1. Berkowitz D E. et al, "Eur. J. Pharmacol.", 1995, vol. 289, p. 223-228;
2. Howe R., "Drugs of the Future", 1993, vol. 18(6), p. 529-549;
3. Ponti F D. et al, "Pharmacology", 1995, vol. 51, p. 288-297;
4. Rodriguez M. et al, "Brain res. Mol. Brain res." 1995, vol. 29(2), p. 369-375;
5. Simiand J. et al, "Eur. J. Pharm.", 1992, vol. 219, p. 193-201;
6. Igawa Y. et al, "The Japanese Journal of Urology", 1997, vol. 88(2), p. 183;
7. Igawa Y. et al, "Neurourol. Urodyn.", 1997, vol. 16(5), p. 363-365;
8. Furutani Y., "Endocrinology & Diabetology", 2001, vol. 12(4), p. 416-422

Patent Literature:
1. International Publication No. WO99/65877 pamphlet

DISCLOSURE OF THE INVENTION

The present inventors have intensively investigated a novel compound having potent stimulating activities on human β3-adrenoceptors, and more preferably a compound with less potent stimulating activities on β1- and/or β2-adrenoceptors than on β3-adrenoceptors, and found surprisingly that amino alcohol derivatives represented by general formula (I) exhibit potent stimulating activities on human β3-adrenoceptors than on β1- and/or β2-adrenoceptors. Based on these findings, the present invention has been accomplished.

The present invention therefore provides a compound represented by general formula (I):

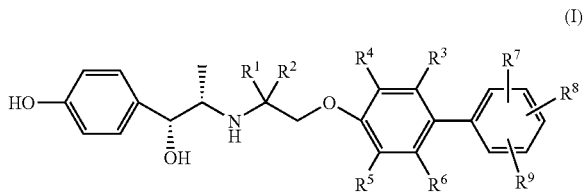

(I)

a prodrug thereof, or a pharmaceutically acceptable salt thereof, wherein each of $R^1$ and $R^2$ is independently a hydrogen atom or a lower alkyl group;

each of $R^3$, $R^4$, $R^5$ and $R^6$ is independently a hydrogen atom, a halogen atom, a lower alkyl group or a lower alkoxy group;

each of $R^7$ and $R^8$ is independently a hydrogen atom, a halogen atom, a lower alkyl group, a halo-lower alkyl group, a hydroxy-lower alkyl group, a cycloalkyl group, a heterocycloalkyl group, a lower alkoxy group, a di(lower alkyl)amino group, a cyclic amino group, a di(lower alkyl) amino-lower alkyl group, an aryl group, an aryloxy group, an aralkyloxy group, a heteroaryl group, a cyano group, a hydroxyl group, a lower acyl group, a lower alkylsulfanyl group, a lower alkylsulfonyl group, a carboxy group, a lower alkoxycarbonyl group or an aralkyloxycarbonyl group, or when $R^7$ and $R^8$ are adjacent each other, R7 and R8 are bonded together to form —O—$(CH_2)_m$—O—, —O—$(CH_2)_n$— or —$(CH_2)_p$—, wherein m is an integer of 1 to 3, n is an integer of 2 to 4, p is an integer of 3 to 5;

$R^9$ is —C(O)—$R^{10}$, -$A^1$-C(O)—$R^{10}$, —O-$A^2$-C(O)—$R^{10}$ or a tetrazol-5-yl group, wherein $R^{10}$ is a hydroxyl group, a lower alkoxy group, an aralkyloxy group or —$NR^{11}R^{12}$, each of $R^{11}$ and $R^{12}$ is independently a hydrogen atom, a lower alkyl group, a carboxy-lower alkyl group or a lower alkoxycarbonyl-lower alkyl group, or $R^{11}$ and $R^{12}$, together with the nitrogen atom to which they are bonded, form a cyclic amine, $A^1$ is a lower alkylene group or a lower alkenylene group, and $A^2$ is a lower alkylene group.

The present invention also provides a compound represented by general formula (I) as above defined, or a pharmaceutically acceptable salt thereof, wherein $R^1$ and $R^2$ are a hydrogen atom;

each of $R^7$ and $R^8$ is independently a hydrogen atom, a halogen atom, a lower alkyl group, a halo-lower alkyl group, a cycloalkyl group, a lower alkoxy group, an aryloxy group, a lower alkylsulfonyl group, a hydroxyl group or a lower acyl group;

$R^9$ is —C(O)-$R^{10}$ or —$OCH_2C(O)$—$R^{10}$; and $R^{10}$ is a hydroxyl group, a lower alkoxy group or an aralkyloxy group; provided that at least one of $R^3$, $R^4$, $R^5$ and $R^6$ is a halogen atom, a lower alkyl group or a lower alkoxy group.

The present invention also provides a compound represented by general formula (I) as above defined, or a pharmaceutically acceptable salt thereof, wherein $R^1$, $R^2$, $R^3$, $R^4$, $R^5$ and $R^6$ are a hydrogen atom, each of $R^7$ and $R^8$ is independently a hydrogen atom, a halogen atom, a lower alkyl group, a halo-lower alkyl group, a cycloalkyl group, a lower alkoxy group or an aryloxy group;

$R^9$ is —C(O)—$R^{10}$ or —$OCH_2C(O)$—$R^{10}$; and $R^{10}$ is a hydroxyl group, a lower alkoxy group or an aralkyloxy group.

In another aspect, the present invention provides a pharmaceutical composition which comprises, as an active ingredient, a compound represented by general formula (I) or a pharmaceutically acceptable salt thereof.

In still another aspect, the present invention provides a therapeutic or prophylactic agent for obesity, diabetes mellitus, hyperlipidemia, depression, urinary dysfunctions, diseases caused by biliary calculus or biliary tract hypermotility, or diseases caused by intestinal hypermotility, which comprises a compound represented by general formula (I) or a pharmaceutically acceptable salt thereof.

In still another aspect, the present invention provides a pharmaceutical combination comprising a compound represented by general formula (I) or a pharmaceutically acceptable salt thereof and at least one selected from the group consisting of an antiobesity agent, an antidiabetic agent, a hypolipidemic agent and a therapeutic agent for urinary dysfunctions other than a β3-adrenoceptor agonist.

In still another aspect, the present invention provides a use of a compound represented by general formula (I) or a pharmaceutically acceptable salt thereof for the manufacture of a medicament for treating or preventing obesity, diabetes mellitus, hyperlipidemia, depression, urinary dysfunctions, diseases caused by biliary calculus or biliary tract hypermotility, or diseases caused by intestinal hypermotility.

In still another aspect, the present invention provides a method for treating or preventing obesity, diabetes mellitus, hyperlipidemia, depression, urinary dysfunctions, diseases caused by biliary calculus or biliary tract hypermotility, or diseases caused by intestinal hypermotility, which comprises administering an effective amount of a compound represented by general formula (I) or a pharmaceutically acceptable salt thereof.

The invention is described using the terms defined below unless otherwise specified.

The term "halogen atom" refers to a fluorine, chlorine, bromine or iodine atom, preferably a fluorine or chlorine atom.

The term "lower alkyl group" refers to a straight chained or branched alkyl group having 1 to 6 carbon atoms such as a methyl, ethyl, propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, hexyl, isohexyl group and the like. Preferred lower alkyl groups for $R^1$, $R^2$, $R^3$, $R^4$, $R^5$ and $R^6$ are a $C_{1-4}$ alkyl group, more preferably a methyl group. Preferred lower alkyl groups for $R^7$, $R^8$ and $R^9$ are a $C_{1-4}$ alkyl group, more preferably a methyl, ethyl, propyl or isopropyl group.

The term "halo-lower alkyl group" refers to a lower alkyl group substituted with the same or different 1 to 3 halogen atoms such as a trifluoromethyl, 2-chloroethyl, 2-fluoroethyl, 2,2,2-trifluoroethyl, 2,2,2-trichloroethyl group and the like, preferably a trifluoromethyl group.

The term "hydroxy-lower alkyl group" refers to a lower alkyl group substituted with a hydroxyl group such as a hydroxymethyl, 2-hydroxyethyl, 1-hydroxyethyl, 3-hydroxypropyl, 4-hydroxybutyl group and the like, preferably a hydroxylmethyl group.

The term "cycloalkyl group" refers to a saturated cyclic hydrocarbon group having 3 to 7 carbon atoms such as a cyclopropyl, cyclobutyl, cyclopentyl, cyclohexyl, cycloheptyl group and the like, preferably a cyclopentyl or cyclohexyl group.

The term "heterocycloalkyl group" refers to a 3- to 7-membered saturated heterocyclic group having an oxygen or sulfur atom as a member of the ring such as a tetrahydrofuryl, tetrahydrothienyl, tetrahydropyranyl group and the like.

The term "lower alkoxy group" refers to a straight chained or branched alkoxy group having 1 to 6 carbon atoms such as a methoxy, ethoxy, propoxy, isopropoxy, butoxy isobutoxy, sec-butoxy, tert-butoxy, pentyloxy, hexyloxy group and the like. Preferred lower alkoxy groups for $R^3$, $R^4$, $R^5$ and $R^6$ are a $C_{1-4}$ alkoxy group, and more preferably a methoxy group. Preferred alkoxy groups for $R^7$, $R^8$ and $R^9$ are a $C_{1-4}$ alkoxy group, and more preferably a methoxy, ethoxy, propoxy or isopropoxy group. Preferred alkoxy groups for $R^{10}$ are a $C_{1-4}$ alkoxy group, and more preferably an ethoxy, propoxy, isopropoxy or butoxy group.

The term "di(lower alkyl)amino group" refers to an amino group substituted with two lower alkyl groups such as a dimethylamino, diethylamino group and the like.

The term "di(lower alkyl)amino-lower alkyl group" refers to a lower alkyl group substituted with a di(lower alkyl)amino group such as a dimethylaminomethyl group and the like.

The term "lower acyl group" refers to a group represented by (lower alkyl)-CO— such as an acetyl, propionyl, butyryl, isobutyryl, pivaloyl, valeryl, isovaleryl group and the like, preferably an acetyl group.

The term "lower alkylsulfanyl group" refers to a group represented by (lower alkyl)-S— such as a methylsulfanyl, ethylsulfanyl, propylsulfanyl, isopropylsulfanyl, butylsulfanyl, pentylsulfanyl, hexysulfanyl and the like, preferably a methylsulfanyl or ethylsulfanyl group.

The term "lower alkylsulfonyl group" refers to a group represented by (lower alkyl)-$SO_2$— such as a methanesulfonyl, ethanesulfonyl, propanesulfonyl, butanesulfonyl, pentanesulfonyl, hexanesulfonyl group and the like, preferably a methanesulfonyl group.

The term "lower alkoxycarbonyl group" refers to a group represented by (lower alkoxy)-CO— such as a methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, hexyoxycarbonyl group and the like, preferably a methoxycarbonyl, ethoxycarbonyl, propoxycarbonyl, isopropoxycarbonyl or butoxycarbonyl group.

The term "aryl group" refers to an aromatic hydrocarbon group having 6 to 14 carbon atoms, which is unsubstituted or substituted with 1 to 3 substituents selected independently from the group consisting of a halogen atom, a lower alkyl, halo-lower alkyl, lower alkoxy, hydroxyl, carboxy and lower alkoxycarbonyl group such as a phenyl, 2-fluorophenyl, 3-fluorophenyl, 4-fluorophenyl, 2-chlorophenyl, 3,5-dichlorophenyl, 4-methylphenyl, 4-trifluoromethylphenyl, 2-methoxyphenyl, 4-methoxyphenyl, 4-hydroxyphenyl, 4-carboxyphenyl, 4-methoxycarbonylphenyl, naphthyl, anthryl, phenanthryl group and the like, preferably a phenyl group.

The term "aryloxy group" refers to a group represented by (aryl)-O— such as a phenoxy, 2-fluorophenoxy, 3-fluorophenoxy, 4-fluorophenoxy, 2-chlorophenoxy, 4-chlorophenoxy, 3,5-dichlorophenoxy, 4-methylphenoxy, 4-trifluoromethylphenoxy, 2-methoxyphenoxy, 4-methoxyphenoxy, 2-hydroxyphenoxy, 4-carboxyphenoxy, 4-methoxycarbonylphenoxy, naphtyloxy, anthryloxy, phenathryloxy group and the like, preferably a phenoxy, 4-fluorophenoxy, 4-chlorophenoxy, 4-methylphenoxy or 4-methoxyphenoxy group.

The term "aralkyloxy group" refers to a lower alkoxy group substituted with an aryl group such as a benzyloxy, phenethyloxy, 3-phenylpropyloxy, 2-fluorobenzyloxy, 3-fluorobenzyloxy, 4-fluorobenzyloxy, 2-chlorobenzyloxy, 3,5-dichlorobenzyloxy, 4-methylbenzyloxy, 4-trifluoromethylbenzyloxy, 2-methoxybenzyloxy, 2-hydroxybenzyloxy, 4-carboxybenzyloxy, 4-methoxycarbonylbenzyloxy group and the like, preferably a benzyloxy group.

The term "aralkyloxycarbonyl group" refers to a group represented by (aralkyloxy)-CO— such as a benzyoxycarbonyl, phenethyloxycarbonyl, 3-phenylpropyloxycarbonyl and the like, preferably a benzyloxycarbonyl group.

The term "heteroaryl group" refers to a 5- or 6-membered aromatic heterocyclic group having 1 to 5 carbon atoms and 1 to 4 heteroatoms selected independently from the group consisting of a nitrogen, oxygen and sulfur atom, provided that said heterocycles do not include adjacent oxygen and/or sulfur atoms. Examples of heteroaryl groups include a pyrrolyl, furyl, thienyl, imidazolyl, pyrazolyl, 1,2,4-triazolyl, oxazolyl, thiazolyl, isoxazolyl, tetrazolyl, pyridyl, pyrazinyl, pyrimidyl group and the like. The heterocycles include all position isomers such as 2-pyridyl, 3-pyridyl or 4-pyridyl. The heterocycles may be optionally substituted with 1 to 3 substituents selected independently from the group consisting of a halogen atom, a lower alkyl, halo-lower alkyl, lower alkoxy, hydroxyl, carboxy and lower alkoxycarbonyl group. Preferred heteroaryl groups are an imidazolyl, pyrazolyl, thiazolyl, pyridyl, pyrazinyl or pyrimidyl group.

The term "carboxy-lower alkyl group" refers to a lower alkyl group substituted with a carboxy group such as a carboxymethyl, 2-carboxyethyl, 1-carboxyethyl, 3-carboxypropyl, 4-carboxybutyl group and the like, preferably a carboxymethyl group.

The term "lower alkoxycarbonyl-lower alkyl group" refers to a lower alkyl group substituted with a lower alkoxycarbonyl group such as a methoxycarbonylmethyl, ethoxycarbonylmethyl, propoxycarbonylmethyl, isopropoxycarbonylmethyl, butoxycarbonylmethyl, 2-(ethoxycarbonyl)ethyl, 1-(ethoxycarbonyl)ethyl, 3-(ethoxycarbonyl)propyl, 4-(ethoxycarbonyl)butyl group and the like, preferably a methoxycarbonylmethyl, ethoxycarbonylmethyl, propoxycarbonylmethyl, isopropoxycarbonylmethyl or butoxycarbonylmethyl group.

The term "cyclic amine or cyclic amino group" refers to a 5- to 7-membered saturated cyclic amino group which may contain an oxygen atom as a member of the ring such as a pyrrolidyl, piperidyl, morpholinyl group and the like.

The term "lower alkylene group" refers to a bivalent saturated hydrocarbon chain having 1 to 4 carbon atoms, which may be straight chained or branched. Examples of lower alkylene groups include —$CH_2$—, —$CH_2CH_2$—, —CH($CH_3$)—, —$CH_2CH_2CH_2$—, —CH($CH_3$)$CH_2$—, —$CH_2$CH($CH_3$)—, —C($CH_3$)$_2$—, —CH($CH_2CH_3$)—, —$CH_2CH_2CH_2CH_2$— and the like, preferably —$CH_2$—.

The term "lower alkenylene group" refers to a bivalent unsatutated hydrocarbon chain having 2 to 4 carbon atoms, which may be straight chained or branched and contains at least one double bond such as —CH=CH—, —C($CH_3$)=CH—, —CH=CH$CH_2$—, —$CH_2$CH=CH— and the like.

In a compound represented by general formula (I), the term "biphenyl bond" represents a bond between the phenyl ring substituted with $R^3$, $R^4$, $R^5$ or $R^6$ and the phenyl ring substituted with $R^7$, $R^8$ or $R^9$.

In the case where a compound represented by general formula (I) contains one or more asymmetric carbons, then all stereoisomers in the R- or S-configuration at each of asymmetric carbons and their mixture are contemplated within the scope of the present invention. In such cases, racemic compounds, racemic mixtures, individual enantiomers and mixtures of diastereomers are also contemplated within the scope of the present invention. In the case where a compound represented by general formula (I) exists in one or more geometrical isomers, then all geometrical isomers such as cis isomer, trans isomer and the mixture thereof are also contemplated within the scope of the present invention. A compound represented by general formula (I) may form a solvate with a pharmaceutically acceptable solvent such as water, ethanol and the like.

Compounds represented by general formula (I) may exist in the form of salts. Examples of such salts include acid addition salts formed with mineral acids such as hydrochloric acid, hydrobromic acid, hydroiodic acid, sulfuric acid, nitric acid, phosphoric acid and the like; acid addition salts formed with organic acids such as formic acid, acetic acid, methanesulfonic acid, benzenesulfonic acid, p-toluenesulfonic acid, propionic acid, citric acid, succinic acid, tartaric acid, fumaric acid, butyric acid, oxalic acid, malonic acid, maleic acid, lactic acid, malic acid, carbonic acid, glutamic acid, aspartic acid and the like; basic salts formed with inorganic bases such as sodium, potassium, calcium and the like; basic salts formed with organic bases such as triethylamine, piperidine, morpholine, lysine, ethylenediamine and the like.

The term "prodrug" as used herein refers to a compound which can be converted into a compound represented by general formula (I) in vivo. Such prodrugs are also contemplated within the scope of the present invention. Various forms of prodrugs are well known in the art.

In the case where a compound represented by formula (I) contains a carboxylic acid as a functional group, then a prodrug may include an ester formed by the replacement of the hydrogen atom of the carboxylic acid group with the following groups: a lower alkyl group such as a methyl, ethyl, propyl, isopropyl, butyl, tert-butyl group and the like; a lower acyloxymethyl group such as a pivaloyloxymethyl group and the like; a 1-(lower acyloxy)ethyl group such as a 1-(pivaloyloxy)ethyl group and the like; a lower alkoxycarbonyloxymethyl group such as a tert-butoxycarbonyloxymethyl group and the like; a 1-(lower alkoxycarbonyloxy)ethyl group such as a 1-(tert-butoxycarbonyloxy)ethyl group and the like; or a 3-phthalidyl group.

In the case where a compound represented by formula (I) contains a hydroxyl group, then a prodrug may include a compound formed by the replacement of the hydrogen atom of the hydroxyl group with the following groups: a lower acyl group such as an acetyl, propionyl, butyryl, isobutyryl, pivaloyl group and the like; a lower alkoxycarbonyl group such as a methoxycarbonyl, ethoxycarbonyl, propoxycarbonyl, isopropoxycarbonyl, tert-butoxycarbonyl group and the like; a succinoyl group; a lower acyloxymethyl group such as a pivaloyloxymethyl group and the like; a 1-(lower acyloxy)ethyl group such as 1-(pivaloyloxy)ethyl group and the like; or a lower alkoxycarbonyloxymethyl group such as a tert-butoxycarbonyloxymethyl group and the like.

In the case where a compound represented by formula (I) contains an amino group such as —NH or —NH$_2$, then a prodrug may include a compound formed by the replacement of the hydrogen atom of the amino group with the following groups: a lower acyl group such as an acetyl, propionyl, butyryl, isobutyryl, pivaloyl group and the like; or a lower alkoxycarbonyl group such as a methoxycarbonyl, ethoxycarbonyl, propoxycarbonyl, isopropoxycarbonyl, tert-butoxycarbonyl group and the like.

The prodrug compounds described above may be prepared from compounds represented by general formula (I) according to known methods as described in T. W. Green and P. G. H. Wuts, "Protective Groups in Organic Synthesis" the third edition and references described therein.

In an embodiment of a compound represented by general formula (I), preferred $R^1$ and $R^2$ are each independently a hydrogen atom or a $C_{1-4}$ lower alkyl group, and more preferably a hydrogen atom;

in one aspect, $R^3$, $R^4$, $R^5$ and $R^6$ are each independently a hydrogen, halogen atom, a lower alkyl or lower alkoxy group, preferably a hydrogen, halogen atom or a lower alkyl group, and more preferably a hydrogen atom or a lower alkyl group, provided that at least one of $R^3$, $R^4$, $R^5$ and $R^6$ is a halogen atom, a lower alkyl or lower alkoxy group, in another aspect, $R^3$, $R^4$, $R^5$ and $R^6$ are a hydrogen atom;

preferred $R^7$ and $R^8$ are each independently a hydrogen, halogen atom, a lower alkyl, halo-lower alkyl, cycloalkyl, lower alkoxy, aryloxy, lower alkylsulfanyl, hydroxyl or lower acyl group, and more preferably a hydrogen, halogen atom, a lower alkyl, cycloalkyl, lower alkoxy, aryloxy, hydroxyl or lower acyl group; and $R^9$ is preferably —C(O)—$R^{10}$ or —OCH$_2$C(O)—$R^{10}$ in which $R^{10}$ is preferably a hydroxyl or lower alkoxy group.

A preferable embodiment of the present invention is a compound represented by general formula (II):

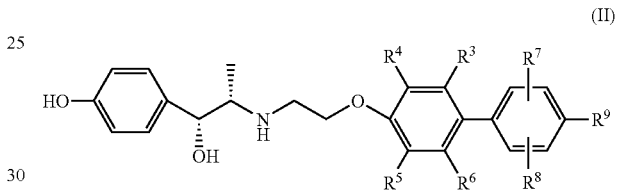

or a pharmaceutically acceptable salt thereof, wherein each of $R^3$, $R^4$, $R^5$ and $R^6$ is independently a hydrogen, halogen atom, a lower alkyl or lower alkoxy group;

each of $R^7$ and $R^8$ is independently a hydrogen, halogen atom, a lower alkyl, halo-lower alkyl, cycloalkyl, lower alkoxy, aryloxy, lower alkylsulfanyl, hydroxyl or lower acyl group; $R^9$ is —C(O)—$R^{10}$ or —OCH$_2$C(O)—$R^{10}$; and $R^{10}$ is a hydroxyl, lower alkoxy or aralkyloxy group;

provided that at least one of $R^3$, $R^4$, $R^5$ and $R^6$ is a halogen atom, a lower alkyl or lower alkoxy group.

In a compound represented by general formula (II), $R^7$ is preferably a hydrogen atom;

$R^8$ is preferably a hydrogen, halogen atom, a lower alkyl, cycloalkyl, lower alkoxy, aryloxy, hydroxyl or lower acyl group, more preferably a lower alkyl, cycloalkyl, lower alkoxy, aryloxy, hydroxyl or lower acyl group, and even more preferably a lower alkyl, lower alkoxy, aryloxy or lower acyl group;

in one aspect, when $R^3$ and $R^6$ are a hydrogen atom, $R^4$ is preferably a hydrogen, halogen atom or a lower alkyl group, $R^5$ is preferably a halogen atom or a lower alkyl group, and more preferably $R^4$ and $R^5$ are each independently a lower alky group, in another aspect, when $R^4$ and $R^6$ are a hydrogen atom, $R^3$ is preferably a halogen atom or a lower alkyl group, and $R^5$ is preferably a hydrogen, halogen atom or a lower alkyl group.

Another preferable embodiment of the present invention is a compound represented by general formula (III):

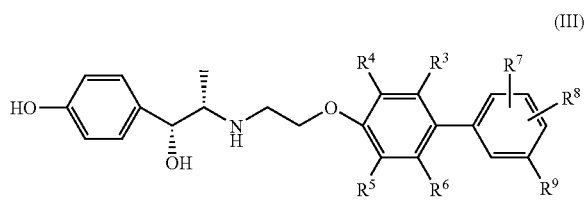

(III)

or a pharmaceutically acceptable salt thereof, wherein
each of $R^3$, $R^4$, $R^5$ and $R^6$ is independently a hydrogen, halogen atom, a lower alkyl or lower alkoxy group;
each of $R^7$ and $R^8$ is independently a hydrogen, halogen atom, a lower alkyl, halo-lower alkyl, cycloalkyl, lower alkoxy, aryloxy, lower alkylsulfanyl, hydroxyl or lower acyl group; $R^9$ is —C(O)—$R^{10}$ or —OCH$_2$C(O)—$R^{10}$; and
$R^{10}$ is a hydroxyl, lower alkoxy or aralkyloxy group;
provided that at least one of $R^3$, $R^4$, $R^5$ and $R^6$ is a halogen atom, a lower alkyl or lower alkoxy group.

In a compound represented by general formula (III),
$R^3$ and $R^6$ are preferably a hydrogen atom;
$R^4$ is preferably a hydrogen atom or a lower alkyl;
$R^5$ is preferably a lower alkyl group;
$R^7$ is preferably a hydrogen atom; and
$R^8$ is preferably a halogen atom or a lower alkyl group.

Still another preferable embodiment of the present invention is a compound represented by general formula (IV):

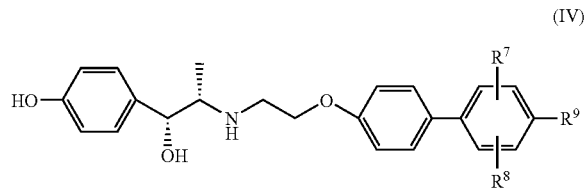

(IV)

or a pharmaceutically acceptable salt thereof, wherein
each of $R^7$ and $R^8$ is independently a hydrogen, halogen atom, a lower alkyl, halo-lower alkyl, cycloalkyl, lower alkoxy or aryloxy group;
$R^9$ is —C(O)—$R^{10}$ or —OCH$_2$C(O)—$R^{10}$; and
$R^{10}$ is a hydroxyl, lower alkoxy or aralkyloxy group.

In a compound represented by general formula (IV),
$R^7$ is preferably a hydrogen atom;
$R^8$ is preferably a halogen atom, a lower alkyl, halo-lower alkyl, cycloalkyl, lower alkoxy or aryloxy group, and more preferably a lower alkyl, halo-lower alkyl or aryloxy group.

Specific examples of preferred embodiments of the present invention are compounds selected form the group consisting of:

4'-{2-[(1S,2R)-2-hydroxy-2-(4-hydroxyphenyl)-1-methylethylamino]ethoxy)-2,3',5'-trimethylbiphenyl-4-carboxylic acid;

4'-{2-[(1S,2R)-2-hydroxy-2-(4-hydroxyphenyl)-1-methylethylamino]ethoxy}-3-isopropyl-3',5'-dimethylbiphenyl-4-carboxylic acid;

(3-acetyl-4'-{2-[(1S,2R)-2-hydroxy-2-(4-hydroxyphenyl)-1-methylethylamino]ethoxy}-3',5'-dimethylbiphenyl-4-yloxy)acetic acid;

4'-{2-[(1R,2S)-2-hydroxy-2-(4-hydroxyphenyl)-1-methylethylamino]ethoxy}-2,2'-dimethylbiphenyl-4-caboxylic acid;

2-ethyl-4'-{2-[(1S,2R)-2-hydroxy-2-(4-hydroxyphenyl)-1-methylethylamino]ethoxy}-2'-methylbiphenyl-4-carboxylic acid;

4'-{2-[(1S,2R)-2-hydroxy-2-(4-hydroxyphenyl)-1-methylethylamino]ethoxy}-2-isopropyl-2'-methylbiphenyl-4-carboxylic acid;

4'-{2-[(1S,2R)-2-hydroxy-2-(4-hydroxyphenyl)-1-methylethylamino]ethoxy}-2'-methyl-2-propylbiphenyl-4-carboxylic acid;

4'-{2-[(1R,2S)-2-hydroxy-2-(4-hydroxyphenyl)-1-methylethylamino]ethoxy}-2-methoxy-3',5'-dimethylbiphenyl-4-carboxylic acid;

4'-{2-[(1R,2S)-2-hydroxy-2-(4-hydroxyphenyl)-1-methylethylamino]ethoxy}-3',5'-dimethylbiphenyl-4-carboxylic acid;

2-ethyl-4'-{2-[(1R,2S)-2-hydroxy-2-(4-hydroxyphenyl)-1-methylethylamino]ethoxy}-3'-methylbiphenyl-4-carboxylic acid;

4'-{2-[(1R,2S)-2-hydroxy-2-(4-hydroxyphenyl)-1-methylethylamino]ethoxy}-3'-methyl-2-propylbiphenyl-4-carboxylic acid;

3-cyclopentyl-4'-{2-[(1R,2S)-2-hydroxy-2-(4-hydroxyphenyl)-1-methylethylamino]ethoxy}-3'-methylbiphenyl-4-carboxylic acid;

2-ethyl-3'-fluoro-4'-{2-[(1R,2S)-2-hydroxy-2-(4-hydroxyphenyl)-1-methylethylamino]ethoxy}biphenyl-4-carboxylic acid;

3'-fluoro-4'-{2-[(1R,2S)-2-hydroxy-2-(4-hydroxyphenyl)-1-methylethylamino]ethoxy}-2-isopropylbiphenyl-4-carboxylic acid;

3'-fluoro-4'-{2-[(1R,2S)-2-hydroxy-2-(4-hydroxyphenyl)-1-methylethylamino]ethoxy}-2-propylbiphenyl-4-carboxylic acid;

(4'-{2-[(1S,2R)-2-hydroxy-2-(4-hydroxyphenyl)-1-methylethylamino]ethoxy}-2,3',5'-trimethylbiphenyl-4-yloxy)acetic acid;

3-hyroxy-4'-{2-[(1S,2R)-2-hydroxy-2-(4-hydroxyphenyl)-1-methylethylamino]ethoxy}-3',5'-dimethylbiphenyl-4-carboxylic acid;

4'-{2-[(1R,2S)-2-hydroxy-2-(4-hydroxyphenyl)-1-methylethylamino]ethoxy}-3',5'-dimethyl-3-(p-tolyloxy)biphenyl-4-carboxylic acid;

3-(4-chlorophenoxy)-4'-{2-[(1R,2S)-2-hydroxy-2-(4-hydroxyphenyl)-1-methylethylamino]ethoxy}-3',5'-dimethylbiphenyl-4-carboxylic acid;

3-(4-fluorophenoxy)-4'-{2-[(1R,2S)-2-hydroxy-2-(4-hydroxyphenyl)-1-methylethylamino]ethoxy}-3',5'-dimethylbiphenyl-4-carboxylic acid;

4'-{2-[(1R,2S)-2-hydroxy-2-(4-hydroxyphenyl)-1-methylethylamino]ethoxy}-3-(4-methoxyphenoxy)-3',5'-dimethylbiphenyl-4-carboxylic acid;

4'-{2-[(1R,2S)-2-hydroxy-2-(4-hydroxyphenyl)-1-methylethylamino]ethoxy}-3'-methyl3-phenoxybiphenyl-4-carboxylic acid;

4'-{2-[(1R,2S)-2-hydroxy-2-(4-hydroxyphenyl)-1-methylethylamino]ethoxy}-3-(4-methoxyphenoxy)-3'-methylbiphenyl-4-carboxylic acid;

3'-fluoro-4'-{2-[(1R,2S)-2-hydroxy-2-(4-hydroxyphenyl)-1-methylethylamino]ethoxy}-3-(4-methoxyphenoxy)biphenyl-4-carboxylic acid;

3-(4-chlorophenoxy)-3'-fluoro-4'-{2-[(1R,2S)-2-hydroxy-2-(4-hydroxyphenyl)-1-methylethylamino]ethoxy}biphenyl-4-carboxylic acid;

4'-{2-[(1R,2S)-2-hydroxy-2-(4-hydroxyphenyl)-1-methylethylamino]ethoxy}-2'-methyl-3-phenoxybiphenyl-4-carboxylic acid;

3-(4-fluorophenoxy)-4'-{2-[(1R,2S)-2-hydroxy-2-(4-hydroxyphenyl)-1-methylethylamino]ethoxy}-2'-methylbiphenyl-4-carboxylic acid;

4'-{2-[(1R,2S)-2-hydroxy-2-(4-hydroxyphenyl)-1-methylethylamino]ethoxy}-6-methoxy-2'-methylbiphenyl-3-carboxylic acid;

4'-{2-[(1R,2S)-2-hydroxy-2-(4-hydroxyphenyl)-1-methylethylamino]ethoxy}-6-methoxy-3',5'-dimethylbiphenyl-3-carboxylic acid;

6-chloro-4'-{2-[(1R,2S)-2-hydroxy-2-(4-hydroxyphenyl)-1-methylethylamino]ethoxy}-3',5'-dimethylbiphenyl-3-carboxylic acid;

6-chloro-4'-{2-[(1R,2S)-2-hydroxy-2-(4-hydroxyphenyl)-1-methylethylamino]ethoxy}-3'-methylbiphenyl-3-carboxylic acid;

2-ethyl-4'-{2-[(1R,2S)-2-hydroxy-2-(4-hydroxyphenyl)-1-methylethylamino]ethoxy}biphenyl-4-carboxylic acid;

4'-{2-[(1R,2S)-2-hydroxy-2-(4-hydroxyphenyl)-1-methylethylamino]ethoxy}-2-methylbiphenyl-4-carboxylic acid;

4'-{2-[(1R,2S)-2-hydroxy-2-(4-hydroxyphenyl)-1-methylethylamino]ethoxy}-2-isopropylbiphenyl-4-carboxylic acid;

4'-{2-[(1R,2S)-2-hydroxy-2-(4-hydroxyphenyl)-1-methylethylamino]ethoxy}-2-trifluoromethylbiphenyl-4-carboxylic acid;

4'-{2-[(1R,2S)-2-hydroxy-2-(4-hydroxyphenyl)-1-methylethylamino]ethoxy}-3-propylbiphenyl-4-carboxylic acid;

4'-{2-[(1R,2S)-2-hydroxy-2-(4-hydroxyphenyl)-1-methylethylamino]ethoxy}-2-propylbiphenyl-4-carboxylic acid;

3-sec-butyl-4'-{2-[(1R,2S)-2-hydroxy-2-(4-hydroxyphenyl)-1-methylethylamino]ethoxy}biphenyl-4-carboxylic acid;

3-cyclopentyl-4'-{2-[(1R,2S)-2-hydroxy-2-(4-hydroxyphenyl)-1-methylethylamino]ethoxy}biphenyl-4-carboxylic acid;

4'-{2-[(1R,2S)-2-hydroxy-2-(4-hydroxyphenyl)-1-methylethylamino]ethoxy}-3-phenoxybiphenyl-4-carboxylic acid;

4'-{2-[(1R,2S)-2-hydroxy-2-(4-hydroxyphenyl)-1-methylethylamino]ethoxy}-3-(4-methoxyphenoxy)biphenyl-4-carboxylic acid;

3-(4-chlorophenoxy)-4'-{2-[(1R,2S)-2-hydroxy-2-(4-hydroxyphenyl)-1-methylethylamino]ethoxy}biphenyl-4-carboxylic acid;

3-(4-fluorophenoxy)-4'-{2-[(1R,2S)-2-hydroxy-2-(4-hydroxyphenyl)-1-methylethylamino]ethoxy}biphenyl-4-carboxylic acid; and 4'-{2-[(1R,2S)-2-hydroxy-2-(4-hydroxyphenyl)-1-methylethylamino]ethoxy}-3-(p-tolyloxy)biphenyl-4-carboxylic acid, or a lower alkyl ester thereof, or a pharmaceutically acceptable salt thereof.

Compounds represented by general formula (I) can be prepared by methods as illustrated in schemes 1 to 5.

Scheme 1

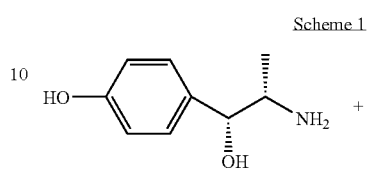

(X)

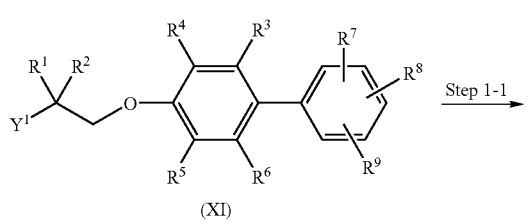

(XI)

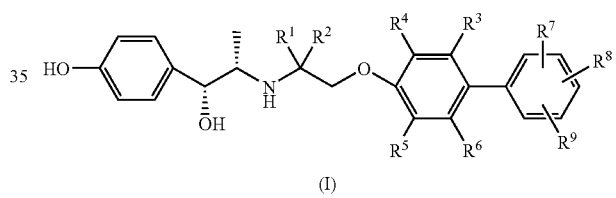

(I)

wherein $R^1$, $R^2$, $R^3$, $R^4$, $R^5$, $R^6$, $R^7$, $R^8$ and $R^9$ are as defined above; and $Y^1$ is an eliminating group such as a chlorine, bromine, iodine atom, a methanesulfonyloxy or p-toluenesulfonyloxy group or the like.

(Step 1-1)

Amino alcohol derivative (X) is treated with alkylating agent (XI) in the presence or absence of a base such as N,N-diisopropylethylamine, triethylamine or the like in an inert solvent such as N,N-dimethylformamide, acetonitrile or the like to afford a compound represented by general formula (I).

In the cases where compound (I) contains a carboxylic ester group in $R^7$, $R^8$ or $R^9$, compound (I) can be converted into the corresponding carboxylic acid by hydrolysis using an aqueous solution of alkali in a suitable solvent such as ethanol or the like. In the cases where compound (I) contains a carboxylic ester group in $R^9$, compound (I) can be treated with an amine represented by $NHR^{11}R^{12}$ in the presence of a condensing agent such as diphenylphosphorylazide, diethyl cyanophosphate, 1-(3-dimethylaminopropyl)-3-ethylcarbodiimide hydrochloride or the like to provide the corresponding carboxylic amide.

Scheme 2

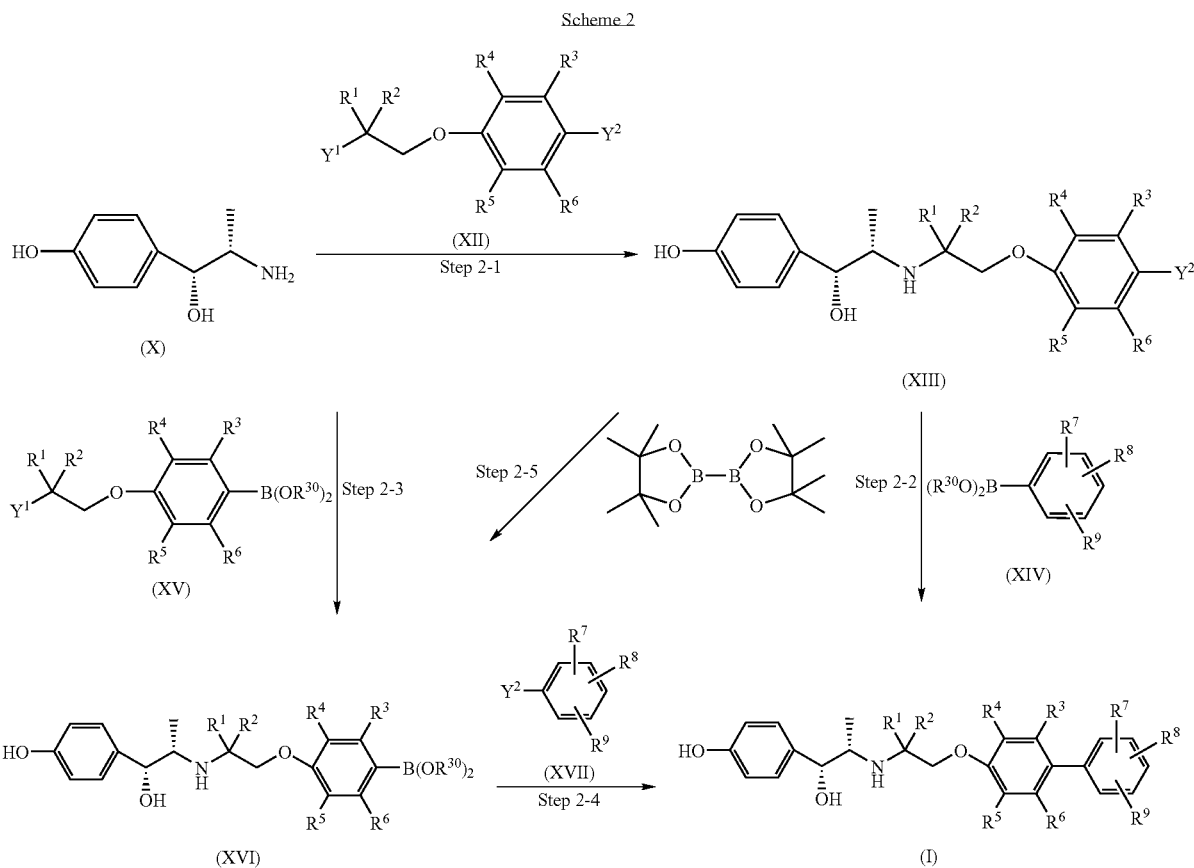

wherein $R^1$, $R^2$, $R^3$, $R^4$, $R^5$, $R^6$, $R^7$, $R^8$, $R^9$ and $Y^1$ are as defined above; $R^{30}$ is a hydrogen atom or a lower alkyl group, or two $R^{30}$ are joined to form a group represented by —$C(CH_3)_2C(CH_3)_2$—; and $Y^2$ is a chlorine, bromine, iodine atom, a trifluoromethanesulfonyloxy group or the like.

(Steps 2-1 and 2-2)

A compound represented by general formula (XIII) can be prepared by treating amino alcohol derivative (X) with alkylating agent (XII) according to procedures analogous to those as described in step 1-1.

The compound (XIII) is treated with boronic acid derivative (XIV) in the presence of a palladium catalyst and a base in an inert solvent to afford compound (I). The solvent employed in the reaction includes N,N-dimethylformamide, 1,4-dioxane, toluene or the like. The palladium catalyst includes tetrakis(triphenylphosphine)palladium(0), dichlorobis(triphenylphosphine)palladium(II) or the like. The base includes cesium fluoride, sodium carbonate or the like. The reaction may be carried out, if necessary, with the addition of a ligand such as bis (diphenylphosphino) ferrocene or the like.

(Steps 2-3 and 2-4)

Alternatively, compound (I) can be prepared as follows. Amino alcohol derivative (X) is treated with alkylating agent (XV) according to procedures analogous to those as described in step 1-1 to afford a compound of general formula (XVI). Thereafter, the compound (XVI) is treated with compound (XVII) according to procedures analogous to those as described in step 2-2 to afford compound (I).

(Step 2-5)

The compound (XVI) can also be prepared by treating compound (XIII) with bis(pinacolato)diboron in the presence of a palladium catalyst and a base in an inert solvent such as N,N-dimethylformamide, 1,4-dioxane or the like. The palladium catalyst employed in the reaction includes dichlorobis (triphenylphosphine)palladium (II) or the like. The base includes potassium acetate or the like. The reaction may be carried out, if necessary, with the addition of a ligand such as bis(diphenylphosphino)ferrocene or the like.

Scheme 3

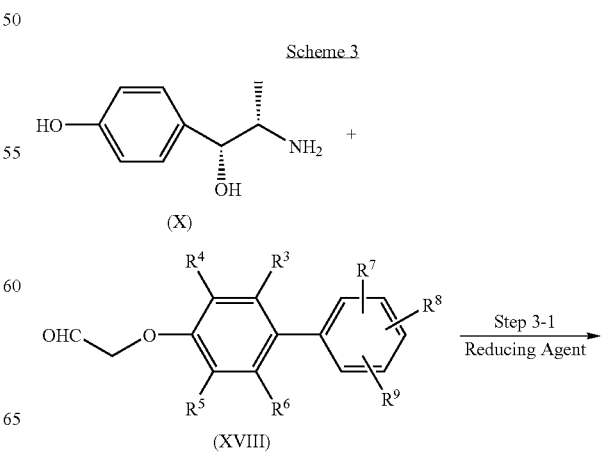

-continued

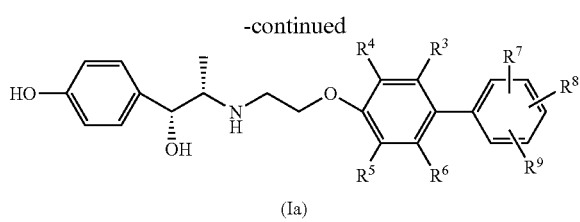

(Ia)

wherein $R^3$, $R^4$, $R^5$, $R^6$, $R^7$, $R^8$ and $R^9$ are as defined above.

(Step 3-1)

Amino alcohol derivative (X) is treated with aldehyde derivative (XVIII) in the presence of a reducing agent in a suitable solvent to afford a compound represented by general formula (Ia). The solvent in the reductive amination reaction includes ethers such as tetrahydrofuran, 1,4-dioxane or the like, halogenated hydrocarbons such as methylene chloride or the like, organic carboxylic acids such as acetic acid or the like, hydrocarbons such as toluene or the like, alcohols such as methanol, ethanol or the like, acetonitrile or the like. The solvent may be used, if necessary, as a mixture of two or more solvents. The reducing agent includes alkali metal hydroboranes such as $NaBH_4$, $NaBH_3CN$, $NaBH(OAc)_3$ or the like, boranes such as $BH_3$.pyridine, $BH_3$.N,N-diethylaniline or the like. The reaction may be carried out, if necessary, in the presence of an acid such as acetic acid, p-toluenesulfonic acid, methanesulfonic acid, sulfuric acid, hydrochloric acid or the like.

Alternatively, the reaction may be carried out under a hydrogen atmosphere in the presence of a catalytic amount of a metal catalyst such as 5 to 10% palladium on carbon, Raney-Ni, platinum oxide, palladium black, 10% platinum on carbon (sulfided) or the like in place of using reducing agents described above.

The reductive amination reaction may be carried out by selecting a suitable reducing agent depending on the kind of substituents included in compound (XVIII).

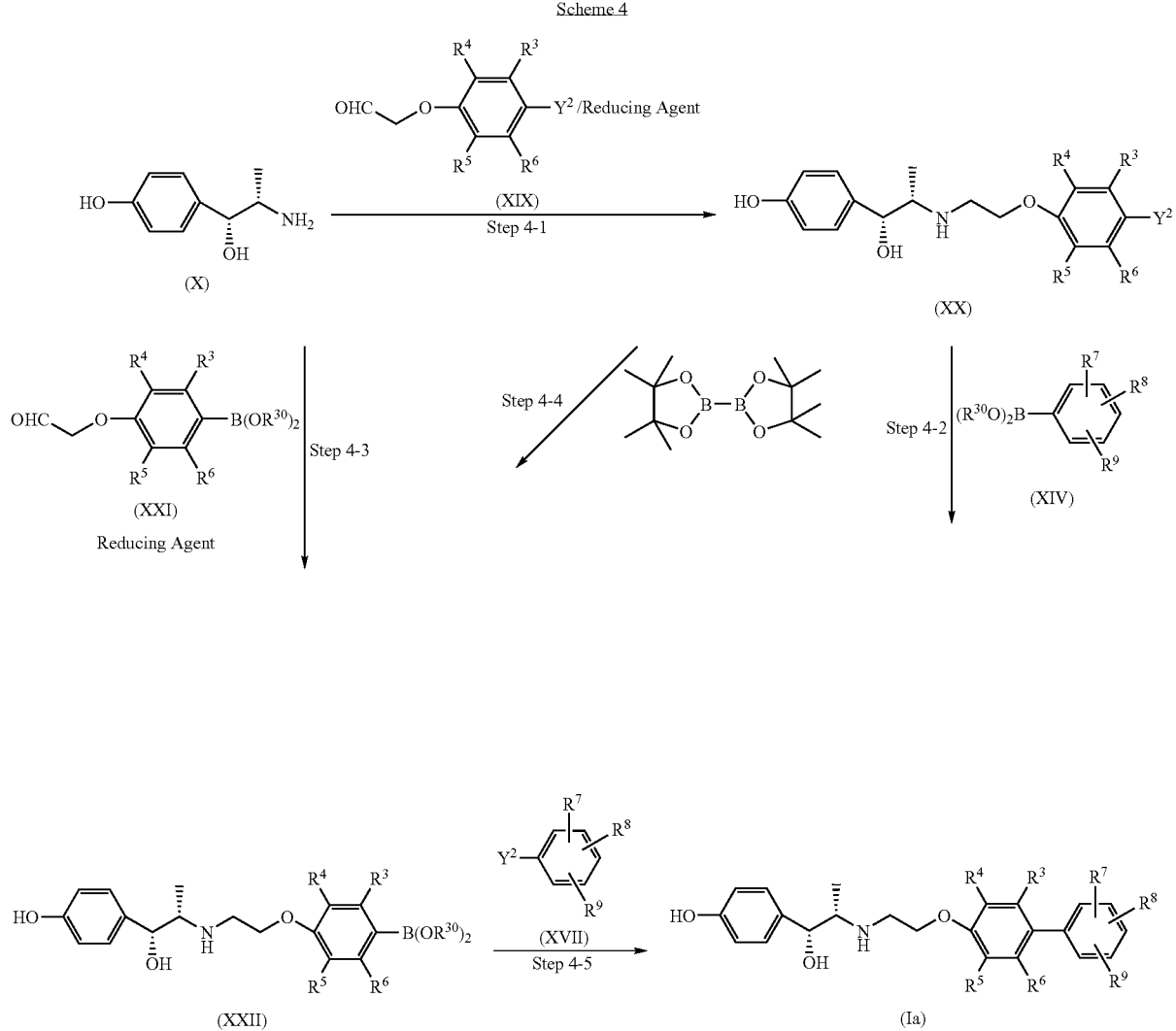

Scheme 4 wherein $R^3$, $R^4$, $R^5$, $R^6$, $R^7$, $R^8$, $R^9$, $R^{30}$ and $Y^2$ are as defined above.

(Steps 4-1 and 4-2)

A compound represented by general formula (XX) can be prepared by treating amino alcohol derivative (X) with aldehyde (XIX) according to procedures analogous to those as described in step 3-1. The compound (XX) is treated with boronic acid derivative (XIV) according to procedures analogous to those as described in step 2-2 to afford a compound of general formula (Ia).

(Steps 4-3-4-5)

Alternatively, compound (Ia) can be prepared as follows. Amino alcohol derivative (X) is treated with aldehyde (XXI) according to procedures analogous to those as described in step 3-1 to afford a compound of general formula (XXII). The compound (XXII) can also be prepared by treating compound (XX) with bis(pinacolato)diboron according to procedures analogous to those as described in step 2-5. The compound (XXII) is then treated with compound (XVII) according to procedures analogous to those as described in step 2-2 to afford compound (Ia).

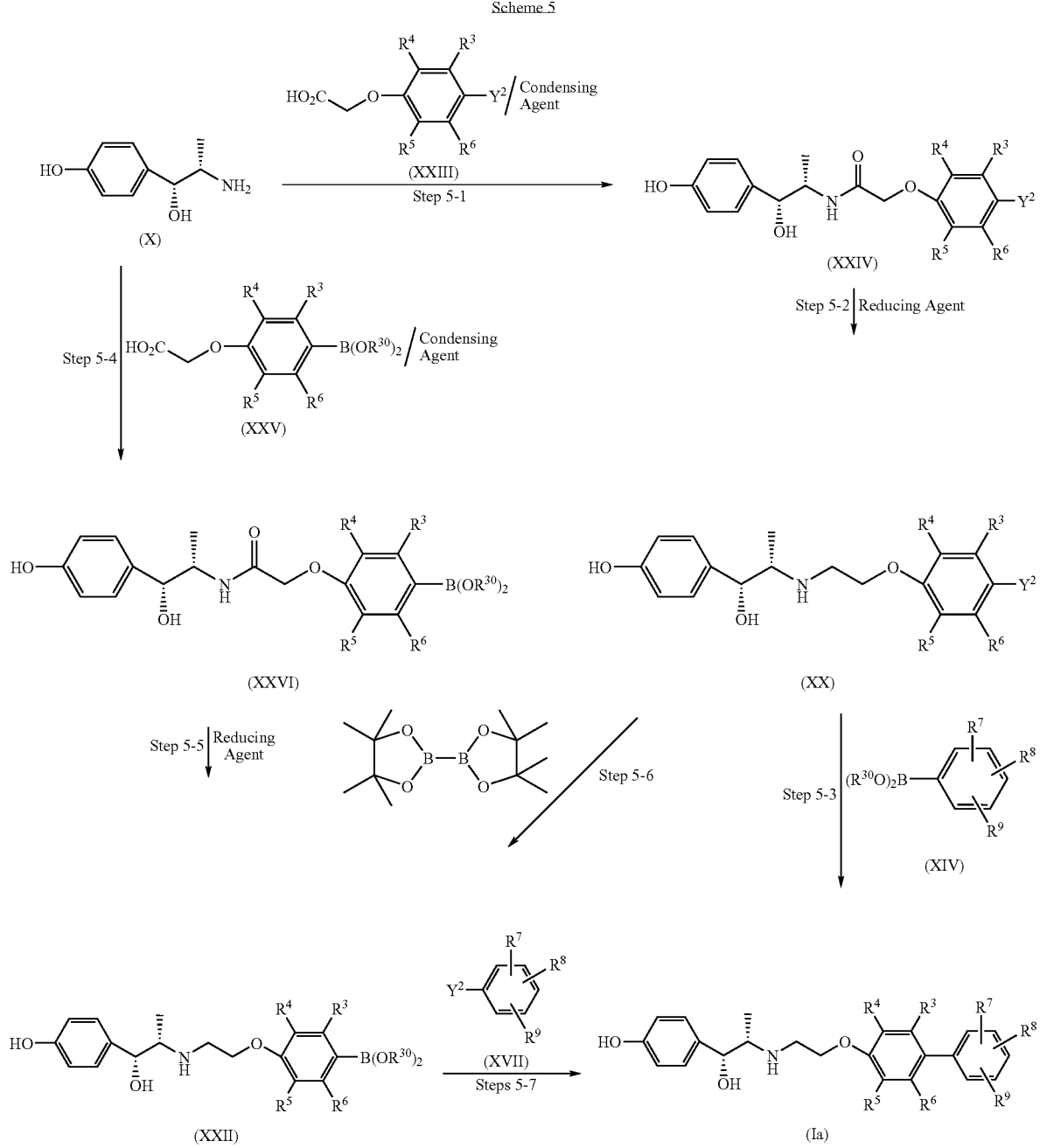

wherein $R^3$, $R^4$, $R^5$, $R^6$, $R^7$, $R^8$, $R^9$, $R^{30}$ and $Y^2$ are as defined above.

(Steps 5-1)

Amino alcohol derivative (X) is treated with carboxylic acid derivative (XXIII) in the presence of a condensing agent in an inert solvent such as tetrahydrofuran, methylene chloride, N,N-dimethylformamide or the like to afford an amide derivative of general formula (XXIV). The condensing agent employed in the amidation reaction includes diphenylphosphorylazide, diethyl cyanophosphate, 1,3-dicyclohexylcarbodiimide, 1-(3-dimethylaminopropyl)-3-ethylcarbodiimide hydrochloride, benzotriazol-1-yloxytris(dimethylamino)phosphonium hexafluorophosphate or the like. The amidation reaction can be carried out, if necessary, with the addition of an activating agent such as N-hydroxysuccinimide, 1-hydroxybenzotriazole or the like.

Alternatively, the amide derivative (XXIV) can be prepared by converting carboxylic acid derivative (XXIII) into an activated ester such as 4-nitrophenyl ester, 2,5-dioxapyrrolidine ester or the like according to conventional procedures well known to those in the art, followed by treating the activated ester with amino alcohol derivative (X).

(Steps 5-2 and 5-3)

Reduction of compound (XXIV) using a reducing agent such as diborane, borane•tetrahydrofuran complex, borane.dimethylsulfide complex, borane.pyridine complex, sodium borohydride/acetic acid or the like in an inert solvent such as tetrahydrofuran or the like provides a compound of general formula (XX).

The compound (XX) is then treated with boron derivative (XIV) according to procedures analogous to those as described in step 2-2 to afford a compound of general formula (Ia).

(Steps 5-4-5-7)

Alternatively, compound (Ia) can be prepared as follows. Amino alcohol derivative (X) is treated with carboxylic acid (XXV) according to procedures analogous to those as described in step 5-1 to afford a compound of general formula (XXVI). The compound (XXVI) is reduced according to procedures analogous to those as described in step 5-2 to afford a compound of general formula (XXII). The compound (XXII) can also be prepared from compound (XX) according to procedures analogous to those as described in step 2-5. The compound (XXII) is treated with compound (XVII) according to procedures analogous to those as described in step 2-2 to afford compound (Ia).

Of the starting materials employed in schemes 1 and 2, alkylating agents (XI), (XII) and (XV) can be prepared by methods as illustrated in scheme 6 or 7.

Scheme 6

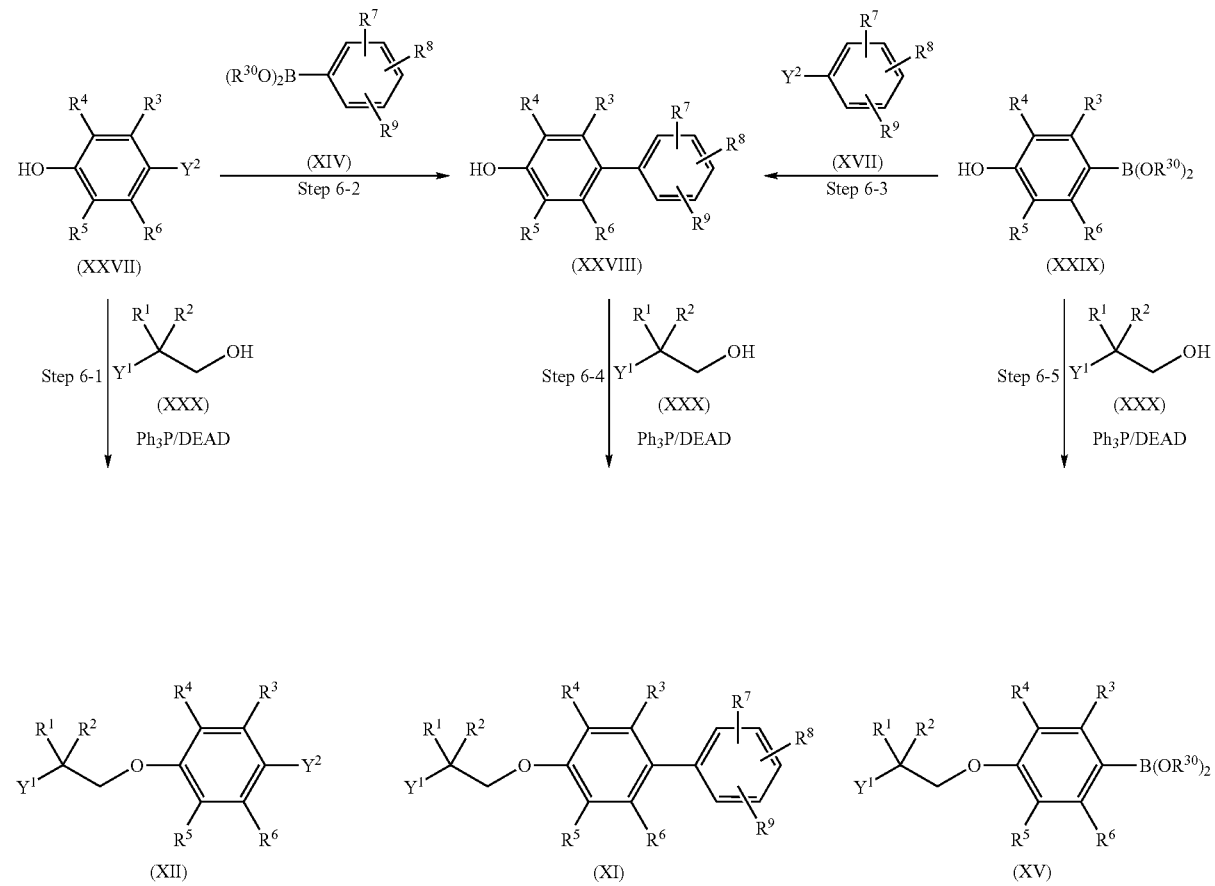

wherein $R^1, R^2, R^3, R^4, R^5, R^6, R^7, R^8, R^9, R^{30}, Y^1$ and $Y^2$ are as defined above; $Ph_3P$ represents triphenylphosphine; and DEAD represents dialkyl ester of azodicarboxylic acid.

(Step 6-1)

Mitsunobu reaction can be carried out by treating phenol derivative of general formula (XXVII) with alcohol derivative (XXX) in the presence of triphenylphosphine and dialkyl ester of azodicarboxylic acid according to procedures well known to those in the art to provide a compound of general formula (XII). Dialkyl ester of azodicarboxylic acid includes diethyl azodicarboxylate, diisopropyl azodicarboxylate or the like.

(Steps 6-2-6-4)

Phenol derivative (XXVII) is treated with boronic acid derivative (XIV) according to procedures analogous to those as described in step 2-2 to afford a compound of general formula (XXVIII). Alternatively, the compound (XXVIII) can be prepared by treating phenol derivative (XXIX) with compound (XVII) according to procedures analogous to those as described in step 2-2. The compound (XXVIII) is treated with alcohol derivative (XXX) according to procedures analogous to those as described in step 6-1 to afford a compound of general formula (XI).

(Step 6-5)

Phenol derivative (XXIX) is treated with alcohol derivative (XXX) according to procedures analogous to those as described in step 6-1 to afford a compound of general formula (XV).

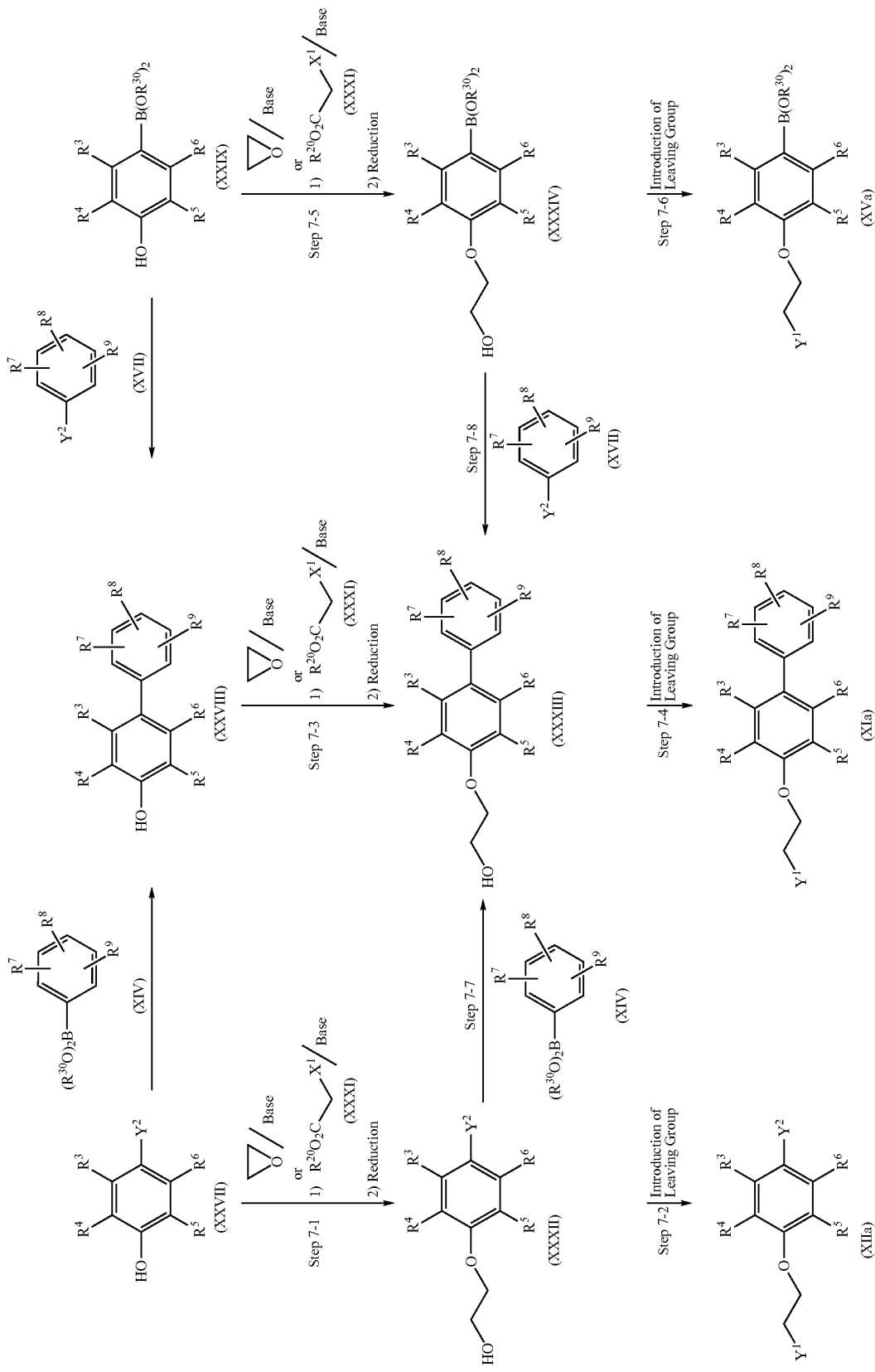

wherein $R^3$, $R^4$, $R^5$, $R^6$, $R^7$, $R^8$, $R^9$, $R^{30}$, $Y^1$ and $Y^2$ are as defined above; $R^{20}$ is a lower alkyl group; and $X^1$ is a chlorine or bromine atom.

(Step 7-1)

Phenol derivative (XXVII) is treated with ethylene oxide in the presence of a base such as potassium carbonate, sodium hydride or the like in an inert solvent such as N,N-dimethylformamide, tetrahydrofuran or the like to afford a compound of general formula (XXXII).

Alternatively, the compound (XXXII) can be prepared as follows. Phenol derivative (XXVII) is treated with compound (XXXI) in the presence of a base such as potassium carbonate, cesium carbonate or the like in an inert solvent such as N,N-dimethylformamide, acetonitrile or the like to afford a phenoxyacetic acid ester. Reduction of the phenoxyacetic acid ester using a suitable reducing agent such as borane.tetrahydrofuran complex, borane.dimethylsulfide complex, borane.pyridine complex, sodium borohydride or the like in an inert solvent such as tetrahydrofuran provides compound (XXXII).

to those as described in step 7-1. The compound (XXXIII) is then converted into a compound of general formula (XIa) according to procedures analogous to those as described in step 7-2.

(Steps 7-5 and 7-6)

Compound (XXIX) is converted into a compound of general formula (XXXIV) according to procedures analogous to those as described in step 7-1. The compound (XXXIV) is then converted into a compound of general formula (XVa) according to procedures analogous to those as described in step 7-2.

(Steps 7-7 and 7-8)

The compound (XXXIII) may also be prepared by treating compound (XXXII) with boronic acid derivative (XIV) according to procedures analogous to those as described in step 2-2. The alternate preparation of the compound (XXXIII) may be carried out by treating compound (XXXIV) with compound (XVII) according to procedures analogous to those as described in step 2-2.

Of the starting materials employed in schemes 3 and 4, aldehyde derivatives (XVIII), (XIX) and (XXI) can be prepared by methods as illustrated in scheme 8 or 9.

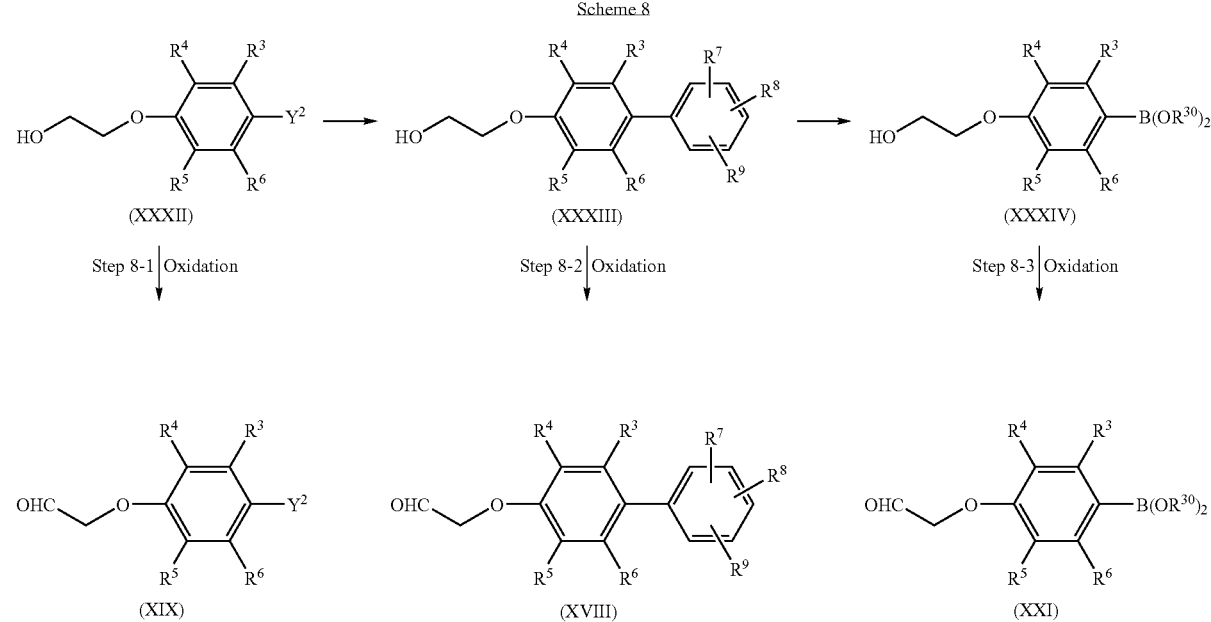

wherein $R^3$, $R^4$, $R^5$, $R^6$, $R^7$, $R^8$, $R^9$, $R^{30}$ and $Y^2$ are as defined above.

(Step 8-1)

Oxidation of alcohol derivative (XXXII) using a suitable oxidizing agent in an inert solvent such as methylene chloride or the like provides an aldehyde derivative of general formula (XIX). Such oxidizing agents include oxalyl chloride/dimethylsulfoxide, 1,1,1-triacetoxy-1,1-dihydro-1,2-benziodoxol-3(1H)-one or the like.

(Steps 8-2 and 8-3)

Alcohol derivative (XXXIII) or (XXXIV) is oxidized according to procedures analogous to those as described in step 8-1 to provide an aldehyde derivative of general formula (XVIII) or (XXI) respectively.

(Step 7-2)

The compound (XXXII) is treated with a halogenating reagent in an inert solvent such as methylene chloride, chloroform or the like to afford a compound of general formula (XIIa). The compound (XIIa) may also be prepared from compound (XXXII) by treatment of a sulfonyl halide in the presence of a base such as N,N-diisopropylethylamine or the like in an inert solvent such as methylene chloride, chloroform or the like. Such a halogenating reagent includes thionyl chloride, phosphorus tribromide, triphenylphosphine/carbon tetrabromide or the like. The sulfonyl chloride includes methanesulfonyl chloride, p-toluenesulfonyl chloride or the like.

(Steps 7-3 and 7-4)

Compound (XXVIII) is converted into a compound of general formula (XXXIII) according to procedures analogous

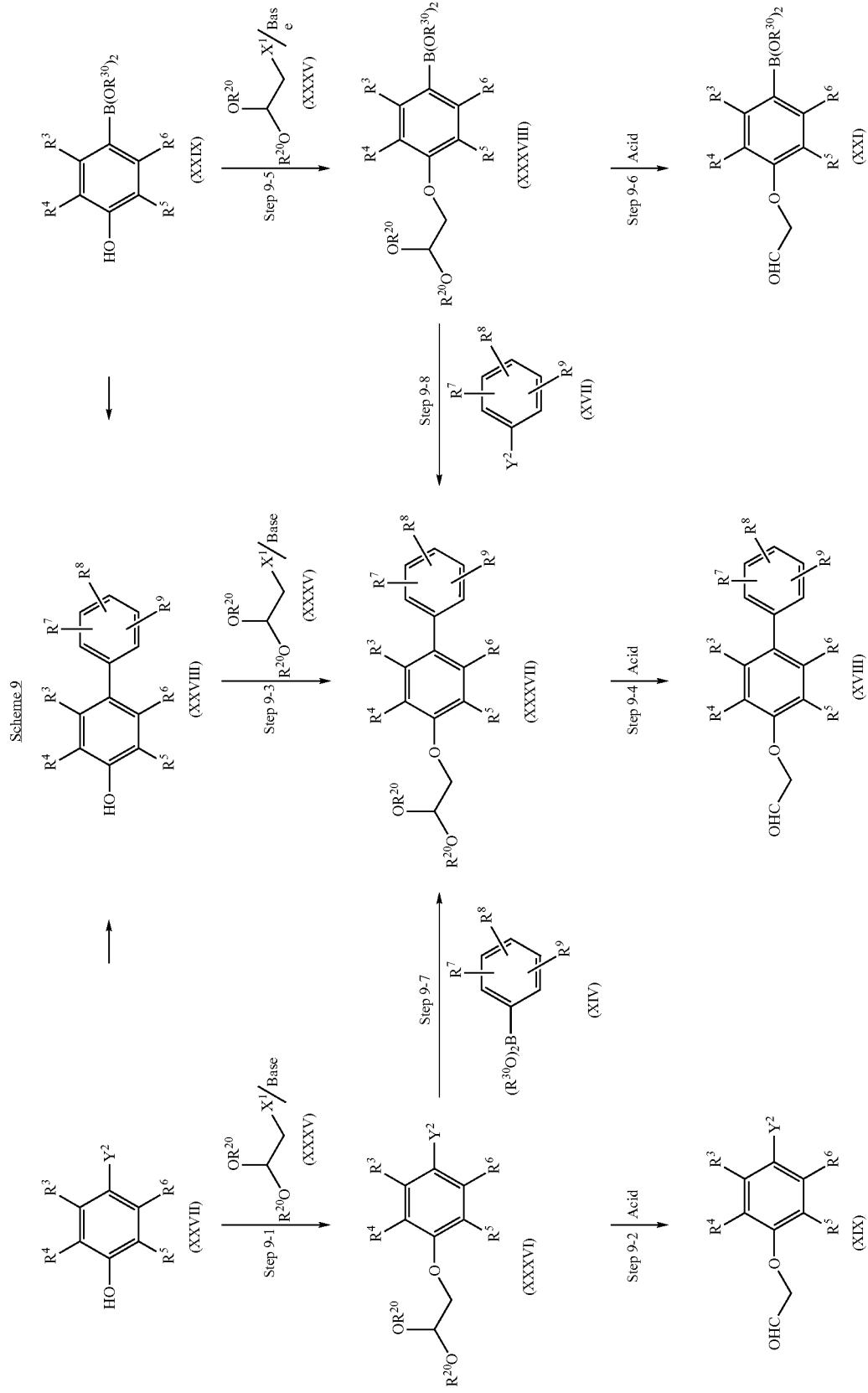

wherein $R^3$, $R^4$, $R^5$, $R^6$, $R^7$, $R^8$, $R^9$, $R^{20}$, $R^{30}$, $X^1$ and $Y^2$ are as defined above.

(Step 9-1)

Phenol derivative (XXVII) is treated with alkylating agent (XXXV) in the presence of a base such as sodium hydride, potassium carbonate, cesium carbonate or the like in an inert solvent such as N,N-dimethylformamide, acetonitrile or the like to provide an acetal derivative of general formula (XXXVI).

(Step 9-2)

Hydrolysis of the acetal derivative (XXXVI) using an acid according to conventional methods provides an aldehyde derivative of general formula (XIX).

(Steps 9-3 and 9-4)

Compound (XXVIII) is treated with alkylating agent (XXXV) according to procedures analogous to those as described in step 9-1 to afford a compound of general formula (XXXVII). The compound (XXXVII) is then hydrolyzed according to procedures analogous to those as described in step 9-2 to afford an aldehyde derivative of general formula (XVIII).

(Steps 9-5 and 9-6)

Compound (XXIX) is treated with alkylating agent (XXXV) according to procedures analogous to those as described in step 9-1 to afford a compound of general formula (XXXVIII). The compound (XXXVIII) is hydrolyzed according to procedures analogous to those as described in step 9-2 to afford an aldehyde derivative of general formula (XXI).

(Steps 9-7 and 9-8)

Alternatively, the compound (XXXVII) can be prepared by treating compound (XXXVI) with boronic acid derivative (XIV) according to procedures analogous to those as described in step 2-2. The alternate preparation of the compound (XXXVII) can be carried out by treating compound (XXXVIII) with compound (XVII) according to procedures analogous to those as described in step 2-2.

Of the starting materials employed in scheme 5, carboxylic acid derivatives (XXIII) and (XXV) can be prepared by methods as illustrated in scheme 10.

Scheme 10

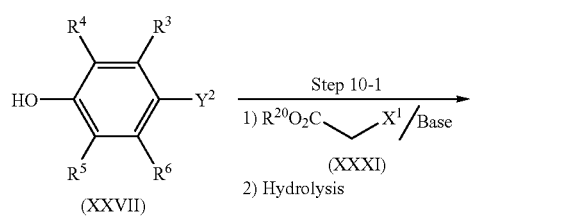

(XXVII)

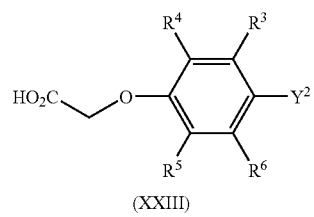

(XXIII)

-continued

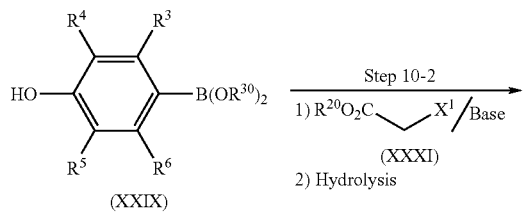

(XXIX)

(XXV)

wherein $R^3$, $R^4$, $R^5$, $R^6$, $R^{20}$, $R^{30}$, $X^1$ and $Y^2$ are as defined above.

(Step 10-1)

Phenol derivative (XXVII) is treated with compound (XXXI) in the presence of a base such as potassium carbonate, cesium carbonate or the like in an inert solvent such as N,N-dimethylformamide, acetonitrile or the like to provide a phenoxyacetic acid ester. The phenoxyacetic acid ester is then hydrolyzed according to conventional methods to afford a compound of general formula (XXIII).

(Step 10-2)

Phenol derivative (XXIX) is converted into a compound of general formula (XXV) according to procedures analogous to those as described in step 10-1.

Boronic acid derivatives (XIV) employed in schemes 2, 4 and 5 are commercially available, or can be prepared by conventional methods. For example, compounds (XIVa) and (XIVb) where $R^9$ is a lower alkoxycarbonyl or carboxy group can be prepared by methods as illustrated in scheme 11.

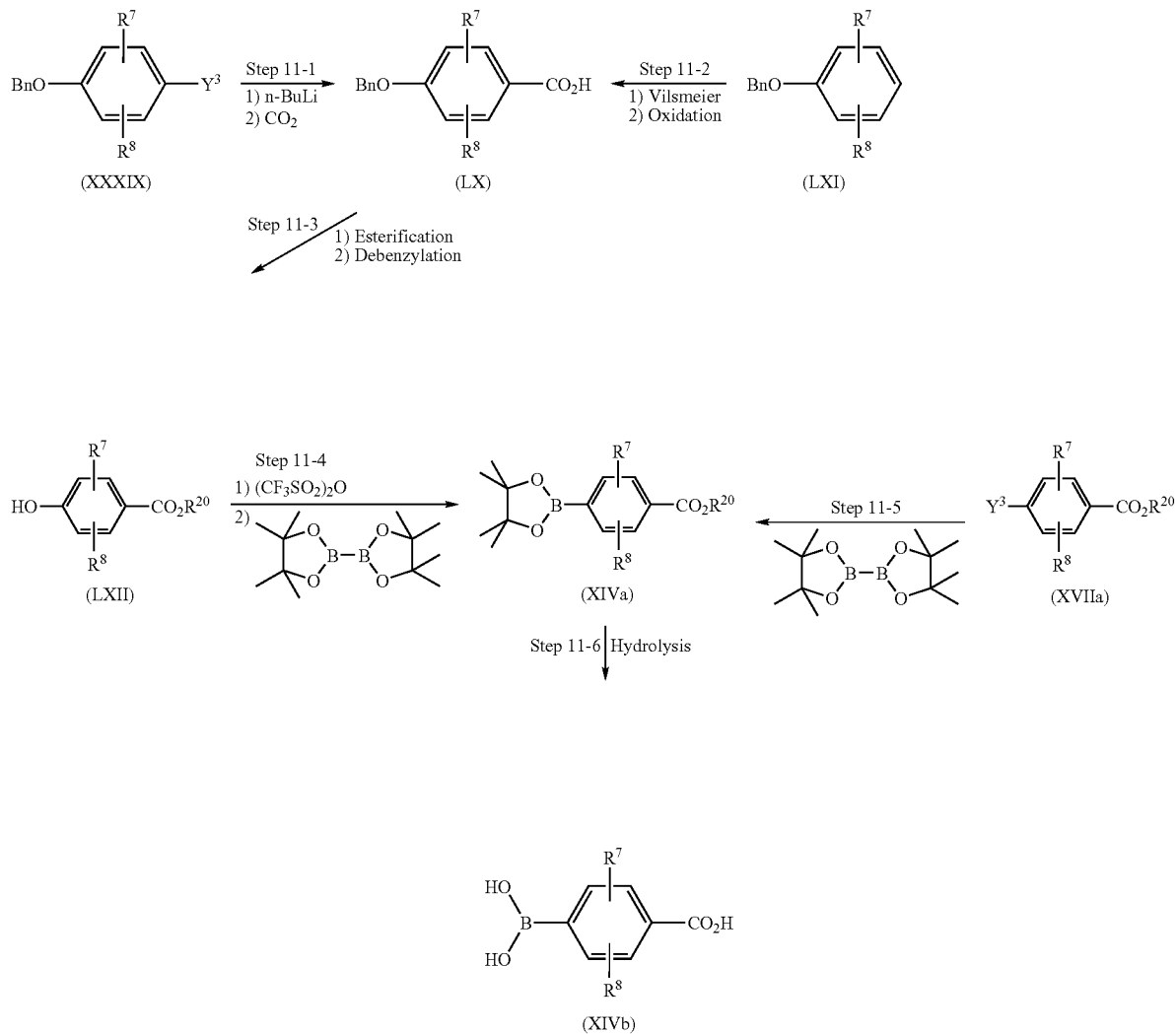

Scheme 11 wherein $R^7$, $R^8$ and $R^{20}$ are as defined above; $Y^3$ is a chlorine, bromine or iodine atom; and Bn is a benzyl group.

(Steps 11-1 to 11-3)

Lithiation of arylhalide derivative (XXXIX) according to conventional methods followed by treatment of carbon dioxide provides a benzoic acid derivative of general formula (LX).

Alternatively, the compound (LX) can be prepared from aryl derivative (LXI) by introduction of a formyl group via Vilsmeier reaction in a suitable solvent such as tert-butyl alcohol, 2-methyl-2-butene or the like, followed by oxidation using an appropriate oxidizing agent such as sodium hypochlorite or the like.

The compound (LX) is then esterified and debenzylated according to conventional methods to provide a benzoic acid ester derivative represented by general formula (LXII).

(Steps 11-4 and 11-5)

The phenolic hydroxyl group of compound (LXII) is treated with trifluoromethanesulfonic anhydride in the presence of a base such as pyridine or the like in an inert solvent such as methylene chloride or the like to provide a O-trifluoromethanesulfonyl compound.

The O-trifluoromethanesulfonyl compound is then treated with bis(pinacolato)diboron according to procedures analogous to those as described in step 2-5 to afford a compound of general formula (XIVa). The boronic ester derivative (XIVa) can also be prepared from halogenated benzoic acid derivative (XVIIa) by treatment of bis(pinacolato)diboron.

(Step 11-6)

Hydrolysis of the compound (XIVa) using an aqueous solution of alkali according to conventional methods affords a boronic acid derivative of general formula (XIVb).

Arylboronic acid ester derivatives (XXXIV) employed in schemes 7 and 8 can also be prepared by methods as illustrated in scheme 12.

Scheme 12

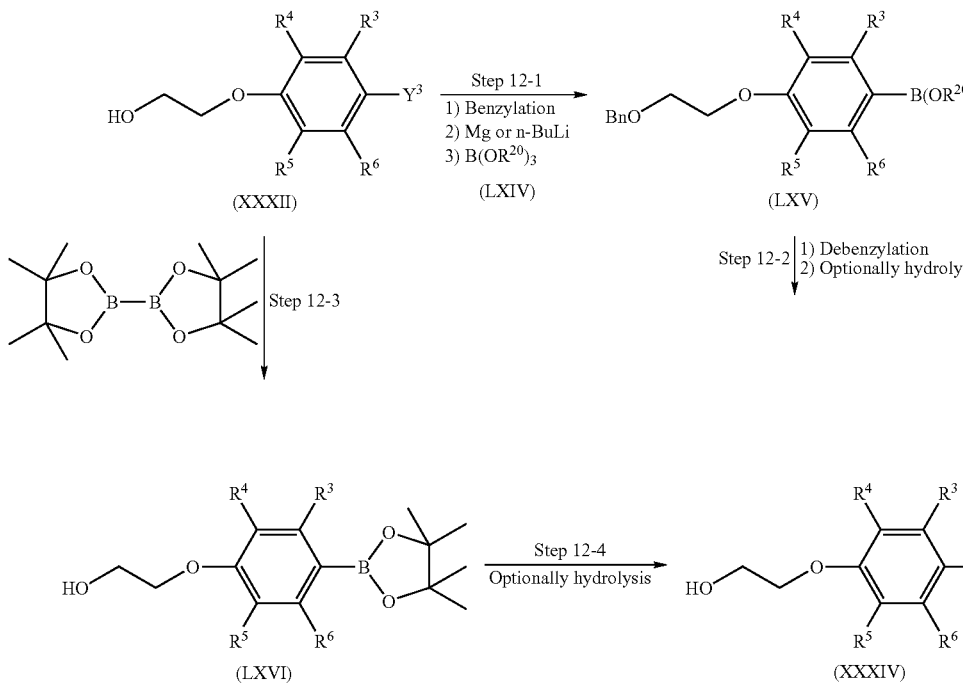

wherein $R^3$, $R^4$, $R^5$, $R^6$, $R^{20}$, $R^{30}$ and $Y^3$ are as defined above.

(Steps 12-1 and 12-2)

Compound (XXXII) is treated with a benzylhalide such as benzylbromide or the like in the presence of a base such as sodium hydride or the like to afford a O-benzylated compound. The O-benzylated compound is then converted into a Grignard reagent or lithium compound according to conventional methods, followed by treatment of boric acid ester (LXIV) to provide a compound of general formula (LXV). Removal of the benzyl group of the compound (LXV) according to conventional methods, if necessary, followed by hydrolysis provides a compound of general formula (XXIV).

(Steps 12-3 and 12-4)

Alternatively, the compound (XXXIV) can be prepared as follows. Compound (XXXII) is treated with bis(pinacolato) biboron according to procedures analogous to those as described in step 2-5 to afford a compound of general formula (LXVI). If necessary, hydrolysis of the compound (LXVI) provides compound (XXXIV).

Of halogenated benzoic acid derivatives (XVIIa) employed in scheme 11, compounds (XVIIb) where $Y^3$ is a chlorine or bromine atom can be prepared by methods as illustrated in scheme 13.

Scheme 13

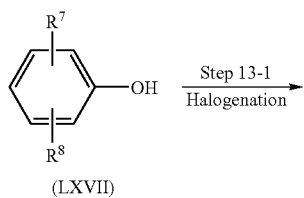

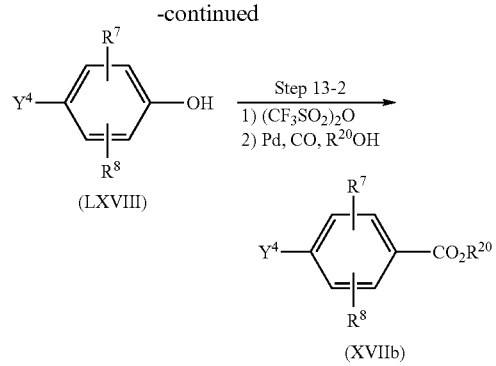

wherein $R^7$, $R^8$ and $R^{20}$ are as defined above; and $Y^4$ is a chlorine or bromine atom.

(Step 13-1)

Halogenation of phenol derivative (LXVII) using a halogenating reagent in a suitable solvent provides a compound of general formula (LXVIII). The solvents employed in the reaction include inorganic acids such as sulfuric acid or the like, organic carboxylic acids such as acetic acid or the like, halogenated hydrocarbons such as methylene chloride or the like. The halogenating reagents employed in the reaction include bromine, N-chlorosuccinimide, N-bromosuccinimide, hydrobromic acid/dimethylsulfoxide or the like.

(Step 13-2)

The compound (LXVIII) is treated with trifluoromethanesulfonic anhydride to afford a O-trifluoromethanesulfonyl compound.

The trifluoromethanesulfonyl compound is treated with carbon monoxide and $R^{20}OH$ in the presence of a phosphine ligand, palladium catalyst and base to provide a compound of general formula (XVIIb). The solvents employed in the reaction include N,N-dimethylformamide, dimethylsulfoxide or the like. The phosphine ligands include triphenylphosphine, 1,3-bis(diphenylphosphino)propane or the like. The palladium catalysts include palladium acetate or the like. The bases include triethylamine or the like.

An amino alcohol derivative of formula (X) employed in the foregoing schemes can be prepared by optically separating a commercially available enantiomeric mixture of the amino alcohol according to conventional methods. Alternatively, the amino alcohol derivative (X) can be prepared according to the procedure as described in "J. Med. Chem., 1977, 20(7), p. 978-981".

The foregoing schemes are exemplary for preparing compounds of the present invention and synthetic intermediates thereof. Those skilled in the art will appreciate that various changes or modifications of the foregoing schemes may be made without departing from the scope of the invention.

Compounds represented by general formula (I) of the present invention and intermediates for preparing the compounds of the present invention can be isolated or purified, if required, according to conventional isolation or purification techniques well known to those in the art, such as solvent extraction, crystallization, recrystallization, chromatography, preparative high performance liquid chromatography or the like.

The compounds of the present invention prepared in the above-mentioned schemes exhibit lipolytic activities and/or thermogenic activities, and are accordingly useful as a therapeutic or prophylactic agent for obesity.

The compounds of the present invention can be used, if required, in combination with antiobesity agents other than β3-adrenoceptor agonists. Examples of such antiobesity agents include anorectic agents and the like. Examples of anorectic agents include monoamine reuptake inhibitors, serotonergic agents, dopaminergic agents, neuropeptide Y antagonists, leptin or CCK-A (cholecystokinin-A) agonists. Examples of monoamine reuptake inhibitors which may be used in combination with compounds of the present invention include sibutramine, milnacipran, duloxetine, venlafaxine and the like. Examples of serotonergic agents which may be used in combination with compounds of the present invention include fenfluramine, dexfenfluramine and the like. Examples of dopaminergic agents which may be used in combination with compounds of the present invention include bromocriptine and the like. Examples of neuropeptide Y antagonists which may be used in combination with compounds of the present invention include CP-671906-01, J-115814 and the like. Examples of leptin which may be used in combination with compounds of the present invention include human recombinant leptin and the like. Examples of CCK-A agonists which may be used in combination with compounds of the present invention include GW-7178, SR-146131 and the like.

The compounds of the present invention exhibit hypoglycemic activities and insulin resistance ameliorating activities, and are accordingly useful as a therapeutic or prophylactic agent for diabetes mellitus, in particular type 2 diabetes mellitus, and diseases associated with diabetes mellitus.

The compounds of the present invention can be used, if required, in combination with antidiabetic agents other than β3-adrenoceptor agonists. Examples of such antidiabetic agents include α-glucosidase inhibitors, insulin sensitizers, insulin preparations, insulin secretion stimulants, biguanides, glucagon-like peptide 1, DPPIV inhibitors and SGLT inhibitors. Examples of α-glucosidase inhibitors which may be used in combination with compounds of the present invention include acarbose, miglitol, voglibose and the like. Examples of insulin sensitizers which may be used in combination with compounds of the present invention include pioglitazone, rosiglitazone, englitazone, darglitazone, isaglitazone, MCC-55, GI-262570, JTT-501 and the like. Examples of insulin preparations which may be used in combination with compounds of the present invention include genetically engineered human insulin, insulins extracted from bovine or swine pancreas or the like. Examples of insulin secretion stimulants which may be used in combination with compounds of the present invention include sulfonylureas such as tolbutamide, chlorpropamide, tolazamide, acetohexamide, glibenclamide, glipizide, gliclazide and the like; as well as mitiglinide (KAD-1229), nateglinide (AY-4116), glimepiride (Hoe490) and the like. Examples of biguanides which may be used in combination with compounds of the present invention include phenformin, metformin, butformin and the like. Examples of glucagon-like peptide 1 (GLP-1) include GLP-1 (1-36) amide, GLP-1 (7-36) amide, GLP-1 (7-37) and the like. Examples of DPPIV (dipeptidyl peptidase IV) inhibitors which may be used in combination with compounds of the present invention include P-32/98, NVP-DPP-728 and the like. Examples of SGLT (Na-dependent glucose cotransporter) inhibitors which may be used in combination with compounds of the present invention include compounds disclosed in WO01/16147, WO01/68660, WO01/27128, WO01/74834, WO01/74835, WO02/28872, WO02/44192, WO02/53573, WO02/64606, WO02/68439, WO02/68440, WO02/98893, EP850948, JP12/080041, JP11/21243 or JP09/188,625.

The compounds of the present invention exhibit serum cholesterol lowering activities and/or triglyceride lowering activities, and are accordingly useful as a therapeutic or prophylactic agent for hyperlipidemia.

The compounds of the present invention can be used, if required, in combination with antihyperlipidemic agents other than β3-adrenoceptor agonists. Examples of such antihyperlipidemic agents include HMG-CoA reductase inhibitors, anion exchange resins, fibrates, MTP inhibitors, CETP inhibitors, and ACAT inhibitors. Examples of HMG-CoA reductase inhibitors which may be used in combination with compounds of the present invention include pravastatin, simvastatin, fluvastatin, atorvastatin, cerivastatin, nisvastatin and the like. Examples of anion exchange resins which may be used in combination with compounds of the present invention include cholestyramine, cholestipol and the like. Examples of fibrates which may be used in combination with compounds of the present invention include bezafibrate, fenofibrate, gemfibrozii, simfibrate, ciprofibrate and clinofibrate and the like. Examples of MTP (microsomal triglyceride transfer protein) inhibitors which may be used in combination with compounds of the present invention include BMS-201038, BMS-212122, R-103757 and the like. Examples of CETP (cholesteryl ester transfer protein) inhibitors which may be used in combination with compounds of the present invention include CETi-1, JTT-705, CP-529414 and the like. Examples of ACAT (acyl-CoA:cholesterol O-acyl transferase) inhibitors which may be used in combination with compounds of the present invention include avasimibe (CI-1011), eflucimibe (F-12511) and the like.

The compounds of the present invention exhibit antidepressive activities by stimulating cerebral β3-adrenoceptors, and are accordingly useful as a therapeutic or prophylactic agent for depression.

The compounds of the present invention relaxes bladder detrusor muscle and increases the volume of bladder, and are accordingly useful as a therapeutic or prophylactic agent for urinary dysfunctions such as pollakiuria, urinary incontinence in the case of nervous pollakiuria, neurogenic bladder dysfunction, nocturia, unstable bladder, cystospasm, chronic cystitis, chronic prostatitis, prostatic hypertrophy and the like.

The compounds of the present invention can be used, if required, in combination with another medicament for the treatment of urinary dysfunctions other than β3-adrenoceptor agonists. Examples of such a medicament include anticholinergic agents, $\alpha_1$-adrenoceptor antagonists, $NK_1$ antagonists, potassium channel openers and the like. Examples of anticholinergic agents which may be used in combination with compounds of the present invention include oxybutynin, propiverin, tolterodine and the like. Examples of $\alpha_1$-adrenoceptor antagonists which may be used in combination with compounds of the present invention include tamsulosin, urapidil, naftopidil, silodsin (KMD-3213) and the like. Examples of $NK_1$ (neurokinin 1) antagonists which may be used in combination with compounds of the present invention include TAK-637 and the like. Examples of potassium channel openers which may be used in combination with compounds of the present invention include KW-7158 and the like.

The compounds of the present invention suppress intestinal motilities, and are accordingly useful as a therapeutic or prophylactic agent for diseases caused by intestinal hypermotility such as esophageal achalasia, gastritis, cholecystitis, pancreatitis, peritonitis, infectious enteritis, ulcerative colitis, Crohn's disease, irritable bowel syndrome, colon diverticulitis, simple diarrhea and the like.

Various dosage forms of pharmaceutical compositions comprising a compound represented by general formula (I) or a pharmaceutically acceptable salt thereof, can be administered depending on their usages. Exemplary dosage forms include powders, granules, fine granules, dry syrups, tablets, capsules, injections, liquids, ointments, suppositories, poultices and the like, which are administered orally or parenterally.

Pharmaceutical compositions can be formulated by admixing, diluting or dissolving with appropriate pharmaceutical additives such as excipients, disintegrators, binders, lubricants, diluents, buffers, isotonic agents, preservatives, wetting agents, emulsifying agents, dispersing agents, stabilizing agents, solubilizing agents and the like, according to a conventional formulation procedure depending upon their dosage forms.

The dosage of a compound represented by general formula (I) or a pharmaceutically acceptable salt thereof is appropriately determined depending on the age, sex or body weight of the individual patient, the severity of the disease, the condition to be treated and the like. A typical dosage for oral administration is in the range of from about 0.03 mg to about 300 mg per day per adult human. A typical dosage for parenteral administration is in the range of from about 0.003 mg to about 30 mg per day per adult human. The dosages may be administered in single or divided doses, for example one to several times daily.

A pharmaceutical combination comprising a compound represented by general formula (I) or a pharmaceutically acceptable salt thereof, and at least one selected from anti-obesity agents, antidiabetic agents, antihyperlipidemic agents, and therapeutic agents for urinary dysfunctions other than β3-adrenoceptor agonists, can be administered as a single pharmaceutical composition comprising all of active ingredients, or as separately formulated pharmaceutical compositions each of which comprises a single active ingredient. Where separately formulated pharmaceutical compositions are used, the compositions may be administered separately, concurrently or at different intervals. Alternatively, where separately formulated pharmaceutical compositions are used, the compositions may be mixed together with an appropriate diluent, and administered simultaneously.

In a pharmaceutical combination comprising a compound represented by general formula (I) or a pharmaceutically acceptable salt thereof, and at least one selected from anti-obesity agents, antidiabetic agents, antihyperlipidemic agents, and therapeutic agents for urinary dysfunctions other than β3-adrenoceptor agonists, the dosage of each active ingredient may be appropriately determined depending on the age, sex or body weight of the individual patient, the severity of the disease, administration time, dosage form, administration method, combination of active ingredients and the like.

Compounds represented by general formula (I) of the present invention exhibit potent stimulating activities on human β3-adrenoceptors. Compounds of the present invention have also good oral bioavailability. Moreover, compounds of the present invention exhibit less potent stimulating activities on β1- and/or β2-adrenoceptors than on β3-adrenoceptors. Accordingly, compounds of the present invention are suitable for the treatment or prophylaxis of obesity, diabetes mellitus, hyperlipidemia, depression, urinary dysfunctions, diseases caused by biliary calculus or biliary tract hypermotility, or diseases caused by intestinal hypermotility.

BEST MODE FOR CARRYING OUT THE INVENTION

The following examples illustrate the invention in further detail. It is to be understood, however, that they are not to be construed as limiting the scope of the invention in any way.

REFERENCE EXAMPLE 1

Benzyl 2-benzyloxy-4-(4,4,5,5-tetramethyl-1,3,2-dioxa-borolan-2-yl)benzoate

Benzyl bromide (0.80 mL) was added to a mixture of benzyl 4-benzoyloxy-2-hydoxybenzoate (2.23 g) and cesium carbonate (2.29 g) in N,N-dimethylformamide (10 mL) at room temperature. The mixture was stirred at 50° C. for 3 hrs, and water was added. The resulting mixture was extracted with ethyl acetate. The organic layer was washed with water and brine, and dried over anhydrous magnesium sulfate. The solvent was evaporated under reduced pressure, and the residue was purified by medium-pressure liquid silica gel column chromatography (eluent: n-hexane/ethyl acetate=6/1) to afford benzyl 4-benzoyloxy-2-benzyloxybenzoate (2.87 g).

A 2 mol/L aqueous solution of sodium hydroxide (6.39 mL) was added to a mixture of benzyl 4-benzoyloxy-2-benzyloxybenzoate (2.80 g), methanol (10 mL) and tetrahydrofuran (10 mL), and the mixture was stirred at room temperature for 5 hrs. 2 mol/L hydrochloric acid (6.39 mL) was added to the reaction mixture at room temperature, and the solvent was evaporated under reduced pressure. Water was added to the residue, and the mixture was extracted with ethyl acetate. The organic layer was washed with brine, and dried over anhydrous magnesium sulfate. The solvent was evaporated under reduced pressure, and the residue was purified by medium-pressure liquid silica gel column chromatography (eluent: n-hexane/ethyl acetate=4/1) to afford benzyl 2-benzyloxy-4-hydroxybenzoate (0.86 g).

Trifluoromethanesulfonic anhydride (0.22 mL) was added to an ice-cooled mixture of benzyl 2-benzyloxy-4-hydroxybenzoate (0.40 g) and pyridine (0.1 mL) in methylene chloride (1.5 mL) with stirring, and the mixture was stirred at room temperature for 30 min. The reaction mixture was poured into a mixture of hydrochloric acid and ethyl acetate, and the mixture was extracted with ethyl acetate. The organic layer was washed with water and brine, and dried over anhydrous magnesium sulfate. The solvent was evaporated under reduced pressure, and the residue was purified by medium-pressure liquid silica gel column chromatography (eluent: n-hexane/ethyl acetate=6/1) to afford benzyl 2-benzyloxy-4-trifluoromethanesulfonyloxybenzoate (0.56 g).

A mixture of benzyl 2-benzyloxy-4-trifluoromethanesulfonyloxybenzoate (0.56 g), bis(pinacolato)diboron (0.33 g), [bis(diphenylphosphino)ferrocene]dichloropalladium (0.026 g), bis(diphenylphosphino)ferrocene (0.020 g) and potassium acetate (0.35 g) in 1,4-dioxane (8 mL) was stirred at 100° C. for 12 hrs. The reaction mixture was passed through a pad of silica gel (eluent: ethyl acetate), and the filtrate was concentrated in vacuo. The residue was purified by medium-pressure liquid silica gel column chromatography (eluent: n-hexane/ethyl acetate=4/1) to afford the title compound (0.24 g).

$^1$H-NMR (CDCl$_3$) δ ppm: 1.35 (12H, s), 5.19 (2H, s), 5.33 (2H, s), 7.28-7.39 (8H, m), 7.41-7.49 (4H, m), 7.82 (1H, d, J=7.7 Hz)

REFERENCE EXAMPLE 2

2-Hydroxy-4-(4,4,5,5-tetramethyl-1,3,2-dioxaborolan-2-yl) benzoic acid

To a mixture of benzyl 2-benzyloxy-4-(4,4,5,5-tetramethyl-1,3,2-dioxaborolan-2-yl)benzoate (0.24 g), methanol (6 mL) and tetrahydrofuran (6 mL) was added 10% palladium-carbon (0.05 g) at room temperature under an atmosphere of argon. The mixture was stirred at room temperature for 3 hrs under an atmosphere of hydrogen. The catalyst was removed by filtration, and the solvent was evaporated under reduced pressure to afford the title compound (0.146 g).

$^1$H-NMR (CDCl$_3$) δ ppm: 1.37 (12H, s), 7.33 (1H, d, J=7.9 Hz), 7.45 (1H, s), 7.91 (1H, d, J=7.9 Hz), 10.40 (1H, br)

REFERENCE EXAMPLE 3

4-Bromo-2-(N,N-dimethylamino)phenol

Sodium triacetoxyborohydride (15.4 g) was added to an ice-cooled mixture of 2-amino-4-bromophenol (2.27 g) and a 37% aqueous solution of formaldehyde (9.55 mL) in acetonitrile (60 mL) with stirring. The mixture was stirred overnight at room temperature, and partitioned between water and ethyl acetate. The aqueous layer was extracted with ethyl acetate. The combined organic layer was washed with water and brine, and dried over anhydrous magnesium sulfate. The solvent was evaporated under reduced pressure, and the residue was purified by silica gel column chromatography (eluent: n-hexane/ethyl acetate=5/1) to afford the title compound (2.24 g).

$^1$H-NMR (CDCl$_3$) δ ppm: 2.64 (6H, s), 6.81 (1H, d, J=8.5 Hz), 7.15 (1H, dd, J=2.3, 8.5 Hz), 7.24 (1H, d, J=2.3 Hz)

REFERENCE EXAMPLE 4

4-Bromo-2-isopropylphenol

To a mixture of 2-isopropylphenol (3.0 g), acetic acid (30 mL) and dimethylsulfoxide (15 mL) was added dropwise 48% hydrobromic acid (15 mL) at room temperature. The mixture was stirred for 30 min, and poured into water. The resulting mixture was extracted with ethyl acetate. The organic layer was washed successively with water, a saturated aqueous solution of sodium bicarbonate and brine, and dried over anhydrous magnesium sulfate. The solvent was evaporated under reduced pressure to afford the title compound (4.62 g)

$^1$H-NMR (CDCl$_3$) δ ppm: 1.24 (6H, d, J=6.9 Hz), 3.17 (1H, septet, J=6.9 Hz), 4.83 (1H, s), 6.62 (1H, d, J=8.4 Hz), 7.15 (1H, dd, J=2.5, 8.4 Hz), 7.28 (1H, d, J=2.5 Hz)

REFERENCE EXAMPLE 5

The following compounds were prepared according to procedures analogous to those as described in Reference Example 4 by using the corresponding phenols.

4-Bromo-2-ethylphenol $^1$H-NMR (CDCl$_3$) δ ppm: 1.22 (3H, t, J=7.6 Hz), 2.60 (2H, q, J=7.6 Hz), 6.64 (1H, d, J=8.5 Hz), 7.17 (1H, dd, J=8.5, 2.5 Hz), 7.25 (1H, d, J=2.5 Hz)

4-Bromo-2-propylphenol $^1$H-NMR (CDCl$_3$) δ ppm: 0.97 (3H, t, J=7.3 Hz), 1.55-1.70 (2H, m), 2.50-2.60 (2H, m), 6.64 (1H, d, J=8.5 Hz), 7.16 (1H, dd, J=2.5, 8.5 Hz), 7.22 (1H, d, J=2.5 Hz)

4-Bromo-2-sec-butylphenol $^1$H-NMR (CDCl$_3$) δ ppm: 0.87 (3H, t, J=7.3 Hz), 1.21 (3H, d, J=6.9 Hz), 1.55-1.70 (2H, m), 2.85-2.90 (1H, m), 6.63 (1H, m), 7.15 (1H, d, J=8.5 Hz), 7.15(1H, dd, J=2.5, 8.5 Hz), 7.23 (1H, d, J=2.5 Hz)

4-Bromo-2-tert-butylphenol $^1$H-NMR (CDCl$_3$) δ ppm: 1.38 (9H, s), 4.89 (1H, br s), 6.55 (1H, d, J=8.4 Hz), 7.16 (1H, dd, J=8.4, 2.4 Hz), 7.35 (1H, d, J=2.4 Hz)

4-Bromo-2-cyclopentylphenol $^1$H-NMR (CDCl$_3$) δ ppm: 1.50-2.10 (8H, m), 3.12-3.25 (1H, m), 4.84 (1H, s), 6.64 (1H, d, J=8.5 Hz), 7.15 (1H, dd, J=2.5, 8.5 Hz), 7.28 (1H, d, J=2.5 Hz)

4-Bromo-3-ethylphenol $^1$H-NMR (CDCl$_3$) δ ppm: 1.21 (3H, t, J=7.6 Hz), 2.69 (2H, q, J=7.6 Hz), 4.85 (1H, brs), 6.55 (1H, dd, J=8.6, 3.0 Hz), 6.73 (1H, d, J=3.0 Hz), 7.35 (1H, d, J=8.6 Hz)

4-Bromo-3-propylphenol $^1$H-NMR (CDCl$_3$) δ ppm: 0.98 (3H, t, J=7.4 Hz), 1.58-1.69 (2H, m), 2.61-2.66 (2H, m), 6.55 (1H, dd, J=8.6, 3.0 Hz), 6.71 (1H, d, J=3.0 Hz), 7.35 (1H, d, J=8.6 Hz)

4-Bromo-3-isopropylphenol $^1$H-NMR (CDCl$_3$) δ ppm: 1.21 (6H, d, J=6.9 Hz), 3.30 (1H, septet, J=6.9 Hz), 4.86 (1H, br s), 6.55 (1H, dd, J=8.6, 3.0 Hz), 6.77 (1H, d, J=3.0 Hz), 7.36 (1H, d, J=8.6 Hz)

REFERENCE EXAMPLE 6

Methyl 4-bromo-2-isopropylbenzoate

Trifluoromethanesulfonic anhydride (0.47 mL) was added to an ice-cooled mixture of 4-bromo-2-isopropylphenol (0.5 g) and pyridine (0.28 mL) in methylene chloride (5 mL) with stirring. The mixture was stirred for 10 min, and poured into a mixture of ethyl acetate and 1 mol/L hydrochloric acid. The organic layer was separated, washed with water and brine, and dried over anhydrous magnesium sulfate. The solvent was evaporated under reduced pressure, and the residue was purified by silica gel column chromatography (eluent: diethyl ether/n-hexane=1/10) to afford 4-bromo-2-isopropylphenyl methanesulfonate (0.71 g).

A mixture of 4-bromo-2-isopropylphenyl methanesulfonate (0.71 g), palladium acetate (0.023 g), 1,3-bis(diphenylphosphino)propane (0.042 g) and triethylamine (0.63 mL) in methanol (6 mL)/dimethylsulfoxide (9 mL) was stirred overnight at 55° C. under an atmosphere of carbon monoxide. Water and ethyl acetate were added to the reaction mixture. The organic layer was separated, washed with water and brine, and dried over anhydrous magnesium sulfate. The solvent was evaporated under reduced pressure, and the residue was purified by silica gel column chromatography (eluent: diethyl ether/n-hexane=1/10) to afford the title compound (0.355 g).

$^1$H-NMR (CDCl$_3$) δ ppm: 1.24 (6H, d, J=6.6 Hz), 3.65-3.80 (1H, m), 3.88 (3H, s), 7.35 (1H, dd, J=8.2, 2.0 Hz), 7.53 (1H, d, J=2.0 Hz), 7.61 (1H, d, J=8.2 Hz)

REFERNCE EXAMPLE 7

4-Bromo-2-isopropylbenzoic acid

A mixture of methyl 4-bromo-2-isopropylbenzoate (0.41 g) and lithium hydroxide monohydrate (0.67 g) in water (1 mL)/1,4-dioxane (3 mL) was stirred at room temperature for 5 days. 2 mol/L hydrochloric acid (10 mL) was added to the mixture, and the resulting mixture was extracted with ethyl acetate. The solvent was evaporated under reduced pressure, and the residue was recrystallized from ethyl acetate/n-hexane to afford the title compound (0.276 g).

$^1$H-NMR (DMSO-d$_6$) δ ppm: 1.19 (6H, d, J=6.9 Hz), 3.69 (1H, septet, J=6.9 Hz), 7.47 (1H, dd, J=2.1, 8.3 Hz), 7.58-7.61 (2H, m), 13.10 (1H, br s)

REFERENCE EXAMPLE 8

The following compounds were prepared according to procedures analogous to those as described in Reference Examples 6 and 7 by using the corresponding bromophenols.

4-Bromo-2-ethylbenzoic acid

H-NMR (CDCl$_3$) δ ppm: 1.26 (3H, t, J=7.4 Hz), 3.03 (2H, q, J=7.4 Hz), 7.42 (1H, dd, J=8.6, 2.0 Hz), 7.47 (1H, d, J=2.0 Hz), 7.89 (1H, d, J=8.6 Hz), 11.0 (1H, br)

4-Bromo-2-propylbenzoic acid $^1$H-NMR (CDCl$_3$) δ ppm: 0.99 (3H, t, J=7.2 Hz), 1.60-1.70 (2H, m), 2.95-3.05 (2H, m), 7.42 (1H, dd, J=8.3, 2.0 Hz), 7.45 (1H, d, J=2.0 Hz), 7.89 (1H, d, J=8.3 Hz), 11.0 (1H, br)

4-Bromo-2-sec-butylbenzoic acid $^1$H-NMR (CDCl$_3$) δ ppm: 0.86 (3H, t, J=7.3 Hz), 1.25 (3H, d, J=6.7 Hz), 1.55-1.70 (2H, m), 3.65-3.75 (1H, m), 7.40 (1H, dd, J=8.5, 1.9 Hz), 7.52 (1H, d, J=1.9 Hz), 7.80 (1H, d, J=8.5 Hz), 11.5 (1H, br)

4-Bromo-2-tert-butylbenzoic acid $^1$H-NMR (CDCl$_3$) δ ppm: 1.46 (9H, s), 7.35-7.45 (2H, m), 7.66 (1H, d, J=1.7 Hz), 10.5 (1H, br)

4-Bromo-2-cyclopentylbenzoic acid $^1$H-NMR (DMSO-d$_6$)$_6$ ppm: 1.45-1.68 (4H, m), 1.70-1.85 (2H, m), 1.93-2.05 (2H, m), 3.62-3.72 (1H, m), 7.46 (1H, dd, J=2.0, 8.4 Hz), 7.55-7.60 (2H, m), 13.12 (1H, br)

4-Bromo-2-(N,N-dimethylamino)benzoic acid $^1$H-NMR (DMSO-d$_6$) δ ppm: 2.81 (6H, s), 7.32 (1H, dd, J=1.9, 8.4 Hz), 7.62 (1H, d, J=1.9 Hz), 7.70 (1H, d, J=8.4 Hz), 15.55 (1H, br)

2-Acetyl-4-bromobenzoic acid $^1$H-NMR (CDCl$_3$) ppm: 1.90 (3H, s), 7.70-7.77 (3H, m)

4-Bromo-3-ethylbenzoic acid $^1$H-NMR (CDCl$_3$) δ ppm: 1.27 (3H, t, J=7.5 Hz), 2.82 (2H, q, J=7.5 Hz), 7.64 (1H, d, J=8.2 Hz), 7.77 (1H, dd, J=8.2, 2.3 Hz), 7.97 (1H, d, J=2.3 Hz), 11.5 (1H, br)

4-Bromo-3-propylbenzoic acid $^1$H-NMR (CDCl$_3$) δ ppm: 1.00 (3H, t, J=7.4 Hz), 1.65-1.75 (2H, m), 2.75-2.80 (2H, m), 7.64 (1H, d, J=8.4 Hz), 7.76 (1H, dd, J=8.4, 2.1 Hz), 7.94 (1H, d, J=2.1 Hz), 11.0 (1H, br)

4-Bromo-3-isopropylbenzoic acid $^1$H-NMR (CDCl$_3$) δ ppm: 1.29 (6H, d, J=6.8 Hz), 3.35-3.45 (1H, m), 7.65 (1H, d, J=8.3 Hz), 7.76 (1H, dd, J=8.3, 2.3 Hz), 8.01 (1H, d, J=2.3 Hz), 11.0 (1H, br)

4-Bromo-2-methylsulfanylbenzoic acid $^1$H-NMR (CDCl$_3$) δ ppm: 2.47 (3H, s), 7.32 (1H, dd, J=8.4, 1.8 Hz), 7.39 (1H, d, J=1.8 Hz), 7.98 (1H, d, J=8.4 Hz)

REFERENCE EXAMPLE 9

Methyl 4-benzyloxy-2-ethoxybenzoate

Ethyl iodide (0.14 mL) was added to a mixture of methyl 4-benzyloxy-2-hydroxybenzoate (0.30 g) and potassium carbonate (0.32 g) in N,N-dimethylformamide (2.9 mL) at room temperature with stirring. The mixture was stirred at that temperature for 1.6 hrs and at 50° C. for 1.4 hrs. Water was added, and the resulting mixture was extracted with ethyl acetate. The organic layer was washed with water, and dried over anhydrous magnesium sulfate. The solvent was evaporated under reduced pressure to afford the title compound (0.29 g).

$^1$H-NMR (CDCl$_3$) δ ppm: 1.45 (3H, t, J=6.9 Hz), 3.85 (3H, s), 4.07 (2H, q, J=6.9 Hz), 5.09 (2H, s), 6.50-6.60 (2H, m), 7.30-7.50 (5H, m), 7.83 (1H, dd, J=0.9, 7.9 Hz)

REFERENCE EXAMPLE 10

The following compounds were prepared according to procedures analogous to those as described in Reference Example 9 by using the corresponding alkyl halides.

Methyl 4-benzyloxy-2-methoxybenzoate $^1$H-NMR (CDCl$_3$) δ ppm: 3.83 (3H, s), 3.84 (3H, s), 5.07 (2H, s), 6.50-6.60 (2H, m), 7.25-7.45 (5H, m), 7.80-7.85 (1H, m)

Methyl 4-benzyloxy-2-isopropoxybenzoate $^1$H-NMR (CDCl$_3$) δ ppm: 1.35 (6H, d, J=6.0 Hz), 3.84 (3H, s), 4.52 (1H, septet, J=6.0 Hz), 5.09 (2H, s), 6.50-6.60 (2H, m), 7.30-7.45 (5H, m), 7.75-7.85 (1H, m)

REFERENCE EXAMPLE 11

Methyl 4-hydroxy-2-methoxybenzoate

To a solution of methyl 4-benzyloxy-2-methoxybenzoate (3.08 g) in methanol (5 mL)/tetrahydrofuran (7.5 mL) was added 10% palladium-carbon (0.3 g) at room temperature under an atmosphere of argon, and the mixture was stirred at that temperature for 2 hrs under an atmosphere of hydrogen. The catalyst was removed by filtration, and the filtrate was concentrated in vacuo to afford the title compound (2.02 g).

$^1$H-NMR (CDCl$_3$) δ ppm: 3.84 (3H, s), 3.86 (3H, s), 6.41 (1H, dd, J=2.2, 8.5 Hz), 6.44 (1H, d, J=2.2 Hz), 7.77 (1H, d, J=8.5 Hz)

REFERENCE EXAMPLE 12

The following compounds were prepared according to procedures analogous to those as described in Reference Example 11 by using the corresponding benzylethers.

Methyl 2-ethoxy-4-hydroxybenzoate $^1$H-NMR (CDCl$_3$) δ ppm: 1.47 (3H, t, J=7.3 Hz), 3.84 (3H, s), 4.08 (2H, q, J=7.3 Hz), 5.13-5.16 (1H, m), 6.39 (1H, dd, J=2.4, 8.5 Hz), 6.43 (1H, d, J=2.4 Hz), 7.78 (1H, d, J=8.5 Hz)

Methyl 4-hydroxy-2-isopropoxybenzoate $^1$H-NMR (CDCl$_3$) δ ppm: 1.37 (6H, d, J=6.0 Hz), 3.84 (3H, s), 4.52 (1H, septet, J=6.0 Hz), 6.35-6.50 (2H, m), 7.70-7.80 (1H, m)

REFERENCE EXAMPLE 13

2-Methoxy-4-trifluoromethanesulfonyloxybenzoic acid

Trifluoromethanesulfonic anhydride (2.24 mL) was added to an ice-cooled mixture of methyl 4-hydroxy-2-methoxybenzoate (2.02 g) and pyridine (0.14 mL) in methylene chloride (15 mL) with stirring. The mixture was stirred at room temperature for 30 min, and poured into a mixture of hydrochloric acid and ethyl acetate. The resulting mixture was extracted with ethyl acetate. The organic layer was washed with water and brine, and dried over anhydrous magnesium sulfate. The solvent was evaporated under reduced pressure to afford methyl 2-methoxy-4-trifluoromethanesulfonyloxybenzoate (3.49 g).

A mixture of methyl 2-methoxy-4-trifluoromethanesulfonyloxybenzoate (3.49 g), sulfuric acid (90%, 0.1 mL), acetic acid (10 mL) and water (2 mL) was heated under reflux for 16 hrs. The reaction mixture was diluted with water, and the mixture was extracted with ethyl acetate. The organic layer was washed with water and brine, and dried over anhydrous magnesium sulfate. The solvent was evaporated under reduced pressure. The residue was purified by recrystallization (solvent: ethyl acetate/n-hexane) to afford the title compound (1.25 g).

$^1$H-NMR (CDCl$_3$) δ ppm: 4.12 (3H, s), 6.98 (1H, d, J=2.5 Hz), 7.07 (1H, dd, J=2.5, 8.7 Hz), 8.29 (1H, d, J=8.7 Hz)

REFERENCE EXAMPLE 14

The following compounds were prepared according to procedures analogous to those as described in Reference Example 13 by using the corresponding phenol derivatives.

2-Ethoxy-4-trifluoromethanesulfonyloxybenzoic acid $^1$H-NMR (CDCl$_3$) δ ppm: 1.61 (3H, t, J=6.9 Hz), 4.37 (2H, q, J=6.9 Hz), 6.97 (1H, d, J=2.2 Hz), 7.06 (1H, dd, J=2.2, 8.8 Hz), 8.31 (1H, d, J=8.8 Hz)

2-Isopropoxy-4-trifluoromethanesulfonyloxybenzoic acid $^1$H-NMR (CDCl$_3$) δ ppm: 1.53 (6H, d, J=6.0 Hz), 4.86 (1H, septet, J=6.0 Hz), 6.97 (1H, d, J=2.2 Hz), 7.04 (1H, dd, J=2.2, 8.8 Hz), 8.30 (1H, d, J=8.8 Hz)

REFERENCE EXAMPLE 15

The following compounds were prepared according to procedures analogous to those as described in Reference Example 9 by using ethyl 3-hydroxy-4-iodobenzoate and the corresponding alkyl halides.

Ethyl 3-ethoxy-4-iodobenzoate $^1$H-NMR (CDCl$_3$) δ ppm: 1.39 (3H, t, J=7.2 Hz), 1.50 (3H, t, J=6.9 Hz), 4.16 (2H, q, J=6.9 Hz), 4.37 (2H, q, J=7.2 Hz), 7.36 (1H, dd, J=8.0, 1.6 Hz), 7.42 (1H, d, J=1.6 Hz), 7.84 (1H, d, J=8.0 Hz)

Ethyl 4-iodo-3-isopropoxybenzoate $^1$H-NMR (CDCl$_3$) δ ppm: 1.35-1.45 (9H, m), 4.37 (2H, q, J=7.1 Hz), 4.60-4.75 (1H, m), 7.34 (1H, dd, J=8.1, 1.8 Hz), 7.44 (1H, d, J=1.8 Hz), 7.84 (1H, d, J=8.1 Hz)

Ethyl 4-iodo-3-propoxybenzoate $^1$H-NMR (CDCl$_3$) δ ppm: 1.11 (3H, t, J=7.4 Hz), 1.39 (3H, t, J=7.1 Hz), 1.80-1.95 (2H, m), 4.05 (2H, t, J=6.4 Hz), 4.37 (2H, q, J=7.1 Hz), 7.35 (1H, dd, J=8.1, 1.8 Hz), 7.42 (1H, d, J=1.8 Hz), 7.84 (1H, d, J=8.1 Hz)

REFERENCE EXAMPLE 16

Methyl 2,5-dimethyl-4-trifluoromethanesulfonyloxybenzoate

A mixture of 4-iodo-2,5-dimethylphenol (1.0 g), palladium acetate (0.045 g), 1,3-bis(diphenylphosphino)propane (0.083 g), triethylamine (0.90 mL), methanol (20 mL) and dimethylsulfoxide (30 mL) was stirred at 60° C. overnight under an atmosphere of carbon monooxide. The insoluble materials were removed by filtration, and the filtrate was concentrated in vacuo. The residue was partitioned between ethyl acetate and water. The organic layer was washed with water and brine, and dried over anhydrous magnesium sulfate. The solvent was evaporated under reduced pressure, and the residue was purified by silica gel column chromatography (eluent:n-hexane/ethyl acetate=10/1-3/1) to afford methyl 4-hydroxy-2,5-dimethylbenzoate (0.16 g).

$^1$H-NMR (CDCl$_3$) δ ppm: 2.23 (3H, s), 2.53 (3H, s), 3.85 (3H, s), 4.94 (1H, br s), 6.62 (1H, s), 7.77 (1H, s)

Trifluoromethanesulfonic anhydride (0.27 g) was added to an ice-cooled mixture of methyl 4-hydroxy-2,5-dimethylbenzoate (0.144 g) and pyridine (0.095 g) in methylene chloride (10 mL) with stirring. The mixture was stirred at room temperature for 30 min, and poured into a mixture of ethylacetate and 2 mol/L hydrochloric acid. The organic layer was separated, washed with water and brine, and dried over anhydrous magnesium sulfate. The solvent was evaporated under reduced pressure, and the residue was purified by silica gel column chromatography (eluent:n-hexane:ethyl acetate=10/1) to afford the title compound (0.226 g).

$^1$H-NMR (CDCl$_3$) δ ppm: 2.36 (3H, s), 2.58 (3H, s), 3.90 (3H, s), 7.12 (1H, s), 7.87 (1H, s)

REFERENCE EXAMPLE 17

Ethyl 3-methoxy-4-(4,4,5,5-tetramethyl-1,3,2-dioxaborolan-2-yl)benzoate

Trifluoromethanesulfonic anhydride (0.94 mL) was added to an ice-cooled mixture of ethyl vanillate (1.0 g) and pyridine (0.45 mL) in methylene chloride (5 mL) with stirring. The mixture was stirred for 10 min, and poured into a mixture of 1 mol/L hydrochloric acid and ethyl acetate. The organic layer was separated, washed with water and brine, and dried over anhydrous magnesium sulfate. The solvent was evaporated under reduced pressure, and the residue was purified by silica gel column chromatography (eluent:ethyl acetate/n-hexane=1/10) to afford ethyl 3-methoxy-4-trifluoromethanesulfonyloxybenzoate (1.47 g).

A mixture of ethyl 3-methoxy-4-trifluoromethanesulfonyloxybenzoate (0.66 g), bis(pinacolato)diboron (0.56 g), [bis(diphenylphosphino)ferrocene]dichloropalladium (0.044 g), bis (diphenylphosphino) ferrocene (0.033 g) and potassium acetate (0.59 g) in 1,4-dioxane (4 mL) was stirred at 80° C. for 24 hrs. The reaction mixture was poured into water, and the resulting mixture was extracted with ethyl acetate. The organic layer was washed with water and brine, and dried over anhydrous magnesium sulfate. The solvent was evaporated under reduced pressure, and the residue was purified by silica gel column chromatography (eluent:ethyl acetate/n-hexane=1/5) to afford the title compound (0.079 g).

$^1$H-NMR (CDCl$_3$) δ ppm: 1.36 (12H, s), 1.40 (3H, t, J=7.1 Hz), 3.89 (3H, s), 4.38 (2H, q, J=7.1 Hz), 7.50 (1H, d, J=1.3 Hz), 7.60 (1H, dd, J=1.3, 7.6 Hz), 7.69 (1H, d, J=7.6 Hz)

REFERENCE EXAMPLE 18

4-Carboxy-2-methoxyphenylboronic acid

Sodium metaperiodate (0.157 g) was added to a mixture of ethyl 3-methoxy-4-(4,4,5,5-tetramethyl-1,3,2-dioxaborolan-2-yl)benzoate (0.075 g), water (1 mL) and tetrahydrofuran (4 mL) at room temperature with stirring, and the mixture was stirred at that temperature for 10 min. 2 mol/L hydrochloric acid (0.082 mL) was added, and the resulting mixture was stirred at that temperature for additional 2 hrs, then water and ethyl acetate were added. The organic layer was separated, washed with water and brine, and dried over anhydrous magnesium sulfate. The solvent was evaporated under reduced pressure to afford 4-ethoxycarbonyl-2-methoxyphenylboronic acid (0.049 g).

Lithium hydroxide monohydrate (0.092 g) was added to a mixture of 4-ethoxycarbonyl-2-methoxyphenylboronic acid (0.049 g), water (1 mL) and 1,4-dioxane (1 mL), and the mixture was stirred at room temperature overnight. 2 mol/L hydrochloric acid (1.09 mL) was added to the reaction mixture, and the solvent was evaporated under reduced pressure. The residue was washed with water to afford the title compound (0.035 g).

$^1$H-NMR (DMSO-d$_6$) δ ppm: 3.84 (3H, s), 7.44 (1H, d, J=1.2 Hz), 7.51 (1H, dd, J=1.2, 7.5 Hz), 7.58 (1H, d, J=7.5 Hz), 7.91 (2H, s), 12.93 (1H, br)

REFERENCE EXAMPLE 19

Methyl 2-isopropyl-4-(4,4,5,5-tetramethyl-1,3,2-dioxaborolan-2-yl)benzoate

The title compound was prepared according to procedures analogous to those as described in Reference Example 17 by using methyl 4-bromo-2-isopropylbenzoate instead of ethyl 3-methoxy-4-trifluoromethanesulfonyloxybenzoate which was an intermediate in Reference Example 17.

$^1$H-NMR (CDCl$_3$) δ ppm: 1.28 (6H, d, J=6.6 Hz), 1.35 (12H, s), 3.55-3.70 (1H, m), 3.89 (3H, s), 7.60-7.70 (2H, m), 7.82 (1H, s)

REFERENCE EXAMPLE 20

(2-Acetyl-4-bromophenoxy)acetic acid

Ethyl bromoacetate (0.62 mL) was added to a mixture of 5-bromo-2-hydroxyacetophenone (1.0 g) and potassium carbonate (0.96 g) in N,N-dimethylformamide (10 mL) at room temperature with stirring, and the mixture was stirred at that temperature overnight. Water and ethyl acetate were added to the reaction mixture. The organic layer was separated, washed with water and brine, and dried over anhydrous magnesium sulfate. The solvent was evaporated under reduced pressure to afford ethyl (2-acetyl-4-bromophenoxy)acetate as a crude product.

The crude ethyl (2-acetyl-4-bromophenoxy)acetate was dissolved in ethanol (5 mL). A 2 mol/L aqueous solution of sodium hydroxide (5 mL) was added to the solution, and the mixture was stirred at room temperature for 1 hr. The reaction mixture was made acidic with the addition of 2 mol/L hydrochloric acid (7 mL), and then ethyl acetate and brine were added. The organic layer was separated, washed with water and brine, and dried over anhydrous magnesium sulfate. The solvent was evaporated under reduced pressure, and the residue was recrystallized from ethyl acetate and n-hexane to afford the title compound (0.85 g).

¹H-NMR (CDCl₃) δ ppm: 2.67 (3H, s), 4.75 (2H, s), 6.85 (1H, d, J=8.9 Hz), 7.62 (1H, dd, J=2.5, 8.9 Hz), 7.89 (1H, d, J=2.5 Hz)

REFERENCE EXAMPLE 21

(4-Bromo-2-hydroxymethylphenoxy)acetic acid

The title compound was prepared according to procedures analogous to those as described in Reference Example 20 by using 4-bromo-2-hydroxymethylphenol.

¹H-NMR (DMSO-d₆) δ ppm: 4.52 (2H, s), 4.70 (2H, s), 6.83 (1H, d, J=8.7 Hz), 7.34 (1H, dd, J=2.6, 8.7 Hz), 7.49 (1H, d, J=2.6 Hz)

REFERENCE EXAMPLE 22

[2-Isopropyl-4-(4,4,5,5-tetramethyl-1,3,2-dioxaborolan-2-yl)phenoxy]acetic acid

Benzyl bromoacetate (0.88 mL) was added to a mixture of 4-bromo-2-isopropylphenol (1.0 g) and potassium carbonate (0.96 g) in N,N-dimethylformamide (5 mL), and the mixture was stirred at room temperature overnight. Water and ethyl acetate were added to the reaction mixture. The organic layer was separated, washed with water and brine, and dried over anhydrous magnesium sulfate. The solvent was evaporated under reduced pressure, and the residue was purified by silica gel column chromatography (eluent: diethyl ether/n-hexane=1/10) to afford benzyl (4-bromo-2-isopropylphenoxy) acetate (1.70 g).

A mixture of benzyl (4-bromo-2-isopropylphenoxy)acetate (0.25 g), bis(pinacolato)diboron (0.19 g), [bis(diphenylphosphino)ferrocene]dichloropalladium (0.015 g), bis (diphenylphosphino)ferrocene (0.011 g) and potassium acetate (0.20 g) in 1,4-dioxane (4 mL) was stirred at 100° C. for 24 hrs. The reaction mixture was diluted with diethyl ether, and the insoluble materials were removed by filtration. The solvent was evaporated under reduced pressure, and the residue was purified by silica gel column chromatography (eluent: n-hexane/ethyl acetate=3/1) to afford benzyl [2-isopropyl-4-(4,4,5,5-tetramethyl-1,3,2-dioxaborolan-2-yl)phenoxy]acetate (0.24 g).

A mixture of benzyl [2-isopropyl-4-(4,4,5,5-tetramethyl-1,3,2-dioxaborolan-2-yl)phenoxy]acetate (0.24 g) and 10% palladium-carbon (0.05 g) in ethanol (10 mL) was stirred at room temperature for 2 hrs under an atmosphere of hydrogen. The catalyst was removed by filtration, and the solvent was evaporated under reduced pressure to afford the title compound (0.156 g).

¹H-NMR (CD₃OD) δ ppm: 1.23 (6H, d, J=7.1 Hz), 1.33 (12H, s), 3.35-3.45 (1H, m), 4.70 (2H, s), 6.79 (1H, d, J=8.3 Hz), 7.53 (1H, dd, J=1.5, 8.3 Hz), 7.61 (1H, d, J=1.5 Hz)

REFERENCE EXAMPLE 23

[3-Methyl-4-(4,4,5,5-tetramethyl-1,3,2-dioxaborolan-2-yl)phenoxy]acetic acid

The title compound was prepared according to procedures analogous to those as described in Reference Example 22 by using 4-bromo-3-methylphenol.

¹H-NMR (DMSO-d₆) ppm: 1.28 (12H, s), 2.42 (3H, s), 4.67 (2H, s), 6.69 (1H, dd, J=1.4, 8.2 Hz), 6.72 (1H, d, J=1.4 Hz), 7.55 (1H, d, J=8.2 Hz), 12.94 (1H, br s)

REFERENCE EXAMPLE 24

4-Carboxymethoxy-3-ethoxyphenylboronic acid

Ethyl bromoacetate (1.04 mL) was added to a mixture of 4-bromo-2-ethoxyphenol (1.69 g) and potassium acetate (1.62 g) in N,N-dimethylformamide (10 mL), and the mixture was stirred at room temperature overnight. Water and ethyl acetate were added to the reaction mixture. The organic layer was separated, washed with water and brine, and dried over anhydrous magnesium sulfate. The solvent was evaporated under reduced pressure, and the residue was purified by silica gel column chromatography (eluent:diethyl ether/n-hexane=1/10) to afford ethyl (4-bromo-2-ethoxyphenoxy)acetate (2.26 g).

A mixture of ethyl (4-bromo-2-ethoxyphenoxy)acetate (2.26 g), bis(pinacolato)diboron (2.08 g), [bis(diphenylphosphino) ferrocene]dichloropalladium (0.16 g), bis(diphenylphosphino)ferrocene (0.12 g) and potassium acetate (2.20 g) in 1,4-dioxane (10 mL) was stirred at 100° C. for 24 hrs. The reaction mixture was diluted with diethyl ether, and the insoluble materials were removed by filtration. The solvent was evaporated under reduced pressure, and the residue was purified by silica gel column chromatography (eluent:n-hexane/ethyl acetate=10/1-5/1) to afford ethyl [2-ethoxy-4-(4,4,5,5-tetramethyl-1,3,2-dioxaborolan-2-yl)phenoxy]acetate (2.28 g)

A 2 mol/L aqueous solution of sodium hydroxide (2.14 mL) was added to a solution of ethyl [2-ethoxy-4-(4,4,5,5-tetramethyl-1,3,2-dioxaborolan-2-yl)phenoxy]acetate (0.15 g) in ethanol (10 mL), and the resulting mixture was stirred at 60° C. for 3 hrs. Water and ethyl acetate were added to the reaction mixture. The aqueous layer was separated, washed with ethyl acetate, made acidic with the addition of 2 mol/L hydrochloric acid, and extracted with ethyl acetate. The organic layer was dried over anhydrous magnesium sulfate. The solvent was evaporated under reduced pressure to afford the title compound (0.066 g).

¹H-NMR (DMSO-d₆) δ ppm: 1.20-1.40 (3H, m), 3.95-4.15 (2H, m), 4.60-4.75 (2H, m), 6.75-7.45 (3H, m), 12.91 (1H, br)

REFERENCE EXAMPLE 25

Ethyl (4-bromo-2,6-dimethylphenoxy)acetate

Ethyl bromoacetate (0.66 mL) was added to a mixture of 4-bromo-2,6-dimethylphenol (1.0 g) and potassium acetate (1.03 g) in N,N-dimethylformamide (10 mL), and stirred at 80° C. for 3 hrs. Water and ethyl acetate were added to the reaction mixture. The organic layer was separated, washed with water and brine, and dried over anhydrous magnesium sulfate. The solvent was evaporated under reduced pressure, and the residue was purified by silica gel column chromatography (elent:ethyl acetate/n-hexane=1/10) to afford the title compound (1.29 g).

¹H-NMR (CDCl₃) δ ppm: 1.33 (3H, t, J=7.2 Hz), 2.27 (6H, s), 4.30 (2H, q, J=7.2 Hz), 4.36 (2H, s), 7.14 (2H, s)

REFERENCE EXAMPLE 26

The following compounds were prepared according to procedures analogous to those as described in Reference Example 25 by using the corresponding phenol derivatives.

Ethyl (4-bromo-2-methylphenoxy)acetate

¹H-NMR (CDCl₃) δ ppm: 1.20 (3H, t, J=7.1 Hz), 2.18 (3H, s), 4.16 (2H, q, J=7.1 Hz), 4.80 (2H, s), 6.82 (1H, d, J=9.1 Hz), 7.20-7.40 (2H, m)

Ethyl (4-bromo-2-chlorophenoxy)acetate $^1$H-NMR (CDCl$_3$) δ ppm: 1.21 (3H, t, J=7.1 Hz), 4.17 (2H, q, J=7.1 Hz), 4.93 (2H, s), 7.04 (1H, d, J=8.9 Hz), 7.42-7.50 (1H, m), 7.69 (1H, d, J=2.2 Hz)

Ethyl (4-bromo-2-fluorophenoxy)acetate $^1$H-NMR (CDCl$_3$) δ ppm: 1.21 (3H, t, J=7.1 Hz), 4.17 (2H, q, J=7.1 Hz), 4.89 (2H, s), 7.00-7.60 (3H, m)

Ethyl (4-bromo-3-methylphenoxy)acetate $^1$H-NMR (CDCl$_3$) δ ppm: 1.21 (3H, t, J=7.1 Hz), 2.30 (3H, s), 4.16 (2H, q, J=7.1 Hz), 4.76 (2H, s), 6.68-6.76 (1H, m), 6.97 (1H, d, J=3.1 Hz), 7.45 (1H, d, J=9.0 Hz)

Ethyl (4-bromo-3,5-dimethylphenoxy)acetate $^1$H-NMR (CDCl$_3$) δ ppm: 1.30 (3H, t, J=7.2 Hz), 2.37 (6H, s), 4.27 (2H, q, J=7.2 Hz), 4.57 (2H, s), 6.65 (2H, s)

Ethyl [2,6-dimethyl-4-(4,4,5,5-tetramethyl-1,3,2-dioxaborolan-2-yl)phenoxy]acetate $^1$H-NMR (CDCl$_3$) δ ppm: 1.30-1.35 (15H, m), 2.30 (6H, s), 4.30 (2H, q, J=7.2 Hz), 4.40 (2H, s), 7.48 (2H, s)

Ethyl (4-iodo-2,5-dimethylphenoxy)acetate $^1$H-NMR (CDCl$_3$) δ ppm: 1.30 (3H, t, J=7.2 Hz), 2.20 (3H, s), 2.36 (3H, s), 4.27 (2H, q, J=7.2 Hz), 4.60 (2H, s), 6.59 (1H, s), 7.55 (1H, s)

REFERENCE EXAMPLE 27

2-(4-Bromo-2,6-dimethylphenoxy)ethanol

Sodium borohydride (0.21 g) was added to a mixture of ethyl (4-bromo-2,6-dimethylphenoxy)acetate (0.78 g), tetrahydrofuran (5 mL) and ethanol (5 mL), and the mixture was stirred at room temperature for 4 hrs. The reaction mixture was diluted with water, and extracted with ethyl acetate. The organic layer was washed with water and brine, and dried over anhydrous magnesium sulfate. The solvent was evaporated under reduced pressure, and the residue was purified by silica gel column chromatography (eluent:ethyl acetate/n-hexane=1/2) to afford the title compound (0.65 g).

$^1$H-NMR (CDCl$_3$) δ ppm: 2.08 (1H, t, J=6.2 Hz), 2.26 (6H, s), 3.85-3.90 (2H, m), 3.90-4.00 (2H, m), 7.15 (2H, s)

REFERENCE EXAMPLE 28

The following compounds were prepared according to procedures analogous to those as described in Reference Example 27 by using the corresponding ethyl phenoxyacetate derivatives.

2-(4-Bromo-2-methylphenoxy)ethanol $^1$H-NMR (CDCl$_3$) δ ppm: 2.21 (3H, s), 3.94-4.08 (4H, m), 6.69 (1H, t, J=8.2 Hz), 7.12-7.32 (2H, m)

2-(4-Bromo-2-chlorophenoxy)ethanol $^1$H-NMR (CDCl$_3$) δ ppm: 3.95-4.04 (2H, m), 4.08-4.16 (2H, m), 6.82 (1H, d, J=8.7 Hz), 7.32 (1H, dd, J=2.2, 8.7 Hz), 7.51 (1H, d, J=2.5 Hz)

2-(4-Bromo-2-fluorophenoxy)ethanol $^1$H-NMR (CDCl$_3$) δ ppm: 3.94-4.00 (2H, m), 4.08-4.16 (2H, m), 6.87 (1H, t, J=8.7 Hz), 7.15-7.30 (2H, m)

2-(4-Bromo-3-methylphenoxy)ethanol $^1$H-NMR (CDCl$_3$) δ ppm: 2.36 (3H, s), 3.90-4.00 (2H, m), 4.00-4.10 (2H, m), 6.63 (1H, dd, J=3.0, 8.6 Hz), 6.81 (1H, d, J=3.0 Hz), 7.40 (1H, d, J=8.6 Hz)

2-(4-Bromo-3,5-dimethylphenoxy)ethanol $^1$H-NMR (CDCl$_3$) δ ppm: 1.96 (1H, t, J=6.3 Hz), 2.38 (6H, s), 3.90-4.00 (2H, m), 4.00-4.10 (2H, m), 6.67 (2H, s)

2-[2,6-Dimethyl-4-(4,4,5,5-tetramethyl-1,3,2-dioxaborolan-2-yl)phenoxy]ethanol $^1$H-NMR (CDCl$_3$) δ ppm: 1.34 (12H, s), 2.15 (1H, t, J=6.3 Hz), 2.30 (6H, s), 3.85-4.00 (4H, m), 7.50 (2H, s)

2-(4-Iodo-2,5-dimethylphenoxy)ethanol $^1$H-NMR (CDCl$_3$) δ ppm: 2.16 (3H, s), 2.38 (3H, s), 3.95-4.00 (2H, m), 4.00-4.10 (2H, m), 6.72 (1H, s), 7.54 (1H, s)

REFERENCE 29

2-[2-Methyl-4-(4,4,5,5-tetramethyl-[1,3,2]-dioxaborolan-2-yl)phenoxy]ethanol

A mixture of 2-(4-bromo-2-methylphenoxy)ethanol (5.43 g), bis(pinacolato)diboron (6.56 g), [bis(diphenylphosphino)ferrocene]dichloropalladium (0.52 g), bis (diphenylphosphino)ferrocene (0.39 g) and potassium acetate (6.92 g) in 1,4-dioxane (50 mL) was stirred at 100° C. for 15 hrs under an atmosphere of nitrogen. The solvent was evaporated under reduced pressure, and the residue was passed through a pad of silica gel (eluent:ethyl acetate/n-hexane=1/1). The crude material was purified by silica gel column chromatography (eluent:ethyl acetate/n-hexane=1/4) to afford the title compound (5.26 g).

$^1$H-NMR (CDCl$_3$) δ ppm: 1.33 (12H, s), 2.24 (3H, s), 3.94-4.03 (2H, m), 4.06-4.16 (2H, m), 6.76-6.86 (1H, m), 7.56-7.68 (2H, m)

REFERENCE EXAMPLE 30

The following compounds were prepared according to procedures analogous to those as described in Reference Example 29 by using the corresponding aryl bromide derivatives.

2-[2-Chloro-4-(4,4,5,5-tetramethyl-[1,3,2]-dioxaborolan-2-yl)phenoxy]ethanol $^1$H-NMR (CDCl$_3$) δ ppm: 1.33 (12H, s), 3.95-4.05 (2H, m), 4.13-4.23 (2H, m), 6.92 (1H, d, J=8.1 Hz), 7.66 (1H, dd, J=1.4, 8.2 Hz), 7.81 (1H, d, J=1.1 Hz)

2-[2-Fluoro-4-(4,4,5,5-tetramethyl-[1,3,2]-dioxaborolan-2-yl)phenoxy]ethanol

¹H-NMR (CDCl₃) δ ppm: 1.33 (12H, s), 3.94-4.04 (2H, m), 4.13-4.23 (2H, m), 6.92-7.00 (1H, m), 7.44-7.56 (2H, m)

2-[3-Methyl-4-(4,4,5,5-tetramethyl-[1,3,2]-dioxaborolan-2-yl)phenoxy]ethanol

¹H-NMR (CDCl₃) δ ppm: 1.33 (12H, s), 2.52 (3H, s), 3.90-4.00 (2H, m), 4.02-4.12 (2H, m), 6.64-6.80 (2H, m), 7.71 (1H, d, J=7.8 Hz)

REFERENCE EXAMPLE 31

4'-(2-Hydroxyethoxy}-3',5'-dimethylbiphenyl-4-carboxylic acid

A mixture of 2-(4-bromo-2,6-dimethylphenoxy)ethanol (0.65 g), 4-carboxyphenylboronic acid (0.87 g), tetrakis(triphenylphosphine)palladium(0) (0.15 g), cesium fluoride (2.40 g), 1,4-dioxane (7.5 mL), ethanol (2.5 mL) and water (1.5 mL) was stirred at 90° C. overnight under an atmosphere of argon. Water and ethyl acetate were added to the reaction mixture. The organic layer was separated, washed with water and brine, and dried over anhydrous magnesium sulfate. The solvent was evaporated under reduced pressure, and the residue was purified by silica gel column chromatography (eluent:ethyl acetate/n-hexane=1/1-2/1) to afford the title compound (0.29 g).

¹H-NMR (CD₃OD) δ ppm: 2.36 (6H, s), 3.85-3.95 (4H, m), 7.33 (2H, s), 7.67 (2H, d, J=8.5 Hz), 8.05 (2H, d, J=8.5 Hz)

REFERENCE EXAMPLE 32

Benzyl 4'-(2-hydroxyethoxy}-3',5'-dimethylbiphenyl-4-carboxylate

Benzyl bromide (0.13 mL) was added to a mixture of 4'-(2-hydroxyethoxy}-3',5'-dimethylbiphenyl-4-carboxylic acid (0.29 g) and potassium carbonate (0.17 g) in N,N-dimethylformamide (5 mL), and the mixture was stirred at room temperature overnight. Water and ethyl acetate were added to the reaction mixture. The organic layer was separated, washed with water and brine, and dried over anhydrous magnesium sulfate. The solvent was evaporated under reduced pressure, and the residue was purified by silica gel column chromatography (eluent:ethyl acetate/n-hexane=1/3-1/2) to afford the title compound (0.38 g).

¹H-NMR (CDCl₃) ppm: 2.15 (1H, t, J=6.0 Hz), 2.35 (6H, s), 3.90-4.00 (4H, m), 5.38 (2H, s), 7.28 (2H, s), 7.30-7.45 (3H, m), 7.45-7.50 (2H, m), 7.60 (2H, d, J=8.5 Hz), 8.11 (2H, d, J=8.5 Hz)

REFERENCE EXAMPLE 33

The following compounds were prepared according to procedures analogous to those as described in Reference Example 31 by using the corresponding aryl boronic acid derivatives and 2-(4-bromo-3,5-dimethylphenoxy)ethanol.

Ethyl 4'-(2-hydroxyethoxy)-2',6'-dimethylbiphenyl-4-carboxylate

¹H-NMR (CDCl₃) δ ppm: 1.42 (3H, t, J=7.1 Hz), 1.99 (6H, s), 3.90-4.00 (2H, m), 4.08-4.16 (2H, m), 4.41 (2H, q, J=7.1 Hz), 6.69 (2H, s), 7.21 (2H, d, J=8.4 Hz), 8.10 (2H, d, J=8.4 Hz)

4'-(2-Hydroxyethoxy)-2',6'-dimethylbiphenyl-4-ol

¹H-NMR (CD₃OD) δ ppm: 1.97 (6H, s), 3.80-3.90 (2H, m), 4.00-4.05 (2H, m), 6.66 (2H, s), 6.82 (2H, d, J=8.6 Hz), 6.89 (2H, d, J=8.6 Hz)

REFERENCE EXAMPLE 34

Ethyl [4'-(2-hydroxyethoxy)-2',6'-dimethylbiphenyl-4-yloxy]acetate

The title compound was prepared according to procedures analogous to those as described in Reference 25 by using 4'-(2-hydroxyethoxy)-2',6'-dimethylbiphenyl-4-ol.

¹H-NMR (CDCl₃) δ ppm: 1.31(3H, t, J=7.1 Hz), 2.01(6H, s), 3.94-3.99 (2H, m), 4.08-4.12 (2H, m), 4.30 (2H, q, J=7.1 Hz), 4.66 (2H, s), 6.68 (2H, s), 6.95 (2H, d, J=8.8 Hz), 7.04 (2H, d, J=8.8 Hz)

REFERENCE EXAMPLE 35

2-[2,6-Dimethyl-4-(4,4,5,5-tetramethyl-1,3,2-dioxaborolan-2-yl)phenoxy]ethyl methanesulfonate Methanesulfonyl chloride (0.14 mL) was added to a mixture of 2-[2,6-dimethyl-4-(4,4,5,5-tetramethyl-1,3,2-dioxaborolan-2-yl)phenoxy]ethanol (0.5 g) and triethylamine (0.29 mL) in methylene chloride (10 mL), and the mixture was stirred for 1 hr at room temperature. Water and ethyl acetate were added to the reaction mixture. The organic layer was separated, washed with water and brine, and dried over anhydrous magnesium sulfate. The solvent was evaporated under reduced pressure to afford the title compound (0.632 g).

¹H-NMR (CDCl₃) δ ppm: 1.33 (12H, s), 2.29 (6H, s), 3.10 (3H, s), 4.00-4.10 (2H, m), 4.50-4.60 (2H, m), 7.50 (2H, s)

REFERENCE EXAMPLE 36

4-((1R,2S)-2-{2-[2,6-Dimethyl-4-(4,4,5,5-tetramethyl-1,3,2-dioxaborolan-2-yl)phenoxy]ethylamino}-1-hydroxypropyl)phenol A mixture of 2-[2,6-dimethyl-4-(4,4,5,5-tetrramethyl-1,3,2-dioxaborolan-2-yl)phenoxy]ethyl methanesulfonate (0.63 g), 4-((1R,2S)-2-amino-1-hydroxypropyl)phenol (0.29 g) and N,N-diisopropylethylamine (0.36 mL) in N,N-dimethylformamide (10 mL) was stirred overnight at 80° C. Water and ethyl acetate were added to the reaction mixture. The organic layer was separated, washed with water and brine, and dried over anhydrous magnesium sulfate. The solvent was evaporated under reduced pressure, and the residue was purified by silica gel column chromatography (eluent: methylene chloride/methanol=10/1) to afford the title compound (0.2 g).

¹H-NMR (CDCl₃) δ ppm: 0.91 (3H, d, J=6.5 Hz), 1.34 (12H, s), 2.27 (6H, s), 2.93-3.01 (2H, m), 3.10-3.20 (1H, m), 3.88-3.93 (2H, m), 4.70 (1H, d, J=4.2 Hz), 6.80 (2H, d, J=8.5 Hz), 7.21 (2H, d, J=8.5 Hz), 7.49 (2H, s)

REFERENCE EXAMPLE 37

The following compounds were prepared according to procedures analogous to those as described in Reference Examples 35 and 36 by using corresponding phenoxyethanol derivatives. 4-{(1R,2S)-2-[2-(4-Bromo-2,6-dimethylphenoxy)ethylamino]-1-hydroxypropyl}phenol ¹H-NMR (CDCl₃) δ ppm: 0.93 (3H, d, J=6.5 Hz), 2.27 (6H, s), 2.92-3.01 (2H, m), 3.12-3.18 (1H, m), 3.82-3.88 (2H, m), 4.70 (1H, d, J=4.1 Hz), 6.80 (2H, d, J=8.5 Hz), 7.14 (2H, s), 7.20 (2H, d, J=8.5 Hz)

4-((1R,2S)-1-Hydroxy-2-{2-[2-methyl-4-(4,4,5,5-tetramethyl-[1,3,2]-dioxaborolan-2-yl)phenoxy]ethylamino}propyl)phenol ¹H-NMR (CDCl₃) δ ppm: 0.92 (3H, d, J=6.5 Hz), 1.33 (12H, s), 2.13 (3H, s), 2.90-3.20 (3H, m), 4.05-4.15 (2H, m), 4.65 (1H, d, J=4.4 Hz), 6.77 (2H, d, J=8.5 Hz), 6.80 (1H, d, J=8.1 Hz), 7.17 (2H, d, J=8.5 Hz), 7.55-7.65 (2H, m)

4-((1R,2S)-2-{2-[2-Chloro-4-(4,4,5,5-tetramethyl-[1,3,2]-dioxaborolan-2-yl)phenoxy]ethylamino}-1-hydroxypropyl)phenol ¹H-NMR (CDCl₃) δ ppm: 0.90 (3H, d, J=6.8 Hz), 1.33 (12H, s), 2.85-3.25 (3H, m), 4.10-4.25 (2H, m), 4.67 (1H, d, J=4.2 Hz), 6.78 (2H, d, J=8.6 Hz), 6.90 (1H, d, J=8.1 Hz), 7.19 (2H, d, J=8.6 Hz), 7.64 (1H, dd, J=8.1, 1.5 Hz), 7.79 (1H, d, J=1.5 Hz)

4-((1R,2S)-2-{2-[2-Fluoro-4-(4,4,5,5-tetramethyl-[1,3,2]-dioxaborolan-2-yl)phenoxy]ethylamino}-1-hydroxypropyl)phenol ¹H-NMR (CDCl₃) δ ppm: 0.89 (3H, d, J=6.7 Hz), 1.33 (12H, s), 2.90-3.20 (3H, m), 4.10-4.20 (2H, m), 4.68 (1H, d, J=4.0 Hz), 6.79 (2H, d, J=8.6 Hz), 6.80-7.00 (1H, m), 7.19 (2H, d, J=8.6 Hz), 7.45-7.55 (2H, m)

4-((1R,2S)-1-Hydroxy-2-{2-[3-methyl-4-(4,4,5,5-tetramethyl-[1,3,2]-dioxaborolan-2-yl)phenoxy]ethylamino}propyl)phenol ¹H-NMR (CDCl₃) δ ppm: 0.90 (3H, d, J=6.4 Hz), 1.33 (12H, s), 2.51 (3H, s), 2.90-3.15 (3H, m), 4.05-4.15 (2H, m), 4.66 (1H, d, J=4.5 Hz), 6.60-6.70 (2H, m), 6.76 (2H, d, J=8.5 Hz), 7.16 (2H, d, J=8.5 Hz), 7.69 (1H, d, J=8.0 Hz)

4-((1R,2S)-1-Hydroxy-2-[2-(4-iodo-2,5-dimethylphenoxy)ethylamino]propyl)phenol

¹H-NMR (DMSO-d₆)₆ ppm: 0.89 (3H, d, J=6.3 Hz), 1.94 (3H, s), 2.30 (3H, s), 2.69-2.76 (2H, m), 2.79-2.92 (1H, m), 3.86-3.92 (1H, m), 3.95-4.01 (1H, m), 4.36 (1H, t, J=4.1 Hz), 4.97 (1H, d, J=3.8 Hz), 6.65-6.70 (2H, m), 6.90 (1H, s), 7.07-7.11 (2H, m), 7.50 (1H, s), 9.17 (1H, br s)

REFERENCE EXAMPLE 38

1-(4-Bromo-2,6-dimethylphenoxy)propan-2-one

The title compound was prepared according to procedures analogous to those as described in Reference Example 25 by using 4-bromo-2,6-dimethylphenol and chloroacetone.

¹H-NMR (CDCl₃) δ ppm: 2.24 (6H, s), 2.33 (3H, s), 4.31 (2H, s), 7.16(2H, s)

REFERENCE EXAMPLE 39

Methyl 3-isopropyl-3'5'-dimethyl-4'-(2-oxopropoxy)biphenyl-4-carboxylate

The title compound was prepared according to procedures analogous to those as described in Reference Example 31 by using 1-(4-bromo-2,6-dimethylphenoxy)propan-2-one and methyl 2-isopropyl-4-(4,4,5,5-tetramethyl-1,3,2-dioxaborolan-2-yl)benzoate.

¹H-NMR (CDCl₃) δ ppm: 1.31 (6H, d, J=6.9 Hz), 2.35 (6H, s), 2.37 (3H, s), 3.75-3.85 (1H, m), 3.91 (3H, s), 4.39 (2H, s), 7.25 (2H, s), 7.37 (1H, dd, J=1.9, 8.2 Hz), 7.55 (1H, d, J=1.9 Hz), 7.80(1H, d, J=8.2 Hz)

REFERENCE EXAMPLE 40

Ethyl [4-(4,4,5,5-tetramethyl-1,3,2-dioxaborolan-2-yl)phenoxy]acetate

Ethyl bromoacetate (0.60 mL) was added to a mixture of 4-(4,4,5,5-tetramethyl-1,3,2-dioxaborolan-2-yl)phenol (1.0 g) and potassium carbonate (0.94 g) in N,N-dimethylformamide (5 mL), and the mixture was stirred overnight at 80° C. Water and ethyl acetate were added to the reaction mixture. The organic layer was separated, washed with water and brine, and dried over anhydrous magnesium sulfate. The solvent was evaporated under reduced pressure, and the residue was purified by silica gel column chromatography (eluent: n-hexane/ethyl acetate=10/1) to afford the title compound (1.33 g).

¹H-NMR (CDCl₃) δ ppm: 1.29 (3H, t, J=7.2 Hz), 1.33 (12H, s), 4.26 (2H, q, J=7.2 Hz), 4.64 (2H, s), 6.90 (2H, d, J=8.6 Hz), 7.75 (2H, d, J=8.6 Hz)

REFERENCE EXAMPLE 41

2-[4-(4,4,5,5-Tetramethyl-1,3,2-dioxaborolan-2-yl)phenoxy]-ethanol

Sodium borohydride (0.33 g) was added to a mixture of ethyl [4-(4,4,5,5-tetramethyl-1,3,2-dioxaborolan-2-yl)phenoxy]-acetate (1.33 g), tetrahydrofuran (10 mL) and ethanol (10 mL). The mixture was stirred at room temperature for 4 hrs, and water was added. The resulting mixture was extracted with ethyl acetate. The organic layer was washed with water and brine, and dried over anhydrous magnesium sulfate. The solvent was evaporated under reduced pressure, and the residue was purified by silica gel column chromatography (eluent: n-hexane/ethyl acetate=2/1) to afford the title compound (1.13 g).

¹H-NMR (CDCl₃) δ ppm: 1.34 (12H, s), 2.01 (1H, t, J=6.3 Hz), 3.90-4.00 (2H, m), 4.10-4.15 (2H, m), 6.91 (2H, d, J=8.7 Hz), 7.76 (2H, d, J=8.7 Hz)

REFERENCE EXAMPLE 42

Ethyl 4'-(2-hydroxyethoxy)biphenyl-4-carboxylate

The title compound was prepared according to procedures analogous to those as described in Reference Examples 40 and 41 by using ethyl 4'-hydroxybiphenyl-4-carboxylate.

¹H-NMR (CDCl₃) δ ppm: 1.41 (3H, t, J=7.1 Hz), 4.00 (2H, t, J=4.4 Hz), 4.10-4.20 (2H, m), 4.40 (2H, q, J=7.1 Hz), 7.02 (2H, d, J=8.9 Hz), 7.58 (2H, d, J=8.9 Hz), 7.62 (2H, d, J=8.5 Hz), 8.09 (2H, d, J=8.5 Hz)

REFERENCE EXAMPLE 43

2-[4-(4,4,5,5-Tetramethyl-1,3,2-dioxaborolan-2-yl)phenoxy]-ethyl methanesulfonate Methanesulfonyl chloride (0.33 mL) was added to a mixture of 2-[4-(4,4,5,5-tetramethyl-1,3,2-dioxaborolan-2-yl)phenoxy]ethanol (0.92 g) and triethylamine (0.73 mL) in methylene chloride (18 mL), and the mixture was stirred at room temperature for 1 hr. 1 mol/L hydrochloric acid was added to the reaction mixture. The organic layer was separated, washed with water and brine, and dried over anhydrous magnesium sulfate. The solvent was evaporated under reduced pressure to afford the title compound (1.28 g).
$^1$H-NMR (CDCl$_3$) δ ppm: 1.34 (12H, s), 2.87 (3H, s), 3.21 (2H, t, J=6.9 Hz), 4.45 (2H, t, J=6.9 Hz), 7.29 (2H, d, J=7.5 Hz), 7.64 (2H, d, J=7.5 Hz)

REFERENCE EXAMPLE 44

4-((1R,2S)-2-{2-[4-(4,4,5,5-Tetramethyl-1,3,2-dioxaborolan-2-yl)phenoxy]ethylamino}-1-hydroxypropyl)phenol A mixture of 2-[4-(4,4,5,5-tetramethyl-1,3,2-dioxaborolan-2-yl)phenoxy]ethyl methanesulfonate (1.20 g) and 4-((1R,2S)-2-amino-1-hydroxypropyl)phenol (1.76 g) in N,N-dimethylformamide (20 mL) was stirred at 80° C. for 5 hrs. Ethyl acetate was added to the reaction mixture. The organic layer was washed with water and brine, and dried over anhydrous magnesium sulfate. The solvent was evaporated under reduced pressure, and the residue was purified by silica gel column chromatography (eluent:n-hexane/ethyl acetate=1/1, methylene chloride/methanol=9/1) to afford the title compound (0.24 g).
$^1$H-NMR (CDCl$_3$) δ ppm: 0.92 (3H, d, J=6.3 Hz), 1.33 (12H, s), 2.90-3.25 (3H, m), 4.05-4.15 (2H, m), 4.66 (1H, d, J=4.3 Hz), 6.76 (2H, d, J=8.7 Hz), 6.85 (2H, d, J=8.4 Hz), 7.15 (2H, d, J=8.7 Hz), 7.73 (2H, d, J=8.4 Hz)

EXAMPLE 1

4'-{2-[(1S,2R)-2-Hydroxy-2-(4-hydroxyphenyl)-1-methylethylamino]ethoxy}-3',5'-dimethylbiphenyl-4-carboxylic acid (compound 1)

Step 1

Methanesulfonyl chloride (0.10 mL) was added to an ice-cooled mixture of benzyl 4'-(2-hydroxy-ethoxy)-3',5'-dimethylbiphenyl-4-carboxylate (0.38 g) and triethylamine (0.21 mL) in methylene chloride (5 mL) with stirring, and the mixture was stirred at room temperature for 1 hr. Water and ethyl acetate were added to the reaction mixture. The organic layer was separated, washed with water and brine, and dried over anhydrous magnesium sulfate. The solvent was evaporated under reduced pressure to afford benzyl 4'-(2-methanesulfonyloxy-ethoxy)-3'5'-dimethylbiphenyl-4-carboxylate (0.45 g).

Step 2

A mixture of benzyl 4'-(2-methanesulfonyloxyethoxy)-3',5'-dimethylbiphenyl-4-carboxylate (0.20 g), 4-((1R,2S)-2-amino-1-hydroxypropyl)phenol (0.074 g) and diisopropylamine (0.074 mL) in N,N-dimethylformamide (2 mL) was stirred at 80° C. overnight. Water and ethyl acetate were added to the reaction mixture. The organic layer was separated, washed with water and brine, and dried over anhydrous magnesium sulfate. The solvent was evaporated under reduced pressure, and the residue was purified by silica gel column chromatography (eluent:methylene chloride/methanol=15/1-10/1) to afford benzyl 4'-{2-[(1S,2R)-2-hydroxy-2-(4-hydroxyphenyl)-1-methylethylamino]ethoxy}-3',5'-dimethylbiphenyl-4-carboxylate (0.108 g).

Step 3

A mixture of benzyl 4'-{2-[(1S,2R)-2-hydroxy-2-(4-hydroxyphenyl)-1-methylethylamino]ethoxy}-3',5'-dimethylbiphenyl-4-carboxylate (0.108 g) and 10% palladium-carbon (50% wet, 0.05 g) in N,N-dimethylformamide (4 mL) was stirred at room temperature for 1.5 hrs under an atmosphere of hydrogen. The catalyst was removed by filtration, and the filtrate was concentrated in vacuo. Methylene chloride was added to the residue. The resulting precipitate was collected by filtration, and purified by octadecyl silica gel column chromatography (eluent:acetonitrile/water=1/1) to afford the title compound (0.025 g) as a white amorphous. The structure and physical data were shown in table 1.

EXAMPLE 2

(4'-{2-[(1S,2R)-2-Hydroxy-2-(4-hydroxyphenyl)-1-methylethylamino]ethoxy}-2',6'-dimethylbiphenyl-4-yloxy)acetic acid (compound 2)

Step 1

Methanesulfonyl chloride (0.17 mL) was added to an ice-cooled mixture of ethyl [4'-(2-hydroxyethoxy)-2',6'-dimethylbiphenyl-4-yloxy]acetate (0.58 g) and triethylamine (0.36 mL) in methylene chloride (5 mL) with stirring, and the mixture was stirred at room temperature for 1 hr. Water and ethyl acetate were added to the reaction mixture. The organic layer was separated, washed with water and brine, and dried over anhydrous magnesium sulfate. The solvent was evaporated under reduced pressure to afford ethyl [4'-(2-methanesulfonyloxyethoxy)-2',6'-dimethylbiphenyl-4-yloxy]acetate.

Step 2

A mixture of [4'-(2-methanesulfonyloxyethoxy)-2',6'-dimethylbiphenyl-4-yloxy]acetate and 4-((1R,2S)-2-amino-1-hydroxypropyl)phenol (0.71 g) in N,N-dimethylformamide (10 mL) was stirred at 80° C. overnight. Water and ethyl acetate were added to the reaction mixture. The organic layer was separated, washed with water and brine, and dried over anhydrous magnesium sulfate. The solvent was evaporated under reduced pressure, and the residue was purified by silica gel column chromatography (eluent:methylene chloride/methanol=10/1) to afford ethyl (4'-{2-[(1S,2R)-2-hydroxy-2-(4-hydroxyphenyl)-1-methylethylamino]ethoxy}-2',6'-dimethylbiphenyl-4-yloxy)acetate (0.47 g).

Step 3

A 1 mol/L aqueous solution of sodium hydroxide (0.81 mL) was added to a mixture of ethyl (4'-{2-[(1S,2R)-2-hydroxy-2-(4-hydroxyphenyl)-1-methylethylamino]ethoxy}-2',6'-dimethyl biphenyl-4-yloxy)acetate (0.16 g), water (1 mL) and 1,4-dioxane (2 mL), and the mixture was stirred at room temperature overnight. 1 mol/L hydrochloric acid (0.81 mL) was added to the reaction mixture, and the organic solvent was evaporated under reduced pressure. The precipitate was collected by filtration to afford the title compound (0.12 g) as a pale yellow amorphous. The structure and physical data were shown in table 1.

EXAMPLE 3

4'-{2-[(1S,2R)-2-Hydroxy-2-(4-hydroxyphenyl)-1-methylethylamino]ethoxy}-2,3',5'-trimethylbiphenyl-4-carboxylic acid (compound 3)

A mixture of 4-((1R,2S)-2-{2-[2,6-dimethyl-4-(4,4,5,5-tetramethyl-1,3,2-dioxaborolan-2-yl)phenoxy]ethylamino}-1-hydroxypropyl)phenol (0.02 g), 4-bromo-3-methylbenzoic acid (0.020 g), tetrakis(triphenylphosphine)palladium (0.0027 g), cesium fluoride (0.041 g), 1,4-dioxane (0.75 mL), ethanol (0.25 mL) and water (0.15 mL) was stirred at 100° C. overnight. After being cooled to room temperature, the reaction mixture was diluted with tetrahydrofuran (2.5 mL). The crude product was purified by SCX ion exchange column chromatography (Argonaut 1 g, preconditioning: tetrahydrofuran, washing solvent:tetrahydrofuran, eluent:2 mol/L ammonia in methanol), followed by reverse phase column chromatography (Shiseido Capcell Pak C18 ODS, 5 μm, 120 Å, 20×50 mm, linear gradient 0.1% aqueous formic acid/acetonitrile=90/10-60/40) to afford the title compound (0.0046 g) as a white amorphous. The structure and physical data were shown in table 1.

EXAMPLE 4

4'-{2-[(1S,2R)-2-Hydroxy-2-(4-hydoxyphenyl)-1-methylethylamino]ethoxy}-3-isopropyl-3',5'-dimethylbiphenyl-4-carboxylic acid (compound 4)

The title compound was prepared as a white amorphous according to procedures analogous to those as described in Example 3 by using 4-bromo-2-isopropylbenzoic acid. The structure and physical data were shown in table 1.

EXAMPLE 5

The following compounds 5-144 were prepared by using the corresponding arylhalides or aryltriflates and arylboronic acid derivatives according to procedures analogous to those as described in Example 3 and, if required, Step 3 in Example 2. Their structures and physical data were shown in table 1.

TABLE 1

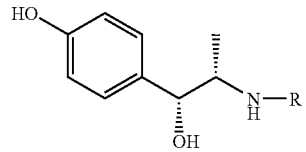

| Compound No | R | $^1$H-NMR (δ ppm), MS(m/z) |
|---|---|---|
| 1 | (4'-carboxy-3,5-dimethylbiphenyl-4-yloxy)ethyl | DMSO-d$_6$: 0.91 (3H, d, J=6.5 Hz), 2.26 (6H, s), 2.75–3.00 (3H, m), 3.75–3.90 (2H, m), 4.47–4.53 (1H, m), 6.70 (2H, d, J=8.5 Hz), 7.14 (2H, d, J=8.5 Hz), 7.39 (2H, s), 7.73 (2H, d, J=8.4 Hz), 7.97 (2H, d, J=8.4 Hz) MS(ESI, m/z): 436(M + H)$^+$ |
| 2 | | DMSO-d$_6$: 0.93 (3H, d, J=6.3 Hz), 1.91 (6H, s), 3.00–3.23 (3H, m), 4.05–4.20 (2H, m), 4.55 (2H, s), 4.75–4.85 (1H, m), 6.67 (2H, s), 6.73 (2H, d, J=8.0 Hz), 6.88 (4H, s), 7.14 (2H, d, J=8.0 Hz), 9.29 (1H, br s) MS(ESI, m/z): 466(M + H)$^+$ |
| 3 | | DMSO-d$_6$: 0.94 (3H, d, J=6.3 Hz), 2.24 (6H, s), 2.28 (3H, s), 2.85–3.10 (3H, m), 3.80–3.95 (2H, m), 4.55–4.62 (1H, m), 6.72 (2H, d, J=8.5 Hz), 7.02 (2H, s), 7.15 (2H, d, J=8.5 Hz), 7.27 (1H, d, J=8.1 Hz), 7.78 (1H, d, J=8.1 Hz), 7.85 (1H, s), 9.25 (1H, br s) MS(ESI, m/z): 450(M + H)$^+$ |

TABLE 1-continued

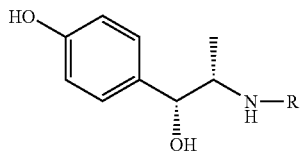

| Compound No | R | $^1$H-NMR ($\delta$ ppm), MS(m/z) |
|---|---|---|
| 4 | (3-isopropyl-3',5'-dimethyl-4-carboxybiphenyl-4'-yloxy)ethyl | DMSO-d$_6$: 0.93 (3H, d, J=6.3 Hz), 1.25 (6H, d, J=6.7 Hz), 2.27 (6H, s), 2.85–3.10 (3H, m), 3.70–3.95 (3H, m), 4.57 (1H, br s), 6.71 (2H, d, J=8.7 Hz), 7.14 (2H, d, J=8.7 Hz), 7.35 (2H, s), 7.46 (1H, d, J=7.8 Hz), 7.60 (1H, s), 7.70 (1H, d, J=7.8 Hz), 9.22 (1H, br) MS(ESI, m/z): 478(M + H)$^+$ |
| 5 | (3',5'-dimethyl-4'-(carboxymethoxy)biphenyl-4-yloxy)ethyl | MS(ESI, m/z): 466(M + H)$^+$ |
| 6 | (3-methoxy-3',5'-dimethyl-4-(carboxymethoxy)biphenyl-4'-yloxy)ethyl | MS(ESI, m/z): 496(M + H)$^+$ |
| 7 | (3-acetyl-3',5'-dimethyl-4-(carboxymethoxy)biphenyl-4'-yloxy)ethyl | MS(ESI, m/z): 508(M + H)$^+$ |
| 8 | (3-hydroxymethyl-3',5'-dimethyl-4-(carboxymethoxy)biphenyl-4'-yloxy)ethyl | MS(ESI, m/z): 496(M + H)$^+$ |

TABLE 1-continued

| Compound No | R | ¹H-NMR (δ ppm), MS(m/z) |
|---|---|---|
| 9 | | MS(ESI, m/z): 504(M + H)⁺ |
| 10 | | MS(ESI, m/z): 504(M + H)⁺ |
| 11 | | MS(ESI, m/z): 466(M + H)⁺ |
| 12 | | MS(ESI, m/z): 480(M + H)⁺ |
| 13 | | MS(ESI, m/z): 494(M + H)⁺ |

TABLE 1-continued
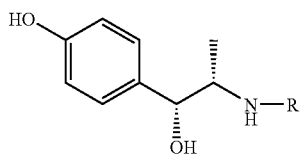
| Compound No | R | ¹H-NMR (δ ppm), MS(m/z) |
|---|---|---|
| 14 | 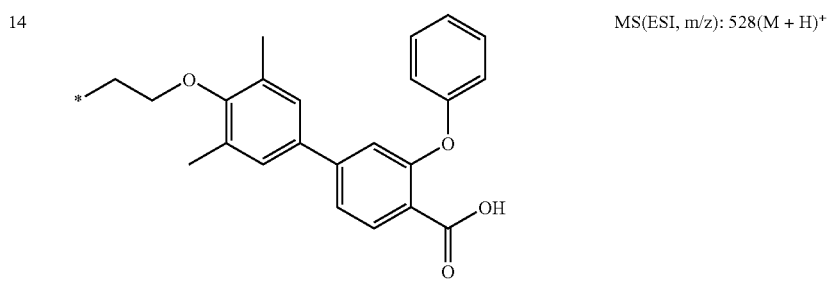 | MS(ESI, m/z): 528(M + H)+ |
| 15 | 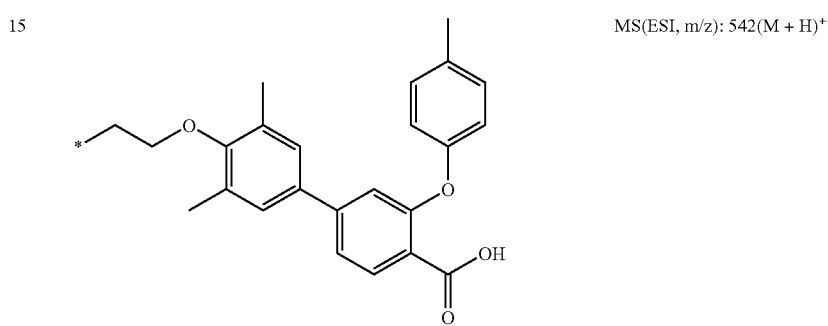 | MS(ESI, m/z): 542(M + H)+ |
| 16 | 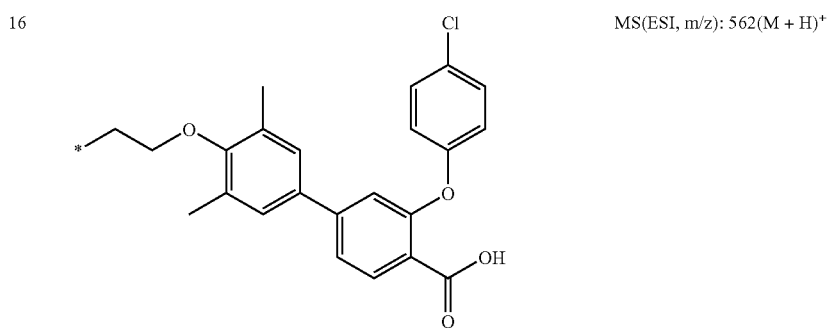 | MS(ESI, m/z): 562(M + H)+ |
| 17 | 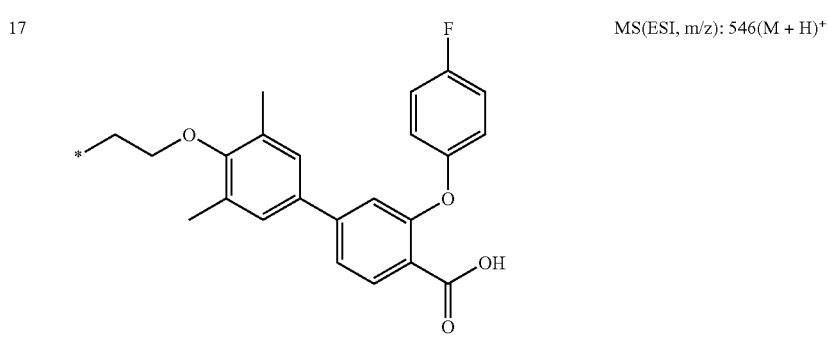 | MS(ESI, m/z): 546(M + H)+ |

TABLE 1-continued

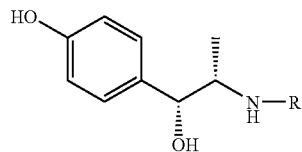

| Compound No | R | $^1$H-NMR (δ ppm), MS(m/z) |
|---|---|---|
| 18 | *(3,5-dimethyl-4-(ethoxy)-biphenyl with 4-methoxyphenoxy and carboxylic acid substituents)* | MS(ESI, m/z): 558(M + H)$^+$ |
| 19 | *(3,3',5,5'-tetramethyl-4-(ethoxy)-4'-(carboxymethoxy)biphenyl)* | MS(ESI, m/z): 494(M + H)$^+$ |
| 20 | *(3,5-dimethyl-4-(ethoxy)-biphenyl with acetyl and carboxylic acid substituents)* | MS(ESI, m/z): 478(M + H)$^+$ |
| 21 | *(2,2'-dimethyl-4-(ethoxy)-4'-carboxybiphenyl)* | MS(ESI, m/z): 436(M + H)$^+$ |
| 22 | *(2-methyl-4-(ethoxy)-6'-methoxy-3'-carboxybiphenyl)* | MS(ESI, m/z): 452(M + H)$^+$ |

TABLE 1-continued
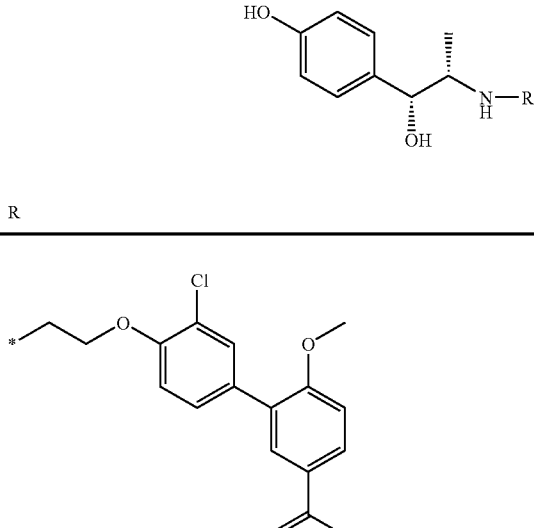
| Compound No | R | $^1$H-NMR (δ ppm), MS(m/z) |
|---|---|---|
| 23 | 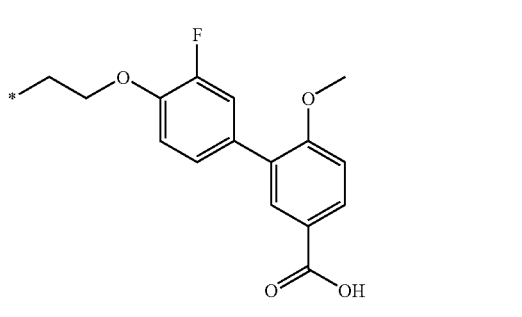 | MS(ESI, m/z): 472(M + H)$^+$ |
| 24 | 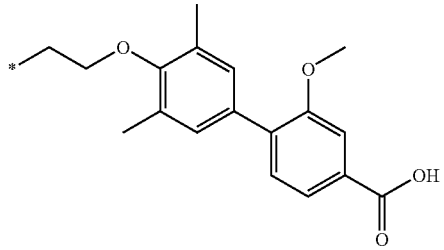 | MS(ESI, m/z): 456(M + H)$^+$ |
| 25 | 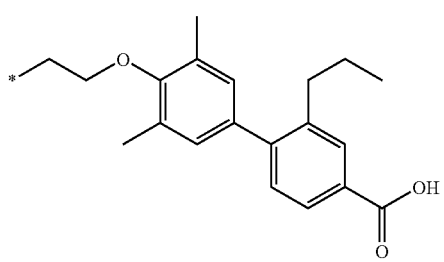 | MS(ESI, m/z): 466(M + H)$^+$ |
| 26 | 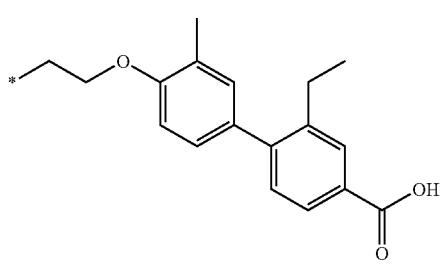 | MS(ESI, m/z): 478(M + H)$^+$ |
| 27 | | MS(ESI, m/z): 450(M + H)$^+$ |

TABLE 1-continued

| Compound No | R | ¹H-NMR (δ ppm), MS(m/z) |
|---|---|---|
| 28 | (4-(2-*oxy)ethyl)-3-methyl-2'-propyl-biphenyl-4'-carboxylic acid) | MS(ESI, m/z): 464(M + H)⁺ |
| 29 | (3,5-dimethyl-4-(2-*oxy)ethyl)-3'-tert-butyl-biphenyl-4'-carboxylic acid) | MS(ESI, m/z): 492(M + H)⁺ |
| 30 | (3,5-dimethyl-4-(2-*oxy)ethyl)-2'-isopropyl-biphenyl-4'-carboxylic acid) | MS(ESI, m/z): 478(M + H)⁺ |
| 31 | (3-methyl-4-(2-*oxy)ethyl)-2'-isopropyl-biphenyl-4'-carboxylic acid) | MS(ESI, m/z): 464(M + H)⁺ |
| 32 | (3,5-dimethyl-4-(2-*oxy)ethyl)-3'-methylthio-biphenyl-4'-carboxylic acid) | MS(ESI, m/z): 482(M + H)⁺ |

TABLE 1-continued

[Structure: 4-hydroxyphenyl-CH(OH)-CH(CH₃)-NH-R]

| Compound No | R | ¹H-NMR (δ ppm), MS(m/z) |
|---|---|---|
| 33 | *–CH₂CH₂–O–(2-methyl-4-phenyl)–(2-ethyl-4-carboxyphenyl) | MS(ESI, m/z): 450(M + H)⁺ |
| 34 | *–CH₂CH₂–O–(2-methyl-4-phenyl)–(2-isopropyl-4-carboxyphenyl) | MS(ESI, m/z): 464(M + H)⁺ |
| 35 | *–CH₂CH₂–O–(2-methyl-4-phenyl)–(2-propyl-4-carboxyphenyl) | MS(ESI, m/z): 464(M + H)⁺ |
| 36 | *–CH₂CH₂–O–(2-methyl-4-phenyl)–(2,3-dihydrobenzofuran-7-carboxylic acid-5-yl) | MS(ESI, m/z): 478(M + H)⁺ |
| 37 | *–CH₂CH₂–O–(3,5-dimethyl-4-phenyl)–(2-ethoxy-4-carboxyphenyl) | MS(ESI, m/z): 480(M + H)⁺ |

TABLE 1-continued

[Structure: HO-C6H4-CH(OH)-CH(CH3)-NH-R]

| Compound No | R | ¹H-NMR (δ ppm), MS(m/z) |
|---|---|---|
| 38 | [*-CH2CH2-O-(3,5-dimethylphenyl)-(2-isopropoxy-4-carboxyphenyl)] | MS(ESI, m/z): 494(M + H)⁺ |
| 39 | [*-CH2CH2-O-(3,5-dimethylphenyl)-(2-propoxy-4-carboxyphenyl)] | MS(ESI, m/z): 494(M + H)⁺ |
| 40 | [*-CH2CH2-O-(3-methylphenyl)-(2-ethoxy-4-carboxyphenyl)] | MS(ESI, m/z): 466(M + H)⁺ |
| 41 | [*-CH2CH2-O-(3-methylphenyl)-(2-isopropoxy-4-carboxyphenyl)] | MS(ESI, m/z): 480(M + H)⁺ |
| 42 | [*-CH2CH2-O-(3-methylphenyl)-(2-propoxy-4-carboxyphenyl)] | MS(ESI, m/z): 480(M + H)⁺ |

TABLE 1-continued

| Compound No | R | ¹H-NMR (δ ppm), MS(m/z) |
|---|---|---|
| 43 | [2-(4-{2-methyl-2'-ethoxy-4'-carboxybiphenyl})ethoxy group] | MS(ESI, m/z): 466(M + H)⁺ |
| 44 | [2-(4-{2-methyl-2'-isopropoxy-4'-carboxybiphenyl})ethoxy group] | MS(ESI, m/z): 480(M + H)⁺ |
| 45 | [2-(4-{3,5-dimethyl-3'-carboxybiphenyl})ethoxy group] | MS(ESI, m/z): 436(M + H)⁺ |
| 46 | [2-(4-{3,5-dimethyl-3'-methyl-4'-carboxybiphenyl})ethoxy group] | MS(ESI, m/z): 450(M + H)⁺ |
| 47 | [2-(4-{3,5-dimethyl-3'-carboxymethylbiphenyl})ethoxy group] | MS(ESI, m/z): 450(M + H)⁺ |

TABLE 1-continued
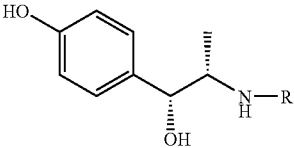
| Compound No | R | $^1$H-NMR (δ ppm), MS(m/z) |
|---|---|---|
| 48 | | MS(ESI, m/z): 450(M + H)$^+$ |
| 49 | | MS(ESI, m/z): 466(M + H)$^+$ |
| 50 | | MS(ESI, m/z): 470(M + H)$^+$ |
| 51 | | MS(ESI, m/z): 470(M + H)$^+$ |
| 52 | | MS(ESI, m/z): 454(M + H)$^+$ |

TABLE 1-continued

[Structure: HO-C6H4-CH(OH)-CH(CH3)-NH-R]

| Compound No | R | 1H-NMR (δ ppm), MS(m/z) |
|---|---|---|
| 53 | *-CH2CH2-O-(3,5-dimethylphenyl)-(2-fluoro-5-carboxyphenyl) | MS(ESI, m/z): 454(M + H)+ |
| 54 | *-CH2CH2-O-(3,5-dimethylphenyl)-(3-isopropyl-4-(carboxymethoxy)phenyl) | MS(ESI, m/z): 508(M + H)+ |
| 55 | *-CH2CH2-O-(3,5-dimethylphenyl)-(2-methyl-5-carboxyphenyl) | MS(ESI, m/z): 450(M + H)+ |
| 56 | *-CH2CH2-O-(3,5-dimethylphenyl)-(2-methyl-3-carboxyphenyl) | MS(ESI, m/z): 450(M + H)+ |
| 57 | *-CH2CH2-O-(3,5-dimethylphenyl)-(2-methoxy-5-carboxyphenyl) | MS(ESI, m/z): 466(M + H)+ |

TABLE 1-continued

[Structure: 4-hydroxyphenyl-CH(OH)-CH(CH3)-NH-R]

| Compound No | R | ¹H-NMR (δ ppm), MS(m/z) |
|---|---|---|
| 58 | *-CH2CH2-O-(3,5-dimethyl-phenyl)-(2,6-dimethoxy-phenyl)-COOH | MS(ESI, m/z): 496(M + H)+ |
| 59 | *-CH2CH2-O-(3,5-dimethyl-phenyl)-(2-chloro-phenyl)-COOH | MS(ESI, m/z): 470(M + H)+ |
| 60 | *-CH2CH2-O-(3-chloro-phenyl)-(3-fluoro-phenyl)-COOH | MS(ESI, m/z): 460(M + H)+ |
| 61 | *-CH2CH2-O-(3-chloro-phenyl)-(3-isopropyl-phenyl)-O-CH2-COOH | MS(ESI, m/z): 514(M + H)+ |
| 62 | *-CH2CH2-O-(3-chloro-phenyl)-(3-isopropyl-phenyl)-COOH | MS(ESI, m/z): 484(M + H)+ |

TABLE 1-continued
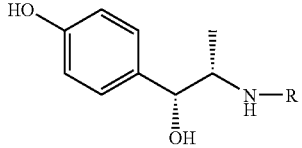
| Compound No | R | ¹H-NMR (δ ppm), MS(m/z) |
|---|---|---|
| 63 | 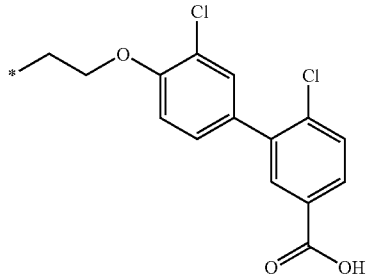 | MS(ESI, m/z): 476(M + H)⁺ |
| 64 | 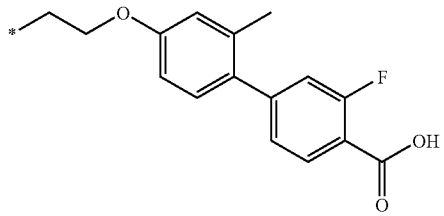 | MS(ESI, m/z): 440(M + H)⁺ |
| 65 | 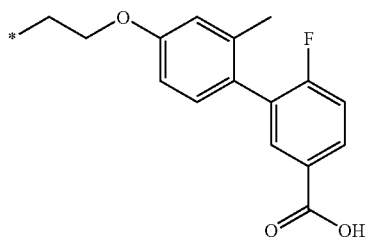 | MS(ESI, m/z): 440(M + H)⁺ |
| 66 | 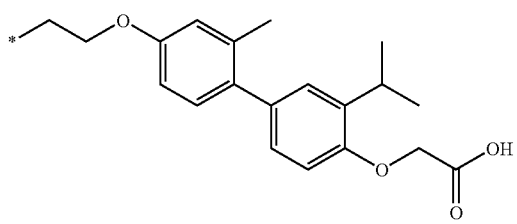 | MS(ESI, m/z): 494(M + H)⁺ |
| 67 | 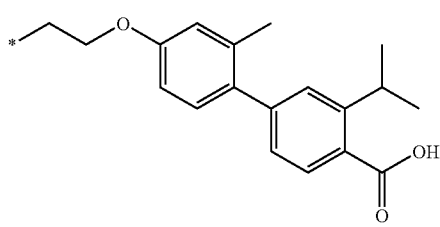 | MS(ESI, m/z): 464(M + H)⁺ |

TABLE 1-continued

| Compound No | R | $^1$H-NMR ($\delta$ ppm), MS(m/z) |
|---|---|---|
| 68 | | MS(ESI, m/z): 436(M + H)$^+$ |
| 69 | | MS(ESI, m/z): 456(M + H)$^+$ |
| 70 | | MS(ESI, m/z): 440(M + H)$^+$ |
| 71 | | MS(ESI, m/z): 494(M + H)$^+$ |
| 72 | | MS(ESI, m/z): 464(M + H)$^+$ |

TABLE 1-continued
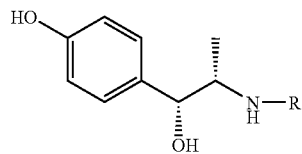
| Compound No | R | $^1$H-NMR (δ ppm), MS(m/z) |
|---|---|---|
| 73 | 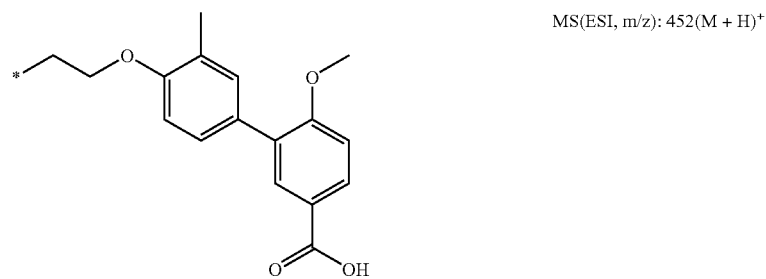 | MS(ESI, m/z): 452(M + H)$^+$ |
| 74 | 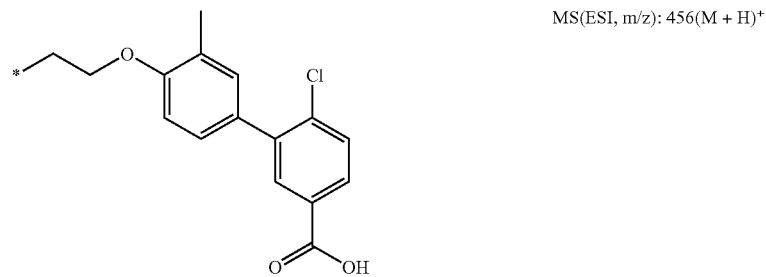 | MS(ESI, m/z): 456(M + H)$^+$ |
| 75 | 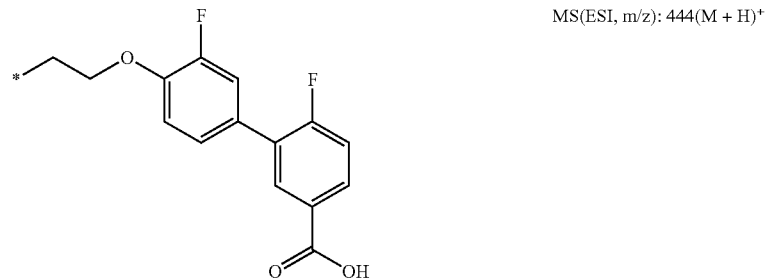 | MS(ESI, m/z): 444(M + H)$^+$ |
| 76 | 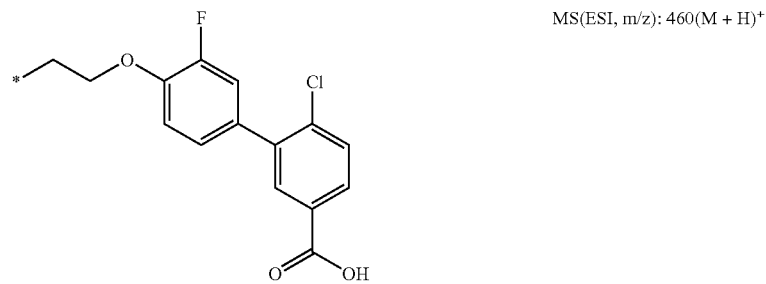 | MS(ESI, m/z): 460(M + H)$^+$ |

TABLE 1-continued
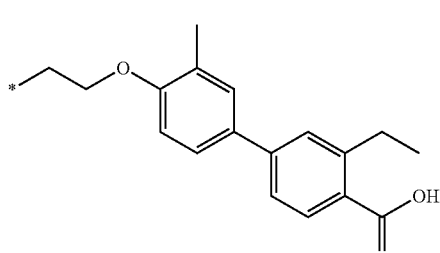
| Compound No | R | ¹H-NMR (δ ppm), MS(m/z) |
|---|---|---|
| 77 | 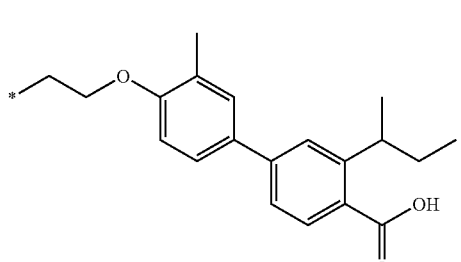 | MS(ESI, m/z): 450(M + H)⁺ |
| 78 | 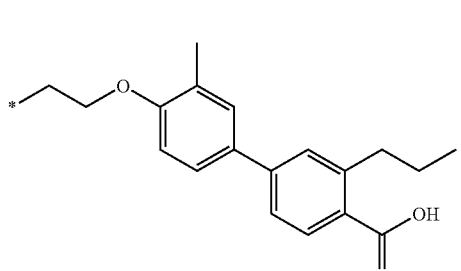 | MS(ESI, m/z): 478(M + H)⁺ |
| 79 | 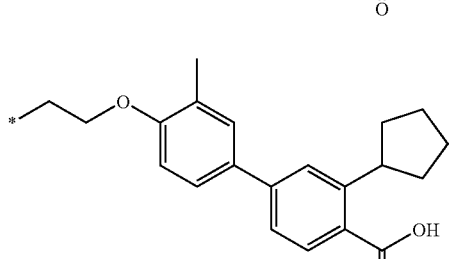 | MS(ESI, m/z): 464(M + H)⁺ |
| 80 | 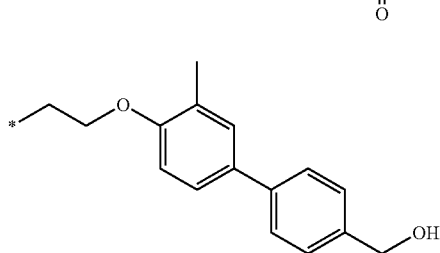 | MS(ESI, m/z): 490(M + H)⁺ |
| 81 | | MS(ESI, m/z): 422(M + H)⁺ |

TABLE 1-continued
| Compound No | R | $^1$H-NMR (δ ppm), MS(m/z) |
|---|---|---|
| 82 | 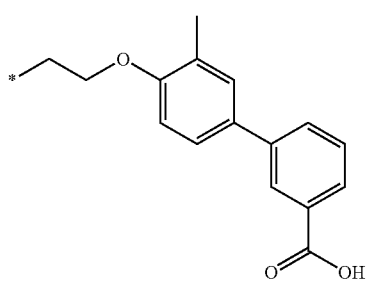 | MS(ESI, m/z): 422(M + H)$^+$ |
| 83 | 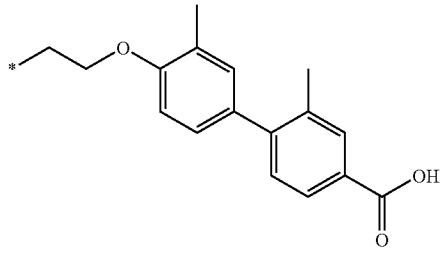 | MS(ESI, m/z): 436(M + H)$^+$ |
| 84 | 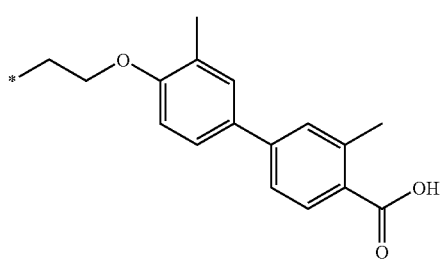 | MS(ESI, m/z): 436(M + H)$^+$ |
| 85 | 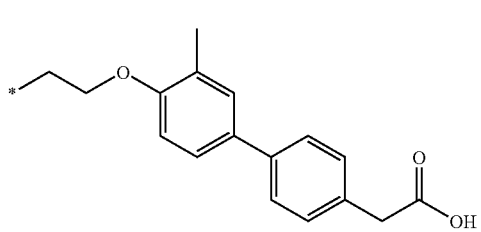 | MS(ESI, m/z): 436(M + H)$^+$ |
| 86 | 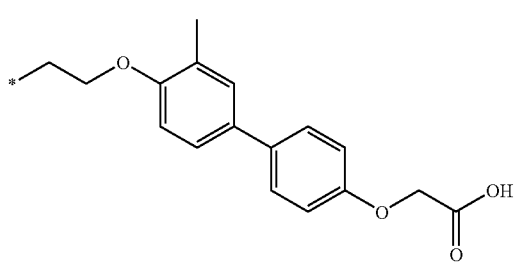 | MS(ESI, m/z): 452(M + H)$^+$ |

TABLE 1-continued

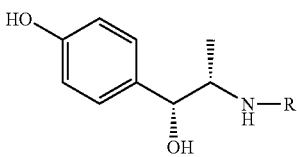

| Compound No | R | ¹H-NMR (δ ppm), MS(m/z) |
|---|---|---|
| 87 | (3-chloro-4-carboxyphenyl)-(3-methyl-4-oxyethyl) biphenyl group | MS(ESI, m/z): 456(M + H)⁺ |
| 88 | (4-carboxyphenyl)-(3-fluoro-4-oxyethyl) biphenyl group | MS(ESI, m/z): 426(M + H)⁺ |
| 89 | (2-methyl-4-carboxyphenyl)-(3-fluoro-4-oxyethyl) biphenyl group | MS(ESI, m/z): 440(M + H)⁺ |
| 90 | (3-methyl-4-carboxyphenyl)-(3-fluoro-4-oxyethyl) biphenyl group | MS(ESI, m/z): 440(M + H)⁺ |
| 91 | (4-carboxymethylphenyl)-(3-fluoro-4-oxyethyl) biphenyl group | MS(ESI, m/z): 440(M + H)⁺ |

TABLE 1-continued

| Compound No | R | $^1$H-NMR (δ ppm), MS(m/z) |
|---|---|---|
| 92 | *-CH₂CH₂-O-(3-F, 4-)-C₆H₃-(3-Cl, 4-COOH)-C₆H₃ | MS(ESI, m/z): 460(M + H)⁺ |
| 93 | *-CH₂CH₂-O-(3-Cl)-C₆H₃-C₆H₄-4-COOH | MS(ESI, m/z): 442(M + H)⁺ |
| 94 | *-CH₂CH₂-O-(3-Cl)-C₆H₃-(2-Me, 4-COOH)-C₆H₃ | MS(ESI, m/z): 456(M + H)⁺ |
| 95 | *-CH₂CH₂-O-(3-Cl)-C₆H₃-(3-Me, 4-COOH)-C₆H₃ | MS(ESI, m/z): 456(M + H)⁺ |
| 96 | *-CH₂CH₂-O-(2-Me)-C₆H₃-(3-Cl, 4-COOH)-C₆H₃ | MS(ESI, m/z): 456(M + H)⁺ |

TABLE 1-continued
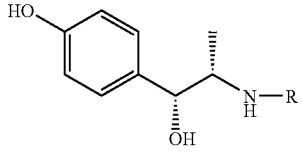
| Compound No | R | ¹H-NMR (δ ppm), MS(m/z) |
|---|---|---|
| 97 | 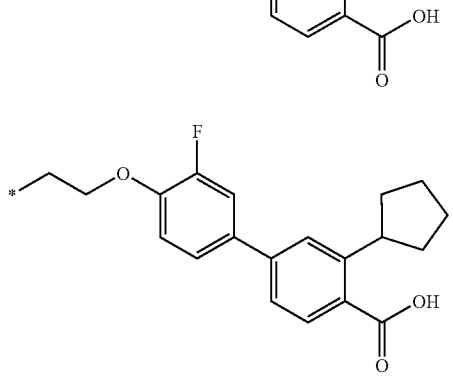 | MS(ESI, m/z): 454(M + H)⁺ |
| 98 | 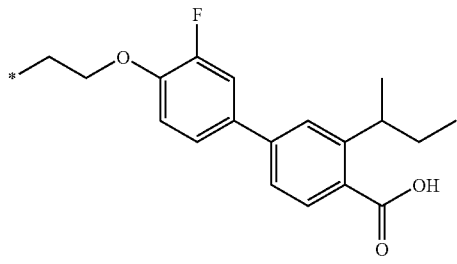 | MS(ESI, m/z): 494(M + H)⁺ |
| 99 | 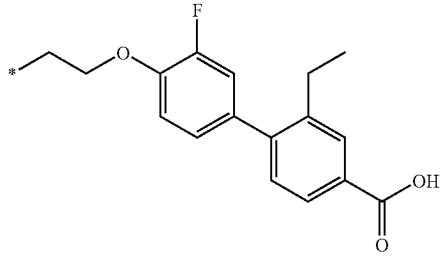 | MS(ESI, m/z): 482(M + H)⁺ |
| 100 | 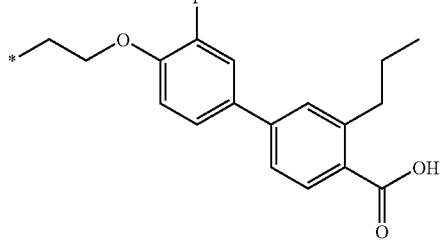 | MS(ESI, m/z): 454(M + H)⁺ |
| 101 | | MS(ESI, m/z): 468(M + H)⁺ |

TABLE 1-continued

| Compound No | R | ¹H-NMR (δ ppm), MS(m/z) |
|---|---|---|
| 102 | [3-fluoro-4-(ethoxy)-2'-isopropyl-biphenyl-4'-carboxylic acid] | MS(ESI, m/z): 468(M + H)⁺ |
| 103 | [3-fluoro-4-(ethoxy)-2'-propyl-biphenyl-4'-carboxylic acid] | MS(ESI, m/z): 468(M + H)⁺ |
| 104 | [3-chloro-4-(ethoxy)-3'-ethyl-biphenyl-4'-carboxylic acid] | MS(ESI, m/z): 470(M + H)⁺ |
| 105 | [3-chloro-4-(ethoxy)-3'-cyclopentyl-biphenyl-4'-carboxylic acid] | MS(ESI, m/z): 510(M + H)⁺ |
| 106 | [3-chloro-4-(ethoxy)-3'-sec-butyl-biphenyl-4'-carboxylic acid] | MS(ESI, m/z): 498(M + H)⁺ |

TABLE 1-continued

| Compound No | R | ¹H-NMR (δ ppm), MS(m/z) |
|---|---|---|
| 107 | (3-chloro-4-(*-ethoxy)-2'-ethyl-biphenyl-4-carboxylic acid) | MS(ESI, m/z): 470(M + H)⁺ |
| 108 | (3-chloro-4-(*-ethoxy)-2'-propyl-biphenyl-4-carboxylic acid) | MS(ESI, m/z): 484(M + H)⁺ |
| 109 | (3-chloro-4-(*-ethoxy)-2'-isopropyl-biphenyl-4-carboxylic acid) | MS(ESI, m/z): 484(M + H)⁺ |
| 110 | (3-chloro-4-(*-ethoxy)-3'-propyl-biphenyl-4-carboxylic acid) | MS(ESI, m/z): 484(M + H)⁺ |
| 111 | (4-(*-ethoxy)-2-methyl-3'-ethyl-biphenyl-4'-carboxylic acid) | MS(ESI, m/z): 450(M + H)⁺ |

TABLE 1-continued
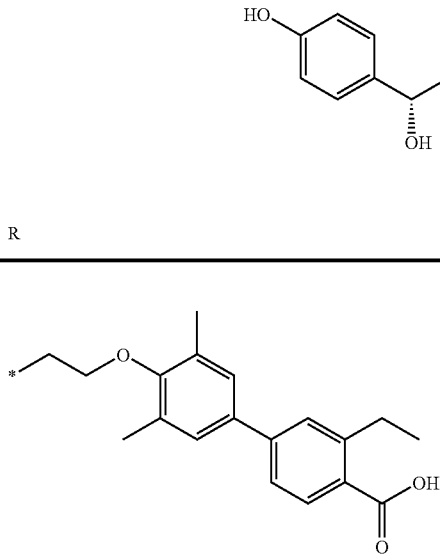
| Compound No | R | ¹H-NMR (δ ppm), MS(m/z) |
|---|---|---|
| 112 | 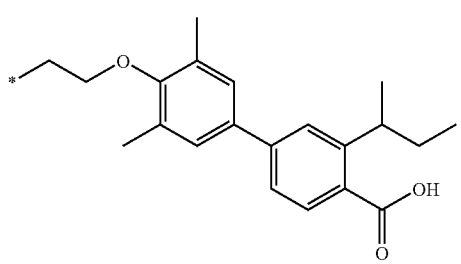 | MS(ESI, m/z): 464(M + H)⁺ |
| 113 | 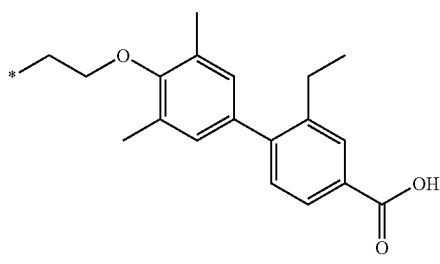 | MS(ESI, m/z): 492(M + H)⁺ |
| 114 | 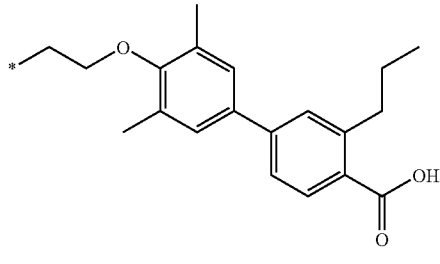 | MS(ESI, m/z): 464(M + H)⁺ |
| 115 | 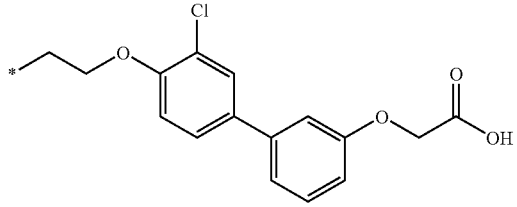 | MS(ESI, m/z): 478(M + H)⁺ |
| 116 | | MS(ESI, m/z): 472(M + H)⁺ |

TABLE 1-continued

| Compound No | R | $^1$H-NMR (δ ppm), MS(m/z) |
|---|---|---|
| 117 | | MS(ESI, m/z): 422(M + H)$^+$ |
| 118 | | MS(ESI, m/z): 436(M + H)$^+$ |
| 119 | | MS(ESI, m/z): 514(M + H)$^+$ |
| 120 | | MS(ESI, m/z): 544(M + H)$^+$ |

TABLE 1-continued

| Compound No | R | ¹H-NMR (δ ppm), MS(m/z) |
|---|---|---|
| 121 | [structure: *-CH2CH2-O-(3-methyl-phenyl)-(phenyl)-O-(4-chlorophenyl), with COOH] | MS(ESI, m/z): 548(M + H)+ |
| 122 | [structure: *-CH2CH2-O-(3-methyl-phenyl)-(phenyl)-O-(4-fluorophenyl), with COOH] | MS(ESI, m/z): 532(M + H)+ |
| 123 | [structure: *-CH2CH2-O-(3-methyl-phenyl)-(phenyl)-O-(4-methylphenyl), with COOH] | MS(ESI, m/z): 528(M + H)+ |
| 124 | [structure: *-CH2CH2-O-(3-methyl-phenyl)-(3-methoxyphenyl), with COOH] | MS(ESI, m/z): 452(M + H)+ |

TABLE 1-continued
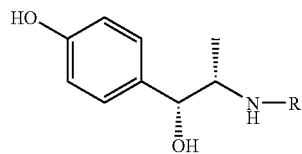
| Compound No | R | $^1$H-NMR (δ ppm), MS(m/z) |
|---|---|---|
| 125 | ![structure] | MS(ESI, m/z): 466(M + H)$^+$ |
| 126 | ![structure] | MS(ESI, m/z): 518(M + H)$^+$ |
| 127 | ![structure] | MS(ESI, m/z): 548(M + H)$^+$ |
| 128 | ![structure] | MS(ESI, m/z): 552(M + H)$^+$ |

TABLE 1-continued

| Compound No | R | ¹H-NMR (δ ppm), MS(m/z) |
|---|---|---|
| 129 | (3-fluoro-4-(*-ethoxy)phenyl)-(3-(4-fluorophenoxy))-4-carboxyphenyl | MS(ESI, m/z): 536(M + H)⁺ |
| 130 | (3-fluoro-4-(*-ethoxy)phenyl)-(3-(4-methylphenoxy))-4-carboxyphenyl | MS(ESI, m/z): 532(M + H)⁺ |
| 131 | (3-fluoro-4-(*-ethoxy)phenyl)-(3-methoxy)-4-carboxyphenyl | MS(ESI, m/z): 456(M + H)⁺ |
| 132 | (3-fluoro-4-(*-ethoxy)phenyl)-(3-ethoxy)-4-carboxyphenyl | MS(ESI, m/z): 470(M + H)⁺ |

TABLE 1-continued

| Compound No | R | ¹H-NMR (δ ppm), MS(m/z) |
|---|---|---|
| 133 | (3-chloro-4-(*-ethoxy)phenyl linked to 3-phenoxy-4-carboxyphenyl) | MS(ESI, m/z): 534(M + H)⁺ |
| 134 | (3-chloro-4-(*-ethoxy)phenyl linked to 3-(4-methoxyphenoxy)-4-carboxyphenyl) | MS(ESI, m/z): 564(M + H)⁺ |
| 135 | (3-chloro-4-(*-ethoxy)phenyl linked to 3-(4-chlorophenoxy)-4-carboxyphenyl) | MS(ESI, m/z) 568(M + H)⁺ |
| 136 | (3-chloro-4-(*-ethoxy)phenyl linked to 3-(4-fluorophenoxy)-4-carboxyphenyl) | MS(ESI, m/z): 552(M + H)⁺ |

TABLE 1-continued

| Compound No | R | ¹H-NMR (δ ppm), MS(m/z) |
|---|---|---|
| 137 | | MS(ESI, m/z): 548(M + H)⁺ |
| 138 | | MS(ESI, m/z): 472(M + H)⁺ |
| 139 | | MS(ESI, m/z): 486(M + H)⁺ |
| 140 | | MS(ESI, m/z): 514(M + H)⁺ |

TABLE 1-continued

| Compound No | R | ¹H-NMR (δ ppm), MS(m/z) |
|---|---|---|
| 141 | (4-fluorophenoxy-substituted biphenyl with ethoxy linker and carboxylic acid) | MS(ESI, m/z): 532(M + H)⁺ |
| 142 | (4-methylphenoxy-substituted biphenyl with ethoxy linker and carboxylic acid) | MS(ESI, m/z): 528(M + H)⁺ |
| 143 | (methoxy-substituted biphenyl with ethoxy linker and carboxylic acid) | MS(ESI, m/z): 452(M + H)⁺ |
| 144 | (ethoxy-substituted biphenyl with ethoxy linker and carboxylic acid) | MS(ESI, m/z): 466(M + H)⁺ | wherein * in R groups represents their connecting positions

EXAMPLE 6

(4'-{2-[(1S,2R)-2-Hydroxy-2-(4-hydroxyphenyl)-1-methylethylamino]ethoxy}-2,3',5'-trimethylbiphenyl-4-yloxy)acetic Acid (compound 145)

A mixture of 4-{(1R,2S)-2-[2-(4-bromo-2,6-dimethylphenoxy)ethylamino]-1-hydroxypropyl}phenol (0.03 g), [3-methyl-4-(4,4,5,5-tetramethyl-1,3,2-dioxaborolan-2-yl) phenoxy]acetic acid (0.045 g), tetrakis(triphenylphosphine)-palladium (0.0046 g), cesium fluoride (0.069 g), 1,4-dioxane (0.75 mL), ethanol (0.25 mL) and water (0.15 mL) was stirred at 100° C. overnight. After being cooled to room temperature, the reaction mixture was diluted with tetrahydrofuran (2.5 mL). The crude product was purified firstly by SCX ion exchange column chromatography (Argonaut 1 g, preconditioning: tetrahydrofuran, washing solvent:tetrahydrofuran, eluent:2 mol/L ammonia in methanol), and then by reverse phase column chromatography (Shiseido Capcell Pak C18 ODS, 5 μm, 120 Å, 20×50 mm, linear gradient 0.1% aqueous formic acid/acetonitrile=90/10-60/40) to afford the title compound (0.0085 g) as a white amorphous. The structure and physical data were shown in table 2.

EXAMPLE 7

The following compounds 146-150 were prepared according to procedures analogous to those as described in Example 6 by using 4-{(1R,2s)-2-[2-(4-bromo-2,6-dimethylphenoxy)ethylamino]-1-hydroxypropyl}phenol or 4-{(1R,2s)-2-[2-(4-bromo-2,5-dimethylphenoxy)ethylamino]-1-hydroxypropyl}-phenol, and the corresponding arylboronic acid derivatives. Their structures and physical data were shown in table 2.

EXAMPLE 8

4'-{(2RS)-2-[(1S,2R)-2-Hydroxy-2-(4-hydroxyphenyl)-1-methylethylamino]propoxy}-3-isopropyl-3',5'-dimethylbiphenyl-4-carboxylic acid (compound 151)

Step 1

Sodium triacetoxyborohydride (0.23 g) was added to a mixture of 4-((1R,2S)-2-amino-1-hydroxypropyl)phenol (0.082 g), methyl 3-isopropyl-3',5'-dimethyl-4'-(2-oxo-propoxy)biphenyl-4-carboxylate (0.17 g) and acetic acid (0.03 mL) in tetrahydrofuran (2.5 mL) at room temperature with stirring, and the mixture was stirred at 50° C. for 4 hrs. After being cooled to room temperature, the reaction mixture was partitioned between a saturated aqueous solution of sodium bicarbonate and ethyl acetate. The organic layer was separated, washed with water and brine, and dried over anhydrous magnesium sulfate. The solvent was evaporated under reduced pressure. The residue was purified by silica gel column chromatography (eluent:methylene chloride/methanol=9/1) followed by aminopropyl silica gel column chromatography (eluent:hexane/ethyl acetate=4/1) to afford methyl 4'-{(2RS)-2-[(1S,2R)-2-hydroxy-2-(4-hydroxyphenyl)1-methylethylamino]propoxy}-3-isopropyl-3',5'-dimethylbiphenyl-4-carboxylate (0.074 g).

$^1$H-NMR (CDCl$_3$) δ ppm: 0.85-0.95 (3H, m), 1.15-1.35 (9H, m), 2.32 (2.7H, s), 2.36 (3.3H, s), 3.05-3.20 (1H, m), 3.20-3.35 (1H, m), 3.65-3.85 (3H, m), 3.91 (3H, s), 4.69 (0.45H, d, J=4.1 Hz), 4.71 (0.55H, d, J=3.8 Hz), 6.75-6.85 (2H, m), 7.15-7.20 (2H, m), 7.20-7.25 (2H, m), 7.35-7.40 (1H, m), 7.50-7.60 (1H, m), 7.75-7.85 (1H, m)

MS (ESI, m/z): 506 (M+H)$^+$

Step 2

The title compound was prepared as a gray amorphous according to procedures analogous to those as described in Step 2 in Example 3 by using methyl 4'-{(2RS)-2-[(1S,2R)-2-hydroxy-2-(4-hydroxyphenyl)-1-methylethylamino]propoxy}-3-isopropyl-3',5'-dimethylbiphenyl-4-carboxylate. The structure and physical data were shown in table 2.

TABLE 2

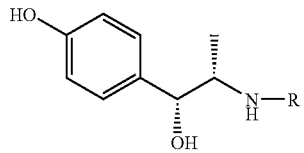

| Compound No | R | $^1$H-NMR (δ ppm), MS(m/z) |
|---|---|---|
| 145 | [structure shown] | DMSO-d$_6$: 0.95 (3H, d, J=6.4 Hz), 2.13 (3H, s), 2.21 (6H, s), 3.00–3.20 (3H, m), 3.80–3.95 (2H, m), 4.49 (2H, s), 4.72–4.80 (1H, m), 6.64 (1H, dd, J=2.5, 8.3 Hz), 6.72 (2H, d, J=8.5 Hz), 6.75 (1H, d, J=2.5 Hz), 6.85 (1H, d, J=8.3 Hz), 6.88 (2H, s), 7.16 (2H, d, J=8.5 Hz), 9.29 (1H, br) MS(ESI, m/z) 480(M + H)$^+$ |
| 146 | [structure shown] | MS(ESI, m/z): 508(M + H)$^+$ |

TABLE 2-continued
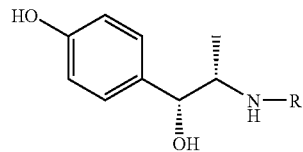
| Compound No | R | $^1$H-NMR (δ ppm), MS(m/z) |
|---|---|---|
| 147 | *-CH2CH2-O-(3,5-dimethylphenyl)-(3-hydroxy-4-carboxyphenyl) | MS(ESI, m/z): 452(M + H)$^+$ |
| 148 | *-CH2CH2-O-(3,5-dimethylphenyl)-(3-ethoxy-4-(carboxymethoxy)phenyl) | MS(ESI, m/z): 510(M + H)$^+$ |
| 140 | *-CH2CH2-O-(3,5-dimethylphenyl)-(4-(carboxymethyl)phenyl) | MS(ESI, m/z): 450(M + H)$^+$ |
| 150 | *-CH2CH2-O-(2,5-dimethylphenyl)-(4-carboxyphenyl) | DMSO-d$_6$: 0.94 (3H, d, J=6.4 Hz), 2.06 (3H, s), 2.21 (3H, s), 2.93–3.12 (3H, m), 4.04–4.17 (2H, m), 4.58 (1H, d, J=4.5 Hz), 6.70 (1H, s), 6.71 (2H, d, J=8.5 Hz), 6.86 (1H, s), 7.14 (2H, d, J=8.5 Hz), 7.39 (2H, d, J=8.3 Hz), 7.96 (2H, d, J=8.3 Hz) |

TABLE 2-continued

| Compound No | R | $^1$H-NMR (δ ppm), MS(m/z) |
|---|---|---|
| 151 | (structure: *–CH(CH₃)–O– linked to 4-position of 3,5-dimethyl biphenyl with 2-isopropyl-4-carboxylic acid) | DMSO-d$_6$: 0.85–0.95 (3H, m), 1.10–1.30 (9H, m), 2.25–2.35 (6H, m), 2.95–3.10 (1H, m), 3.15–3.35 (1H, m), 3.60–3.90 (3H, m), 4.60 (0.45H, d, J=4.1 Hz), 4.63 (0.55H, d, J=3.8 Hz), 6.65–6.75 (2H, m), 7.10–7.15 (2H, m), 7.35–7.40 (2H, m), 7.40–7.50 (1H, m), 7.55–7.65 (1H, m), 7.65–7.75 (1H, m)<br>MS(ESI, m/z) 492(M + H)$^+$ | wherein * in R groups represents their connecting positions

EXAMPLE 9

4'-{2-[(1S,2R)-2-Hydroxy-2-(4-hydroxyphenyl)-1-methylethyl-amino]ethoxy}biphenyl-4-carboxylic acid (compound 152)

Step 1

Methanesulfonyl chloride (0.13 mL) was added to an ice-cooled mixture of ethyl 4'-(2-hydroxyethoxy)biphenyl-4-carboxylate (0.41 g) and triethylamine (0.30 mL) in tetrahydrofuran (8 mL) with stirring. The mixture was stirred at that temperature for 30 min, at room temperature for 45 min, and at 45° C. for 1 hr. Methanesulfonyl chloride (0.13 mL) and triethylamine (0.30 mL) were added every an hour to the reaction mixture for 3 times at 45° C., and the mixture was stirred at 70° C. for 3 hrs. 1 mol/L hydrochloric acid and ethyl acetate were added to the reaction mixture. The organic layer was separated, washed with water and brine, and dried over anhydrous magnesium sulfate. The solvent was evaporated under reduced pressure to afford ethyl 4'-(2-methanesulfonyloxyethoxy)biphenyl-4-carboxylate (0.32 g).

Step 2

Diisopropylamine (0.40 mL) was added to a mixture of ethyl 4'-(2-methanesulfonyloxyethoxy)biphenyl-4-carboxylate (0.32 g) and 4-((1R,2S)-2-amino-1-hydroxypropyl)phenol (0.32 g) in N,N-dimethylformamide (6 mL), and the mixture was stirred for 14 hrs at 80° C. After being cooled to room temperature, the reaction mixture was partitioned between methylene chloride and water. The organic layer was washed with water and brine, and dried over anhydrous magnesium sulfate. The solvent was evaporated under reduced pressure, and the residue was purified by silica gel column chromatography (eluent:methylene chloride/methanol=15/1) to afford ethyl 4'-{2-[(1S,2R)-2-hydroxy-2-(4-hydroxyphenyl)-1-methylethyl-amino]ethoxy}biphenyl-4-carboxylate (0.22 g).

$^1$H-NMR (CD$_3$OD) δ ppm: 1.50 (3H, d, J=6.2 Hz), 1.42 (3H, t, J=7.1 Hz), 2.85-3.10 (3H, m), 4.00-4.05 (1H, m), 4.10-4.20 (1H, m), 4.43 (2H, q, J=7.1 Hz), 4.53 (1H, d, J=6.7 Hz), 6.87 (2H, d, J=8.5 Hz), 7.00 (2H, d, J=8.9 Hz), 7.29 (2H, d, J=8.5 Hz), 7.70 (2H, d, J=8.9 Hz), 7.79 (2H, d, J=8.7 Hz), 8.16 (2H, d, J=8.7 Hz)

Step 3

A 2 mol/L aqueous solution of sodium hydroxide (0.43 mL) was added to a solution of ethyl 4'-(2-[(1S,2R)-2-hydroxy-2-(4-hydroxyphenyl)-1-methylethylamino]ethoxy)biphenyl-4-carboxylate (0.15 g), ethanol (20 mL) and tetrahydrofuran (5 mL). The mixture was stirred at 60° C. for 16 hrs, and heated under reflux at 100° C. for 7.5 hrs. A 2 mol/L aqueous solution of sodium hydroxide (0.17 mL) was added, and heated under reflux for 16 hrs. After being cooled to room temperature, 2 mol/L hydrochloric acid (0.60 mL) was added, and the precipitate was collected by filtration to afford the title compound as a pale yellow amorphous (0.13 g). The structure and physical data were shown in table 3.

EXAMPLE 10

2-Ethyl-4'-{(1S,2R)-2-[2-hydroxy-2-(4-hydroxyphenyl)-1-methylethylamino]ethoxy}biphenyl-4-carboxylic acid (compound 153)

A mixture of 4-((1R,2S)-2-{2-[4-(4,4,5,5-tetramethyl-1,3,2-dioxaborolan-2-yl)phenoxy]ethylamino}-1-hydroxypropyl)phenol (0.04 g), 4-bromo-3-ethylbenzoic acid (0.044 g), tetrakis(triphenylphosphine)palladium (0.011 g), cesium fluoride (0.088 g), 1,4-dioxane (0.6 mL), ethanol (0.12 mL) and water (0.2 mL) was stirred at 140° C. for 5 min in a sealed tube. After being cooled to room temperature, the reaction mixture was purified by SCX ion exchange column chromatography (2 g, preconditioning: tetrahydrofuran, washing solvent:tetrahydrofuran, eluent:2 mol/L ammonia in methanol), followed by reverse phase column chromatography (Shiseido Capcell Pak C18 ODS, 5 μm, 120 Å, 20×50 mm, linear gradient 0.1% aqueous formic acid/acetonitrile=90/10-60/40) to afford the title compound (0.010 g) as a white amorphous. The structure and physical data were shown in table 3.

EXAMPLE 11

The following compounds 154-178 were prepared according to procedures analogous to those as described in Example 10 by using 4-((1R,2S)-2-{2-[4-(4,4,5,5-tetramethyl-1,3,2-dioxa-borolan-2-yl)phenoxy]ethylamino}-1-hydroxypropyl)phenol and the corresponding arylhalide or aryltriflate derivatives. Their structures and physical data were shown in table 3.

TABLE 3

| Compound No | R | $^1$H-NMR (δ ppm), MS(m/z) |
|---|---|---|
| 152 | *-CH₂CH₂-O-C₆H₄-C₆H₄-COOH (biphenyl ether) | DMSO-d$_6$: 0.89 (3H, d, J=6.5 Hz), 2.80–2.90 (1H, m), 2.93–3.08 (2H, m), 4.03–4.17 (2H, m), 4.59 (1H, d, J=4.0 Hz), 6.71 (2H, d, J=8.4 Hz), 7.01 (2H, d, J=8.8 Hz), 7.13 (2H, d, J=8.4 Hz), 7.66 (2H, d, J=8.8 Hz), 7.71 (2H, d, J=8.4 Hz), 7.96 (2H, d, J=8.4 Hz), 9.29 (1H, br) |
| 153 | *-CH₂CH₂-O-C₆H₄-C₆H₃(Et)-COOH | DMSO-d$_6$: 0.88 (3H, d, J=6.3 Hz), 1.05 (3H, t, J=7.6 Hz), 2.61 (2H, q, J=7.6 Hz), 2.75–2.85 (1H, m), 2.90–3.00 (2H, m), 4.00–4.10 (2H, m), 4.52(1H, d, J=4.4 Hz), 6.70 (2H, d, J=8.5 Hz), 6.97(2H, d, J=8.5 Hz), 7.12 (2H, d, J=8.5 Hz), 7.20–7.30 (2H, m), 7.70–7.90 (3H, m) MS(ESI, m/z): 438(M + H)$^+$ |
| 154 | *-CH₂CH₂-O-C₆H₄-C₆H₃(OMe)-COOH | MS(ESI, m/z): 438(M + H)$^+$ |
| 155 | *-CH₂CH₂-O-C₆H₄-C₆H₃(Me)-COOH | MS(ESI, m/z): 422(M + H)$^+$ |
| 156 | *-CH₂CH₂-O-C₆H₄-C₆H₃(iPr)-COOH | MS(ESI, m/z): 450(M + H)$^+$ |

TABLE 3-continued

| Compound No | R | ¹H-NMR (δ ppm), MS(m/z) |
|---|---|---|
| 157 | [4'-(2-*oxy)ethyl-2-trifluoromethyl-4-carboxybiphenyl] | MS(ESI, m/z): 476(M + H)⁺ |
| 158 | [4'-(2-*oxy)ethyl-3-ethyl-4-carboxybiphenyl] | MS(ESI, m/z): 436(M + H)⁺ |
| 159 | [4'-(2-*oxy)ethyl-3-propyl-4-carboxybiphenyl] | MS(ESI, m/z): 450(M + H)⁺ |
| 160 | [4'-(2-*oxy)ethyl-2-propyl-4-carboxybiphenyl] | MS(ESI, m/z): 450(M + H)⁺ |
| 161 | [4'-(2-*oxy)ethyl-3-sec-butyl-4-carboxybiphenyl] | MS(ESI, m/z): 464(M + H)⁺ |
| 162 | [4'-(2-*oxy)ethyl-3-cyclopentyl-4-carboxybiphenyl] | MS(ESI, m/z): 476(M + H)⁺ |

TABLE 3-continued

| Compound No | R | $^1$H-NMR ($\delta$ ppm), MS(m/z) |
|---|---|---|
| 163 | *-CH2CH2-O-(4-phenyl)-(3-methyl-4-carboxyphenyl) | MS(ESI, m/z): 422(M + H)$^+$ |
| 164 | *-CH2CH2-O-(4-phenyl)-(3-chloro-4-carboxyphenyl) | MS(ESI, m/z): 442(M + H)$^+$ |
| 165 | *-CH2CH2-O-(4-phenyl)-(3-fluoro-4-carboxyphenyl) | MS(ESI, m/z): 426(M + H)$^+$ |
| 166 | *-CH2CH2-O-(4-phenyl)-(2-fluoro-5-carboxyphenyl) | MS(ESI, m/z): 426(M + H)$^+$ |
| 167 | *-CH2CH2-O-(4-phenyl)-(3-isopropyl-4-(carboxymethoxy)phenyl) | MS(ESI, m/z): 480(M + H)$^+$ |
| 168 | *-CH2CH2-O-(4-phenyl)-(3-isopropyl-4-carboxyphenyl) | MS(ESI, m/z): 450(M + H)$^+$ |

TABLE 3-continued

| Compound No | R | $^1$H-NMR ($\delta$ ppm), MS(m/z) |
|---|---|---|
| 169 | | MS(ESI, m/z): 422(M + H)$^+$ |
| 170 | | MS(ESI, m/z): 442(M + H)$^+$ |
| 171 | | MS(ESI, m/z): 500(M + H)$^+$ |
| 172 | | MS(ESI, m/z): 530(M + H)$^+$ |

TABLE 3-continued

| Compound No | R | ¹H-NMR (δ ppm), MS(m/z) |
|---|---|---|
| 173 | [4'-(2-*oxy)ethyl-3-(4-chlorophenoxy)-biphenyl-4-carboxylic acid] | MS(ESI, m/z): 534(M + H)⁺ |
| 174 | [4'-(2-*oxy)ethyl-3-(4-fluorophenoxy)-biphenyl-4-carboxylic acid] | MS(ESI, m/z): 518(M + H)⁺ |
| 175 | [4'-(2-*oxy)ethyl-3-(4-methylphenoxy)-biphenyl-4-carboxylic acid] | MS(ESI, m/z): 514(M + H)⁺ |
| 176 | [4'-(2-*oxy)ethyl-3-methoxy-biphenyl-4-carboxylic acid] | MS(ESI, m/z): 438(M + H)⁺ |

TABLE 3-continued

[Structure: HO-C6H4-CH(OH)-CH(CH3)-NH-R]

| Compound No | R | $^1$H-NMR (δ ppm), MS(m/z) |
|---|---|---|
| 177 | [*-CH2CH2-O-C6H4-C6H3(OEt)-COOH] | MS(ESI, m/z): 452(M + H)$^+$ |
| 178 | [*-CH2CH2-O-C6H4-C6H2(CH3)2-COOCH3] | CD$_3$OD: 1.14–1.18 (3H, m), 2.24 (3H, s), 2.54 (3H, s), 3.32–3.45 (3H, m), 3.88 (3H, s), 4.19–4.33 (2H, m), 4.85–4.90(1H, m), 6.78–6.82(2H, m), 7.02 (2H, d, J=8.4 Hz), 7.10 (1H, s), 7.22 (2H, d, J=8.4 Hz), 7.25–7.29 (2H, m), 7.79 (1H, s) |
| 179 | [*-CH2CH2-O-C6H4-C6H2(CH3)2-COOH] | CD$_3$OD: 1.17 (3H, d, J=6.7 Hz), 2.24 (3H, s), 2.54 (3H, s), 3.51–3.65 (3H, m), 4.39 (2H, t, J=5.1 Hz), 5.13 (1H, d, J=3.1 Hz), 6.82 (2H, d, J=8.6 Hz), 7.07 (1H, s), 7.10 (2H, d, J=8.6 Hz), 7.25 (2H, d, J=8.6 Hz), 7.30 (2H, d, J=8.6 Hz), 7.77 (1H, s) | wherein * in R groups represents their connecting positions

EXAMPLE 12

4'-{(1S,2R)-2-[2-Hydroxy-2-(4-hydoxyphenyl)-1-methylethyl-amino]ethoxy}-2,5-dimethylbiphenyl-4-carboxylic acid (compound 179)

The title compound was prepared as a gray amorphous according to procedures analogous to those as described in Step 3 in Example 9 by using methyl 4'-{(1S,2R)-2-[2-hydroxy-2-(4-hydroxyphenyl)-1-methylethylamino]ethoxy}-2,5-dimethylbiphenyl-4-carboxylate (compound 178). The structure and physical data were shown in table 3.

EXAMPLE 13

4'-{2-[(1S,2R)-2-Hydroxy-2-(4-hydroxyphenyl)-1-methylethyl-amino]ethoxy}-3',5'-dimethylbiphenyl-4-carboxylic acid hydrochloride (compound 180)

A 4 mol/L solution of hydrogen chloride in 1,4-dioxane (0.1 mL) was added to a suspension of 4'-{2-[(1S,2R)-2-hydroxy-2-(4-hydroxyphenyl)-1-methylethylamino]ethoxy}-3',5'-dimethylbiphenyl-4-carboxylic acid (compound 1, 0.089 g) in 1,4-dioxane (11.0 mL), and the mixture was stirred at room temperature for 30 min. The clear solution was diluted with an excess amount of diethyl ether, and stirred at that temperature for 1 hr. The precipitate was collected by filtration to afford the title compound (0.083 g) as a gray amorphous. The structure and physical data were shown in table 4.

EXAMPLE 14

4'-{2-[(1S,2R)-2-Hydroxy-2-(4-hydroxyphenyl)-1-methylethyl-amino]ethoxy}-3-isopropyl-3',5'-dimethylbiphenyl-4-carboxylic acid hydrochloride (compound 181)

The title compound was prepared as a gray amorphous according to procedures analogous to those described in Example 13 by using 4'-{2-[(1S,2R)-2-hydroxy-2-(4-hydroxyphenyl)-1-methylethylamino]ethoxy}-3-isopropyl-3',5'-dimethyl-biphenyl-4-carboxylic acid (compound 4). The structure and physical data were shown in table 4.

EXAMPLE 15

4'-{2-[(1S,2R)-2-Hydroxy-2-(4-hydroxyphenyl)-1-methylethyl-amino]ethoxy}-3',5'-dimethylbiphenyl-4-carboxylic acid p-toluenesulfonate (compound 182)

p-Toluenesulfonic acid monohydrate (0.042 g) was added to a suspension of 4'-{2-[(1S,2R)-2-hydroxy-2-(4-hydroxyphenyl)-1-methylethylamino]ethoxy}-3',5'-dimethylbiphenyl-4-carboxylic acid (compound 1, 0.094 g) in 1,4-dioxane (1.1 mL), and the mixture was stirred at room temperature for 1 hr. The clear solution was diluted with an excess amount of diethyl ether, and the precipitate was collected by filtration to afford the title compound (0.059 g) as a white amorphous. The structure and physical data were shown in table 4.

EXAMPLE 16

4'-{2-[(1S,2R)-2-Hydroxy-2-(4-hydroxyphenyl)-1-methylethyl-amino]ethoxy}-3',5'-dimethylbiphenyl-4-carboxylic acid hydrobromide (compound 183)

To a suspension of 4'-{2-[(1S,2R)-2-hydroxy-2-(4-hydroxyphenyl)-1-methylethylamino]ethoxy}-3',5'-dimethyl-biphenyl-4-carboxylic acid (compound 1, 0.079 g) in 1,4-dioxane (0.91 mL) was added 47% hydrobromic acid (0.042 mL), and the mixture was stirred at room temperature for 10 min. The clear solution was diluted with an excess amount of diethyl ether, and the precipitate was collected by filtration to afford the title compound (0.037 g) as a pale brown amorphous. The structure and physical data were shown in table 4.

EXAMPLE 17

4'-{2-[(1S,2R)-2-Hydroxy-2-(4-hydroxyphenyl)-1-methylethyl-amino]ethoxy}-3-isopropyl-3',5'-dimethylbiphenyl-4-carboxylic acid p-toluenesulfonate (compound 184)

The title compound was prepared as a white amorphous according to procedures analogous to those as described in Example 15 by using 4'-{2-[(1S,2R)-2-hydroxy-2-(4-hydroxy-phenyl)-1-methylethylamino]ethoxy}-3-isopropyl-3',5'-dimethylbiphenyl-4-carboxylic acid (compound 4). The structure and physical data were shown in table 4.

EXAMPLE 18

The following compounds 185-192 were prepared according to procedures analogous to those as described in Examples 13-17. Their structures and physical data were shown in table 4.

TABLE 4

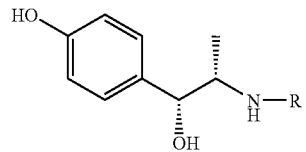

| Compound No | R | $^1$H-NMR (δ ppm), MS(m/z) |
|---|---|---|
| 180 | 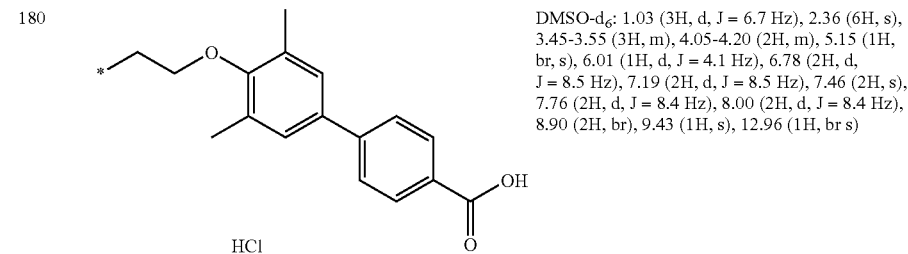 HCl | DMSO-d$_6$: 1.03 (3H, d, J = 6.7 Hz), 2.36 (6H, s), 3.45-3.55 (3H, m), 4.05-4.20 (2H, m), 5.15 (1H, br s), 6.01 (1H, d, J = 4.1 Hz), 6.78 (2H, d, J = 8.5 Hz), 7.19 (2H, d, J = 8.5 Hz), 7.46 (2H, s), 7.76 (2H, d, J = 8.4 Hz), 8.00 (2H, d, J = 8.4 Hz), 8.90 (2H, br), 9.43 (1H, s), 12.96 (1H, br s) |
| 181 | 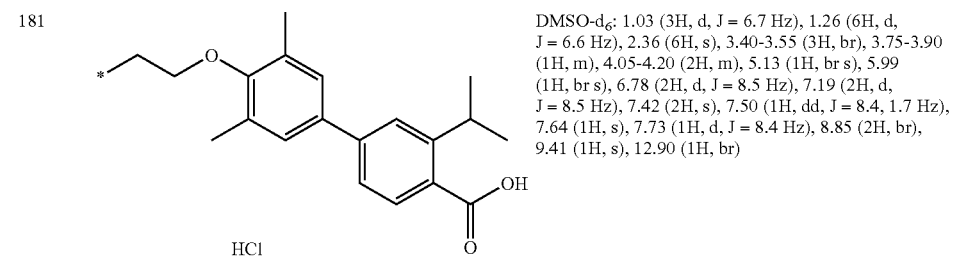 HCl | DMSO-d$_6$: 1.03 (3H, d, J = 6.7 Hz), 1.26 (6H, d, J = 6.6 Hz), 2.36 (6H, s), 3.40-3.55 (3H, br), 3.75-3.90 (1H, m), 4.05-4.20 (2H, m), 5.13 (1H, br s), 5.99 (1H, br s), 6.78 (2H, d, J = 8.5 Hz), 7.19 (2H, d, J = 8.5 Hz), 7.42 (2H, s), 7.50 (1H, dd, J = 8.4, 1.7 Hz), 7.64 (1H, s), 7.73 (1H, d, J = 8.4 Hz), 8.85 (2H, br), 9.41 (1H, s), 12.90 (1H, br) |

TABLE 4-continued

| Compound No | R | ¹H-NMR (δ ppm), MS(m/z) |
|---|---|---|
| 182 | (3,5-dimethyl-4-(ethoxy)biphenyl-4'-carboxylic acid substituent) with p-toluenesulfonic acid | DMSO-d₆: 1.02 (3H, d, J = 6.7 Hz), 2.29 (3H, s), 2.36 (6H, s), 3.45-3.55 (3H, m), 4.05-4.15 (2H, m), 5.12 (1H, br s), 6.02 (1H, d, J = 4.0 Hz), 6.78 (2H, d, J = 8.5 Hz), 7.11 (2H, d, J = 7.9 Hz), 7.19 (2H, d, J = 8.5 Hz), 7.46 (2H, s), 7.47 (2H, d, J = 7.9 Hz), 7.76 (2H, d, J = 8.4 Hz), 8.00 (2H, d, J = 8.4 Hz), 8.75 (2H, br), 9.41 (1H, s), 12.96 (1H, br s) |
| 183 | (3,5-dimethyl-4-(ethoxy)biphenyl-4'-carboxylic acid substituent) HBr | DMSO-d₆: 1.02 (3H, d, J = 6.7 Hz), 2.36 (6H, s), 3.40-3.55 (3H, m), 4.05-4.15 (2H, m), 5.11 (1H, br s), 6.02 (1H, br s), 6.78 (2H, d, J = 8.5 Hz), 7.19 (2H, d, J = 8.5 Hz), 7.47 (2H, s), 7.76 (2H, d, J = 8.7 Hz), 8.00 (2H, d, J = 8.7 Hz), 8.75 (2H, br), 9.41 (1H, br s), 12.96 (1H, br) |
| 184 | (3,5-dimethyl-4-ethoxy biphenyl with isopropyl carboxylic acid substituent) with p-toluenesulfonic acid | DMSO-d₆: 1.03 (3H, d, J = 6.7 Hz), 1.26 (6H, d, J = 6.8 Hz), 2.28 (3H, s), 2.36 (6H, s), 3.40-3.55 (3H, br), 3.75-3.90 (1H, m), 4.00-4.15 (2H, m), 5.10 (1H, br s), 5.99 (1H, br s), 6.78 (2H, d, J = 8.5 Hz), 7.10 (2H, d, J = 7.9 Hz), 7.19 (2H, d, J = 8.5 Hz), 7.42 (2H, s), 7.47 (2H, d, J = 7.9 Hz), 7.49 (1H, J = 8.0, 1.7 Hz), 7.63 (1H, d, J = 1.7 Hz), 7.73 (1H, d, J = 8.0 Hz), 8.70 (2H, br), 9.39 (1H, s), 12.87 (1H, br s) |
| 185 | (3,5-dimethyl-4-ethoxy biphenyl with isopropyl carboxylic acid substituent) HBr | DMSO-d₆: 1.03 (3H, d, J = 7.0 Hz), 1.27 (6H, d, J = 7.1 Hz), 2.36 (6H, s), 3.45-3.55 (3H, br), 3.75-3.85 (1H, m), 4.00-4.15 (2H, m), 5.12 (1H, br s), 6.00 (1H, d, J = 4.3 Hz), 6.78 (2H, d, J = 8.7 Hz), 7.20 (2H, d, J = 8.7 Hz), 7.42 (2H, s), 7.50 (1H, dd, J = 8.2, 2.1 Hz), 7.63 (1H, d, J = 2.1 Hz), 7.73 (1H, d, J = 8.2 Hz), 8.70 (1H, br), 8.75 (1H, br), 9.39 (1H, s), 12.87 (1H, br) |
| 186 | (2,6-dimethyl biphenyl-4'-carboxylic acid with ethoxy substituent) HCl | DMSO-d₆: 0.99 (3H, d, J = 6.5 Hz), 1.97 (6H, s), 3.35-3.50 (3H, m), 4.25-4.35 (2H, m), 5.00-5.10 (1H, m), 5.90-6.05 (1H, m), 6.77 (2H, d, J = 8.5 Hz), 6.79 (2H, s), 7.18 (2H, d, J = 8.5 Hz), 7.25 (2H, d, J = 7.9 Hz), 8.01 (2H, d, J = 7.9 Hz), 8.50-8.90 (2H, br), 9.40 (1H, s), 12.9 (1H, br) |

TABLE 4-continued

| Compound No | R | ¹H-NMR (δ ppm), MS(m/z) |
|---|---|---|
| 187 | (3,5-dimethyl-4-(2-*oxy)ethoxy)-2'-methoxy-biphenyl-4'-carboxylic acid substituent)·HCl | DMSO-d₆: 1.04 (3H, d, J = 6.6 Hz), 2.32 (6H, s), 3.40-3.55 (3H, m), 3.83 (3H, s), 4.05-4.25 (2H, m), 5.17 (1H, br s), 5.99 (1H, br s), 6.78 (2H, d, J = 8.5 Hz), 7.15-7.25 (4H, m), 7.37 (1H, d, J = 7.7 Hz), 7.55-7.65 (2H, m), 8.95 (2H, br), 9.41 (1H, br s), 13.00 (1H, br s) |
| 188 | (3-methyl-4-(2-*oxy)ethoxy)-2'-ethyl-biphenyl-4'-carboxylic acid substituent)·HCl | DMSO-d₆: 1.03 (3H, d, J = 6.7 Hz), 1.06 (3H, t, J = 7.5 Hz), 2.25 (3H, s), 2.62 (2H, q, J = 7.5 Hz), 3.45-3.55 (3H, m), 4.37 (2H, br s), 5.08 (1H, br s), 6.00 (1H, br s), 6.77 (2H, d, J = 8.5 Hz), 7.06 (1H, d, J = 9.0 Hz), 7.10-7.20 (4H, m), 7.24 (1H, d, J = 7.9 Hz), 7.79 (1H, dd, J = 7.9, 1.7 Hz), 7.89 (1H, s), 8.80 (2H, br), 9.40 (1H, s), 12.86 (1H, br) |
| 189 | (3-methyl-4-(2-*oxy)ethoxy)-2'-isopropoxy-biphenyl-4'-carboxylic acid substituent)·HCl | DMSO-d₆: 1.03 (3H, d, J = 6.7 Hz), 1.24 (6H, d, J = 6.0 Hz), 2.25 (3H, s), 3.40-3.60 (3H, m), 4.35-4.45 (2H, m), 4.55-4.70 (1H, m), 5.10 (1H, br s), 6.01 (1H, d, J = 4.0 Hz), 6.77 (2H, d, J = 8.5 Hz), 7.03 (1H, d, J = 8.7 Hz), 7.19 (2H, d, J = 8.5 Hz), 7.35-7.45 (3H, m), 7.50-7.60 (2H, m), 8.80 (1H, br), 8.90 (1H, br), 9.41 (1H, s), 12.95 (1H, br s) |
| 190 | (2-methyl-4-(2-*oxy)ethoxy)-2'-isopropoxy-biphenyl-4'-carboxylic acid substituent)·HCl | DMSO-d₆: 1.01 (3H, d, J = 6.7 Hz), 1.15 (6H, d, J = 5.3 Hz), 2.09 (3H, s), 3.40-3.55 (3H, m), 4.30-4.40 (2H, m), 4.50-4.60 (1H, m), 5.11 (1H, br s), 5.96 (1H, br s), 6.77 (2H, d, J = 8.6 Hz), 6.87 (1H, dd, J = 8.4, 2.5 Hz), 6.91 (1H, d, J = 2.5 Hz), 7.07 (1H, d, J = 8.4 Hz), 7.15-7.25 (3H, m), 7.55 (1H, d, J = 1.4 Hz), 7.57 (1H, dd, J = 7.7, 1.4 Hz), 8.85 (2H, br), 9.41 (1H, s), 12.95 (1H, br) |
| 191 | (4-(2-*oxy)ethoxy)-2'-isopropyl-biphenyl-4'-carboxylic acid substituent)·HCl | DMSO-d₆: 1.01 (3H, d, J = 6.7 Hz), 1.14 (6H, d, J = 6.8 Hz), 3.00-3.10 (1H, m), 3.40-3.55 (3H, m), 4.30-4.40 (2H, m), 5.08 (1H, br s), 5.97 (1H, br s), 6.77 (2H, d, J = 8.5 Hz), 7.10 (2H, d, J = 8.5 Hz), 7.19 (2H, d, J = 8.5 Hz), 7.24 (1H, d, J = 7.9 Hz), 7.29 (2H, d, J = 8.5 Hz), 7.78 (1H, dd, J = 7.9, 1.7 Hz), 7.97 (1H, d, J = 1.7 Hz), 8.70 (1H, br), 8.80 (1H, br), 9.39 (1H, s), 12.95 (1H, br) |

TABLE 4-continued

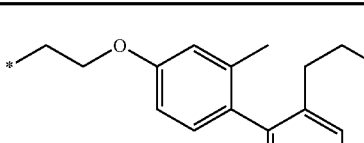

| Compound No | R | $^1$H-NMR (δ ppm), MS(m/z) |
|---|---|---|
| 192 | 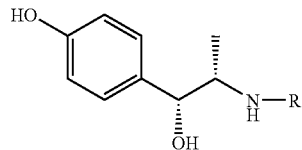 HCl | DMSO-$d_6$: 0.73 (3H, t, J = 7.3 Hz), 1.01 (3H, d, J = 6.6 Hz), 1.30-1.45 (2H, m), 1.99 (3H, s), 2.20-2.35 (2H, m), 3.40-3.55 (3H, br), 4.35 (2H, br s), 5.09 (1H, br s), 5.97 (1H, d, J = 4.0 Hz), 6.77 (2H, d, J = 8.3 Hz), 6.85-6.95 (1H, m), 6.96 (1H, br s), 7.06 (1H, d, J = 8.3 Hz), 7.15 (1H, d, J = 7.9 Hz), 7.19 (2H, d, J = 8.3 Hz), 7.80 (1H, d, J = 7.9 Hz), 7.89 (1H, s), 8.73 (1H, br), 8.83 (1H, br), 9.40 (1H, s), 12.90 (1H, br) | wherein * in R groups represents their connecting positions

TEST EXAMPLE 1

Measurement of Agonistic Activities on Human β-Adrenoceptors

1. Measurement of Agonistic Activities on Human β3-Adrenoceptor

Test compounds were dissolved in 50% dimethyl sulfoxide to make a $10^{-2}$ M solution. Then, a series of 1:10 dilutions containing a maximal dose of $1\times10^{-4}$ M were prepared using D-PBS (−) (Gibco-BRL: LIFE TECHNOLOGIES). The series were used for a testing sample to measure activity. SK-N-MC cells (American Type Culture Collection, $1\times10^5$ cell/mL) were put in 96 well plates by 100 μL and were cultured for about 24 hours. Forty μL of D-PBS (−) and 20 μL of CGP-20712A (FUNAKOSHI, $3\times10^{-6}$ mol/L D-PBS (−) solution) were added in them and incubated for 20 minutes. After that, 20 μL of 3-isobutyl-1-methylxanthine (SIGMA, $1\times10^{-2}$ mol/L D-PBS (−) solution) and 20 μL of testing sample were added in them and they were incubated under an atmosphere of 5% $CO_2$ at 37° C. for 30 minutes. cAMP concentrations accumulated in cells were reacted in cAMP-Screen (Applied Biosystems) and were detected by Microplate LuminometerTR717 (Applied Biosystems). The maximum reaction of isoproterenol, a positive contrast, was taken as a 100%, and the concentration of a test compound which gave reaction of the 50% was calculated as a $EC_{50}$ value. In addition, the ratio of the maximum reaction of the test compound against the maximum reaction of isoproterenol was calculated as an intrinsic activity (I.A.). Isoproterenol was examined as a contrast example, and (R)-3'-[[2-[[2-(3-chlorophenyl)-2-hydroxyethyl]aminoethoxy]-[1,1'-biphenyl]-3-carboxylic acid which was described in example 17 on WO99/65877 was also examined as a comparison example. The results were shown in table 5.

2. Measurement of Agonistic Activities on Human β1- and β2-Adrenoceptors

1) Preparation of Human β1- and β2-Adrenoceptor Expression Plasmid Vector (1) Human β1-Adrenoceptor Both ends of a domain including full length of human β1-adrenoceptor were amplified on the basis of DNA base information that is registered with GenBank/EMBL data base as Accession No. J03019. DNA fragment which was amplified was inserted into a vector for cloning and amplified in Escherichia coli bacteria. The plasmid which was cloned was inserted into a vector pCI-neo (Promega) for protein expression and plasmid DNA was extracted and purified, then it was used for a preparation of the following expression cells.

(2) Human β2-Adrenoceptor

The primer which added a restriction enzyme recognition region to 5' end was designed on the basis of the base information that is registered with GenBank/EMBL data base as Accession No. M15169, and the clone was obtained by performance of PCR using human bladder origin cDNA as a template. The clone was inserted into pGEM-T vector and was amplified in Escherichia coli bacteria as a plasmid, and it was purified and the sequence of full length and around of insertion sequence determined by means of 310 Genetic Analyzer (ABI). The cloned DNA fragment did not differ from the base information registered with a GenBank/EMBL database.

2) Preparation of Human β1- and β2-Adrenoceptor Expressed Cells (1) Preparation of Human β1-Adrenoceptor Expressed Cells The plasmid (320 ng) for expression which was obtained in the previous section was transfected into $5\times10^4$ CHO cells suspended in DMEM (Gibco-BRL: LIFE TECHNOLOGIES) containing 10% fetal bovine serum (Sanko Junyaku) by means of Lipofectoamine 2000 (Invitrogen). These cells were dispensed in 96 well plate by $5\times10^4$ cells/100 μL per well and were cultured under an atmosphere of 5% $CO_2$ at 37° C. for 24 hours, and were used for the assay.

(2) Preparation of Human β2-Adreoceptor Expressed Cells

The plasmid (80 ng) for expression obtained in the previous section was transfected into $5\times10^4$ CHO cells suspended in DMEM containing 10% fetal bovine serum by means of Lipofectoamine2000. These cells were dispensed in 96 well plate by $5\times10^4$ cells/100 μL per well and were cultured under an atmosphere of 5% $CO_2$ at 37° C. for 24 hours, and were used for the assay.

3) Measurement of Agonistic Activities on Human β1- and β2-Adrenoceptors

Test compounds were dissolved in 50% dimethyl sulfoxide to make a $10^{-2}$ M solution. Then, a series of 1:10 dilutions containing a maximal dose of $2\times10^{-4}$ M were prepared using D-PBS (−). The series were used for a testing sample to measure activity. The culture medium of CHO cells of previous section was removed and washed twice with 200 μL D-PBS (−) per well. After that, 50 μL of 3-isobutyl-1-methylxanthine (SIGMA, 1 mM) was added and leaved at rest for 5 minutes, and 50 μL of testing sample were added in them and they were incubated under an atomosphere of 5% $CO_2$ at 37° C. for 30 minutes. cAMP concentrations accumulated in cells were reacted in cAMP-Screen and were detected by Microplate LuminometerTR717. The maximum reaction of isoproterenol, a positive contrast, was taken as a 100%, and the concentration of a test compound which gave reaction of the 50% was calculated as a $EC_{50}$ value. In addition, the ratio of the maximum reaction of the test compound against the maximum reaction of isoproterenol was calculated as an intrinsic activity (I.A.). Isoproterenol was examined as a contrast example, and (R)-3'-[[2-[[2-(3-chlorophenyl)-2-hydroxyethyl]amino-ethoxy]-[1,1'-biphenyl]-3-carboxylic acid which was described in example 17 on WO99/65877 was also examined as a comparison example. The results were shown in table 5.

TABLE 5

| Compound No. | β3 receptor | | β2 receptor | | β1 receptor | |
|---|---|---|---|---|---|---|
| | $EC_{50}$ (μM) | I.A. (%) | $EC_{50}$ (μM) | I.A. (%) | $EC_{50}$ (μM) | I.A. (%) |
| 4 | 0.24 | 94 | 1) | 27 | 1) | 45 |
| 26 | 0.057 | 125 | 1) | 49 | 2.28 | 74 |
| 153 | 0.48 | 97 | 1) | 28 | 4.32 | 57 |
| 156 | 0.025 | 239 | 1) | 27 | 18.86 | 87 |
| 160 | 0.20 | 91 | 1) | 32 | 0.79 | 62 |
| Comparison | >10 | 41 | 1) | 15 | 0.74 | 60 |
| Isoproterenol | 0.064 | 100 | 0.0006 | 100 | 0.0005 | 100 |

1); Intrinsic activities in all concentrations from $10^{-10}$ M to $2 \times 10^{-4}$ M showed below 50%.

As shown in the above table, the compounds of the present invention exhibited potent stimulating activities on human β3-adrenoceptor. Moreover, the compounds of the present invention showed minor stimulating activities on β1- and/or β2-adrenoceptor as compared with those on β3-adrenoceptor.

TEST EXAMPLE 2

Measurement of β-Adrenoceptor Stimulation in Isolated Tissues

1) Measurement of β3-Adrenoceptor Stimulation

The bladder of male ferret (body weight: 1100-1400 g) was isolated and bladder smooth muscle strip about 10 mm in length and 2 mm in width was taken and the experiment was conducted according to a Magnus method. The strip was suspended in a Krebs-Henseleit solution maintained at 37° C. and gassed with a mixed gas of 95% $O_2$ and 5% $CO_2$ and stretched at a tension of 1 g. The bladder resting tension was outputted through an isometric force transducer and recorded on an oscillograph. The test compound was added cumulatively into a Magnus bath by every 5 minutes. Potencies were evaluated that the tension of bladder smooth muscle before the addition of test compounds was taken as a 100%, and the tension induced by $10^{-5}$ M forskolin treatment at which the maximum relaxation occur was taken as a 0%, and the concentration of test compound which gave relaxation of the 50% was taken as a $EC_{50}$ value.

2) Measurement of β1-Adrenoceptor Stimulation

The atrium of male SD rat (body weight 250-400 g) was isolated and the experiment was conducted according to a Magnus method. The preparation was suspended in a Krebs-Henseleit solution maintained at 37° C. and gassed with a mixed gas of 95% $O_2$ and 5% $CO_2$ and stretched at a tension of 0.5 g. The myocardial contractility was outputted through an isometric force transducer and recorded on an oscillograph through a tachometer. The test compound was added cumulatively into a Magunus bath. Potencies were evaluated that the increment of heart rate per minute when isoproterenol was added at 10-8 M was taken as a 100% and the concentration of test compounds which gave increment of the 50% was taken as a $EC_{50}$ value.

3) Measurement of β2-Adrenoceptor Stimulation

The uterus of pregnant SD rat (Day 21 of gestation) was isolated and longitudinal muscle strip, which was avoided placenta attached part, about 15 mm in length and 5 mm in width was taken and the experiment was conducted according to a Magnus method. The preparation was suspended in a Locke-Ringer solution maintained at 37° C. and gassed with a mixed gas of 95% $O_2$ and 5% $CO_2$ and stretched at a tension of 0.5 g. Spontaneous contraction of uterus was outputted through an isometric force transducer and recorded on an oscillograph through a tachometer. The test compound was added cumulatively into a Magnus bath by every 5 minutes. Potencies were evaluated that the sum of uterine contraction for 5 minutes before the addition of test compounds was taken as a 100%, and compared with the sum of uterine contraction for 5 minutes after the addition of each concentration of test compounds. The concentration of test compounds which gave inhibition of the 50% was taken as a $EC_{50}$ value. (R)-3'-[[2-[[2-(3-chlorophenyl)-2-hydroxyethyl]-aminoethoxy]-[1,1'-biphenyl]-3-carboxylic acid which was described in example 17 on WO99/65877 was also examined as a comparison example. The results were shown in table 6.

TABLE 6

| Compound No. | β3 receptor $EC_{50}$ (μM) | β2 receptor $EC_{50}$ (μM) | β1 receptor $EC_{50}$ (μM) |
|---|---|---|---|
| 153 | 0.16 | 2.68 | >10 |
| 156 | 0.16 | 5.87 | >10 |
| Comparison | >10 | >10 | 1.88 |

As shown in the above table, the compounds of the present invention showed minor stimulating activities on β1- and/or β2-adrenoceptor as compared with those on β3-adrenoceptor.

TEST EXAMPLE 3

Transport Study Using Human Intestinal Epithelium Tissue.

1) Preparation of Culture Medium.

Dulbecco's modified Eagle's medium (Invitrogen Life Technologies) containing 10% fetal bovine serum (Sanko Jyunyaku), 1% MEM-nonessential amino acids, 200 mM L-glutamine (Invitrogen Life Technologies), 1% penicillin-streptomycin 10000 units/mL-10000 μg/mL (Invitrogen Life Technologies) was prepared and used as a culture medium.

2) Caco-2 Cell Culture

Caco-2 cells (American Type Culture Collection) were subcultured in a culture flask containing the culture medium.

After removing the culture medium before the cell reaches confluent, Caco-2 cells were washed with Hank's balanced salt solution Ca, Mg Free (Invitrogen Life Technologies). The Caco-2 cells were removed with 0.25% trypsin/1 mM EDTA and were collected centrifugally. The Caco-2 cells were suspended at a density of ca $1.18 \times 10^5$ cells per mL using the culture medium. Then, the Caco-2 cells were placed in a Transwell cell culture chamber (Costar) with a collagen-coated polycarbonate membrane, pore size 3.0 μm, 0.33 cm² surface area and were cultured under an atmosphere of 5% $CO_2$-95% air at 37° C. After cultured for 21-25 days, the values of transepithelial electrical resistance were measured with Millicell-ERS (Millipore) and the cells that showed the numerical value more than 250 O·cm² were used for the following transport study.

3) Transport Study

The culture medium in the inside and outside compartments of the Traswell chamber was removed and replaced by a buffer solution containing 10 mM MES (pH 6.0) or 10 mM HEPES (pH7.4). The medium volume in the inside and outside compartments of the chamber was made at 0.1 mL (pH 6.0) and 0.5 mL (pH 7.4), respectively. The medium of the inside compartment was replaced by a buffer solution (pH 6.0) containing test compounds. For evaluating the transport of the test compounds from the inside compartment to the outside compartment, 100 μL of the outside buffer was sampled after incubating at 37° C. for 1 hr.

The apparent permeability coefficient was calculated as the following equation. The amounts of the test compounds in the outside buffer sampled were divided by incubation time. In addition, the amounts of penetration per incubation time (second) were divided by the concentration of the added test compound and the membrane surface.

$$Papp = \frac{dQ}{dt} \cdot \left(\frac{1}{Co \cdot A}\right)$$

Papp is apparent permeability coefficient. ($\times 10^{-6}$ cm/sec)
dQ/dt is amount of penetration per incubation time.
Co is the initial concentration. (100 μM)
A is the membrane surface area. (0.33 cm²)

The concentrations of test compounds were determined using LC/MS/MS.

1) LC Condition
Device: Alliance 2690 (Waters)
Column: Inertsil ODS3 column (3 μm, 50×4.6 mm, GL science)
Mobile phase: 0.1% acetic acid/acetonitrile (60/40)
Flow rate: 0.2 mL/min
Injection volume: 10 uL 2) MS/MS Condition
Device: API-365 (PE Sciex)
Ionization method: electrospray ionization (ESI)
Detection: detected for the mass of each compounds as $[M+H]^+$, and analyzed for the fragment ion occurred by $N_2$ gas The results were shown in table 7.

TABLE 7

| Compound No | permeability coefficient Caco-2 Papp ($\times 10^{-6}$ cm/s) |
|---|---|
| 3 | 19.9 |
| 4 | 15.7 |
| 156 | 3.4 |
| 160 | 4.0 |
| 162 | 4.0 |
| atenolol | 0.42 |

It has been found that atenolol, which is used as positive control, has standard 50% absorption ratio in human intestine. The compounds of the invention showed higher permeabilities as compared with those of atenolol. Accordingly, it is expected that the compounds of the present invention show adequate oral absorption in human.

TEST EXAMPLE 4

Experiment of Lipolysis in ddY Mice Adipocytes

Epididymal fat tissue of ddY mice (body weight 35 g) was removed and isolated to cells by collagenase (typeI, 1 mg/ml) in a culture medium (Krebs-Henseleit solution inclusive of 3% BSA, 1.2 mM $CaCl_2$ and 25 mM HEPES but exclusive of $NaHCO_3$; pH7.4) maintained at 37° C. After rinsing the cells in the culture medium, 50,000 cells/well were seeded in a 96-well culture plate and were incubated at 37° C. in the presence of various concentration of test compounds. Two hours later, the concentration of free fatty acid in the culture medium was measured and it was made as an index for lipolysis. The concentration of free fatty acid was measured by means of NEFA C-test wako (WAKO). Potency was evaluated that the free fatty acid concentration in the presence of $10^{-6}$ M isoproterenol was taken as a 100%, and the concentration of a test compound which gave the free fatty acid concentration of the 50% was taken as a $EC_{50}$ value.

(R)-3'-[[2-[[2-(3-chlorophenyl)-2-hydroxyethyl]amino-ethoxy]-[1,1'-biphenyl]-3-carboxylic acid which was described in example 17 on WO99/65877 was also examined as a comparison example. The results were shown in table 8.

TABLE 8

| Compound No. | Lipolysis acticity $EC_{50}$ value (nM) |
|---|---|
| 15 | 21.6 |
| 26 | 11.2 |
| 156 | 19.5 |
| Comparison | >1000 |

As a result of these experiments, it was showed that compounds of the present invention have good lipolysis activities.

TEST EXAMPLE 5

Experiment of Measurement of Circulating Free Fatty Acid Concentration and Experiment of Thermogenesis Appropriate doses of compounds of the present invention from 1 μg/kg to 100 mg/kg were orally administered to ddY mice (SLC). After a certain period of time, blood was collected and the blood free fatty acid was measured by means of NEFA C-test wako (WAKO) and rectal temperature was also measured by means of a digital thermometer. As a result, the significant increments of blood free fatty acid concentration and body temperature were observed. Moreover significant and enough increment of body temperature was observed at even the low dosage that a meaningful rise of blood free fatty acid concentration was not observed.

TEST EXAMPLE 6

Effects on Blood Glucose, Plasma Insulin, Plasma Triglyceride, Free Fatty Acid and Glucose Tolerance Effects of compounds of the present invention on blood glucose, plasma insulin, plasma triglyceride, free fatty acid and glucose tolerance may be evaluated as follows. Appropriate dosages of compounds of the present invention from 1 μg/kg to 100 mg/kg are orally administered to KK-Ay/Ta Jcl mice (Clea Japan) once or twice daily for a few weeks or for a few months. Body weight and food consumption are weighed during dosing period. On the day before the dosing period end, the blood is collected and biochemical parameters are measured. The biochemical parameters are blood glucose, plasma insulin, plasma triglyceride and free fatty acid. On the day following the dosing period end, glucose tolerance test is performed by measurement of the changes of blood glucose and plasma insulin values in oral glucose tolerance test.

TEST EXAMPLE 7

Effect on Circulatory Organ

β1- and β2-adrenergic actions of compounds of the present invention were investigated by assuming the changes of heart rate and blood pressure as an index. Polyethylene catheter filled with heparinized saline was inserted into carotid artery of urethane anesthetized SD rat (SLC). Another end of catheter was connected to a pressure transducer and the blood pressure was measured through an amplifier. And the heart rate was determined by tachometer connected to this amplifier. Compounds of the present invention were dissolved in an appropriate solvent and were intravenously administered to SD rats at the dosages from 10 μg/kg as lowest dose to 1 mg/kg as highest dose. After a certain period of time after each dosage of test compound was administered, blood pressure and heart rate were measured and compared with that before compound administration. Those changes were extremely slight. The compounds of the present invention were dissolved in an appropriate solvent and were intravenously administered to pentobarbital anesthetized cynomolgus monkeys at the dosages from 1 ng/kg as lowest dose to 1 mg/kg as highest dose. After a certain period of time after each dosage of test compound was administered, blood pressure and heart rate were measured and compared with that before compound administration. In each dosage, the changes of blood pressure and heart rate were extremely slight as in the case of rats.

As a result of these experiments, it was suggested that effect of compounds of the present invention on cardiac organ was extremely slight and that there was less possibility of adverse effect expression resulted from β1- and β2-adrenergic activation.

TEST EXAMPLE 8

Experiment of Acute Toxicity

Compounds of the present invention were dissolved in an appropriate solvent and were intravenously administered to SD rats (SLC) at a dose of 400 mg/kg. In all cases there was no death and it was suggested that compounds of the present invention had low toxicity.

INDUSTRIAL APPLICABILITY

Compounds represented by general formula (I) of the present invention exhibit potent stimulating activities on human β3-adrenoceptors, and are accordingly suitable for the treatment or prophylaxis of obesity, diabetes mellitus, hyperlipidemia, depression, urinary dysfunctions, diseases caused by biliary calculus or biliary tract hypermotility, or diseases caused by intestinal hypermotility.

The invention claimed is:
1. A compound represented by general formula (I):

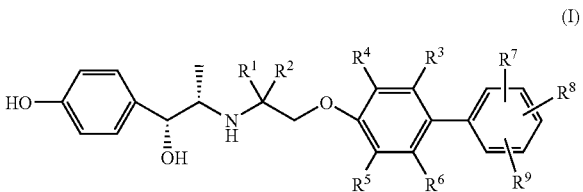

a prodrug thereof, or a pharmaceutically acceptable salt thereof,
wherein
each of $R^1$ and $R^2$ is independently a hydrogen atom or a lower alkyl group; each of $R^3$, $R^4$, $R^5$ and $R^6$ is independently a hydrogen atom, a halogen atom, a lower alkyl group or a lower alkoxy group;
each of $R^7$ and $R^8$ is independently a hydrogen atom, a halogen atom, a lower alkyl group, a halo-lower alkyl group, a hydroxy-lower alkyl group, a cycloalkyl group, a heterocycloalkyl group, a lower alkoxy group, a di(lower alkyl)amino group, a cyclic amino group, a di(lower alkyl)amino-lower alkyl group, an aryl group, an aryloxy group, an aralkyloxy group, a heteroaryl group, a cyano group, a hydroxyl group, a lower acyl group, a lower alkylsulfanyl group, a lower alkylsulfonyl group, a carboxy group, a lower alkoxycarbonyl group or an aralkyloxycarbonyl group, or when $R^7$ and $R^8$ are adjacent each other, $R^7$ and $R^8$ are bonded together to form —O—$(CH_2)_m$—O—, —O—$(CH_2)_n$— or —$(CH_2)_p$—,
wherein m is an integer of 1 to 3,
n is an integer of 2 to 4,
p is an integer of 3 to 5;
$R^9$ is —C(O)—$R^{10}$, -$A^1$-C(O)—$R^{10}$, —O-$A^2$-C(O)—$R^{10}$ or a tetrazol-5-yl group,
wherein $R^{10}$ is a hydroxyl group, a lower alkoxy group, an aralkyloxy group or —$NR^{11}R^{12}$,
each of $R^{11}$ and $R^{12}$ is independently a hydrogen atom, a lower alkyl group, a carboxy-lower alkyl group or a lower alkoxycarbonyl-lower alkyl group, or $R^{11}$ and $R^{12}$, together with the nitrogen atom to which they are bonded, form a cyclic amine,
$A^1$ is a lower alkylene group or a lower alkenylene group, and
$A^2$ is a lower alkylene group.
2. The compound according to claim 1, or a pharmaceutically acceptable salt thereof, wherein
$R^1$ and $R^2$ are a hydrogen atom;
each of $R^7$ and $R^8$ is independently a hydrogen atom, a halogen atom, a lower alkyl group, a halo-lower alkyl group, a cycloalkyl group, a lower alkoxy group, an aryloxy group, a lower alkylsulfanyl group, a hydroxyl group or a lower acyl group;
$R^9$ is —C(O)—$R^{10}$ or —$OCH_2C(O)$—$R^{10}$; and $R^{10}$ is a hydroxyl group, a lower alkoxy group or an aralkyloxy group; provided that at least one of $R^3$, $R^4$, $R^5$ and $R^6$ is a halogen atom, a lower alkyl group or a lower alkoxy group.

3. The compound according to claim 2, or a pharmaceutically acceptable salt thereof wherein $R^9$ is bonded in the para-position with respect to the biphenyl bond.

4. The compound according to claim 3, or a pharmaceutically acceptable salt thereof, wherein
   $R^7$ is a hydrogen atom; and
   $R^8$ is a hydrogen atom, a halogen atom, a lower alkyl group, a cycloalkyl group, a lower alkoxy group, an aryloxy group, a hydroxyl group or a lower acyl group.

5. The compound according to claim 4, or a pharmaceutically acceptable salt thereof, wherein
   $R^3$ and $R^6$ are a hydrogen atom;
   $R^4$ is a hydrogen atom, a halogen atom or a lower alkyl group; and
   $R^5$ is a halogen atom or a lower alkyl group.

6. The compound according to claim 4, or a pharmaceutically acceptable salt thereof, wherein
   $R^3$ is a halogen atom or a lower alkyl group;
   $R^4$ and $R^6$ are a hydrogen atom; and
   $R^5$ is a hydrogen atom, a halogen atom or a lower alkyl group.

7. The compound according to claim 2, or a pharmaceutically acceptable salt thereof, wherein $R^9$ is bonded in the meta-position with respect to the biphenyl bond.

8. The compound according to claim 7, or a pharmaceutically acceptable salt thereof, wherein
   $R^7$ is a hydrogen atom; and
   $R^8$ is a halogen atom or a lower alkoxy group.

9. The compound according to claim 8, or a pharmaceutically acceptable salt thereof, wherein
   $R^3$ and $R^6$ are a hydrogen atom;
   $R^4$ is a hydrogen atom or a lower alkyl group; and
   $R^5$ is a lower alkyl group.

10. The compound according to claim 1, or a pharmaceutically acceptable salt thereof, wherein
    $R^1$, $R^2$, $R^3$, $R^4$, $R^5$ and $R^6$ are a hydrogen atom, each of $R^7$ and $R^8$ is independently a hydrogen atom, a halogen atom, a lower alkyl group, a halo-lower alkyl group, a cycloalkyl group, a lower alkoxy group or an aryloxy group;
    $R^9$ is —C(O)—$R^{10}$ or —OCH$_2$C(O)—$R^{10}$; and
    $R^{10}$ is a hydroxyl group, a lower alkoxy group or an aralkyloxy group.

11. The compound according to claim 10, or a pharmaceutically acceptable salt thereof, wherein $R^9$ is bonded in the para-position with respect to the biphenyl bond.

12. The compound according to claim 11, or a pharmaceutically acceptable salt thereof, wherein
    $R^7$ is a hydrogen atom; and
    $R^8$ is a halogen atom, a lower alkyl group, a halo-lower alkyl group, a cycloalkyl group, a lower alkoxy group or an aryloxy group.

13. The compound according to claim 1, a lower alkyl ester thereof, or a pharmaceutically acceptable salt thereof, selected from the group consisting of 4'-{2-[(1S,2R)-2-hydroxy-2-(4-hydroxyphenyl)-1-methylethylamino]ethoxy}-2,3',5'-trimethylbiphenyl-4-carboxylic acid;

4'-{2-[(1S,2R)-2-hydroxy-2-(4-hydroxyphenyl)-1-methylethylamino]ethoxy}-3-isopropyl-3',5'-dimethylbiphenyl-4-carboxylic acid;

(3-acetyl-4'-{2-[(1S,2R)-2-hydroxy-2-(4-hydroxyphenyl)-1-methylethylamino]ethoxy}-3',5'-dimethylbiphenyl-4-yloxy)acetic acid;

4'-{2-[(1R,2S)-2-hydroxy-2-(4-hydroxyphenyl)-1-methylethylamino]ethoxy}-2,2'-dimethylbiphenyl-4-caboxylic acid;

2-ethyl-4'-{2-[(1S,2R)-2-hydroxy-2-(4-hydroxyphenyl)-1-methylethylamino]ethoxy}-2'-methylbiphenyl-4-carboxylic acid;

4'-{2-[(1S,2R)-2-hydroxy-2-(4-hydroxyphenyl)-1-methylethylamino]ethoxy}-2-isopropyl-2'-methylbiphenyl-4-carboxylic acid;

4'-{2-[(1S,2R)-2-hydroxy-2-(4-hydroxyphenyl)-1-methylethylamino]ethoxy}-2'-methyl-2-propylbiphenyl-4-carboxylic acid;

4'-{2-[(1R,2S)-2-hydroxy-2-(4-hydroxyphenyl)-1-methylethylamino]ethoxy}-2-methoxy-3',5'-dimethylbiphenyl-4-carboxylic acid;

4'-{2-[(1R,2S)-2-hydroxy-2-(4-hydroxyphenyl)-1-methylethylamino]ethoxy}-3',5'-dimethyl-2-propylbiphenyl-4-carboxylic acid;

2-ethyl-4'-{2-[(1R,2S)-2-hydroxy-2-(4-hydroxyphenyl)-1-methylethylamino]ethoxy}-3'-methylbiphenyl-4-carboxylic acid;

4'-{2-[(1R,2S)-2-hydroxy-2-(4-hydroxyphenyl)-1-methylethylamino]ethoxy}-3'-methyl-2-propylbiphenyl-4-carboxylic acid;

3-cyclopentyl-4'-{2-[(1R,2S)-2-hydroxy-2-(4-hydroxyphenyl)-1-methylethylamino]ethoxy}-3'-methylbiphenyl-4-carboxylic acid;

2-ethyl-3'-fluoro-4'-{2-[(1R,2S)-2-hydroxy-2-(4-hydroxyphenyl)-1-methylethylamino]ethoxy}biphenyl-4-carboxylic acid;

3'-fluoro-4'-{2-[(1R,2S)-2-hydroxy-2-(4-hydroxyphenyl)-1-methylethylamino]ethoxy}-2-isopropylbiphenyl-4-carboxylic acid;

3'-fluoro-4'-{2-[(1R,2S)-2-hydroxy-2-(4-hydroxyphenyl)-1-methylethylamino]ethoxy}-2-propylbiphenyl-4-carboxylic acid;

(4'-{2-[(1S,2R)-2-hydroxy-2-(4-hydroxyphenyl)-1-methylethylamino]ethoxy}-2,3',5'-trimethylbiphenyl-4-yloxy) acetic acid;

3-hyroxy-4'-{2-[(1S,2R)-2-hydroxy-2-(4-hydroxyphenyl)-1-methylethylamino]ethoxyl}-3',5'-dimethylbiphenyl-4-carboxylic acid;

4'-{2-[(1R,2S)-2-hydroxy-2-(4-hydroxyphenyl)-1-methylethylamino]ethoxy}-3',5'-dimethyl-3-(p-tolyloxy)biphenyl-4-carboxylic acid;

3-(4-chlorophenoxy)-4'-{2-[(1R,2S)-2-hydroxy-2-(4-hydroxyphenyl)-1-methylethylamino]ethoxy}-3',5'-dimethyl-biphenyl-4-carboxylic acid;

3-(4-fluorophenoxy)-4'-{2-[(1R,2S)-2-hydroxy-2-(4-hydroxyphenyl)-1-methylethylamino]ethoxy}-3',5'-dimethyl-biphenyl-4-carboxylic acid;

4'-{2-[(1R,2S)-2-hydroxy-2-(4-hydroxyphenyl)-1-methylethylamino]ethoxy}-3-(4-methoxyphenoxy)-3',5'-dimethyl-biphenyl-4-carboxylic acid;

4'-{2-[(1R,2S)-2-hydroxy-2-(4-hydroxyphenyl)-1-methylethylamino]ethoxy}-3'-methyl-3-phenoxybiphenyl-4-carboxylic acid;

4'-{2-[(1R,2S)-2-hydroxy-2-(4-hydroxyphenyl)-1-methylethylamino]ethoxy}-3-(4-methoxyphenoxy)-3'-methylbiphenyl-4-carboxylic acid;

3'-fluoro-4'-{2-[(1R,2S)-2-hydroxy-2-(4-hydroxyphenyl)-1-methylethylamino]ethoxy}-3-(4-methoxyphenoxy)biphenyl-4-carboxylic acid;

3-(4-chlorophenoxy)-3'-fluoro-4'-{2-[(1R,2S)-2-hydroxy-2-(4-hydroxyphenyl)-1-methylethylamino]ethoxy}biphenyl-4-carboxylic acid;

4'-{2-[(1R,2S)-2-hydroxy-2-(4-hydroxyphenyl)-1-methylethylamino]ethoxy}-2'-methyl-3-phenoxybiphenyl-4-carboxylic acid;

3-(4-fluorophenoxy)-4'-{2-[(1R,2S)-2-hydroxy-2-(4-hydroxyphenyl)-1-methylethylamino]ethoxy}-2'-methyl-biphenyl-4-carboxylic acid;

4'-{2-[(1R,2S)-2-hydroxy-2-(4-hydroxyphenyl)-1-methylethylamino]ethoxy}-6-methoxy-2'-methylbiphenyl-3-carboxylic acid;

4'-{2-[(1R,2S)-2-hydroxy-2-(4-hydroxyphenyl)-1-methylethylamino]ethoxy}-6-methoxy-3',5'-dimethylbiphenyl-3-carboxylic acid;

6-chloro-4'-{2-[(1R,2S)-2-hydroxy-2-(4-hydroxyphenyl)-1-methylethylamino]ethoxy}-3',5'-dimethylbiphenyl-3-carboxylic acid;

6-chloro-4'-{2-[(1R,2S)-2-hydroxy-2-(4-hydroxyphenyl)-1-methylethylamino]ethoxy}-3'-methylbiphenyl-3-carboxylic acid;

2-ethyl-4'-{2-[(1R,2S)-2-hydroxy-2-(4-hydroxyphenyl)-1-methylethylamino]ethoxy}biphenyl-4-carboxylic acid;

4'-{2-[(1R,2S)-2-hydroxy-2-(4-hydroxyphenyl)-1-methylethylamino]ethoxy}-2-methylbiphenyl-4-carboxylic acid;

4'-{2-[(1R,2S)-2-hydroxy-2-(4-hydroxyphenyl)-1-methylethylamino]ethoxy}-2-isopropylbiphenyl-4-carboxylic acid;

4'-{2-[(1R,2S)-2-hydroxy-2-(4-hydroxyphenyl)-1-methylethylamino]ethoxy}-2-trifluoromethylbiphenyl-4-carboxylic acid;

4'-{2-[(1R,2S)-2-hydroxy-2-(4-hydroxyphenyl)-1-methylethylamino]ethoxy}-3-propylbiphenyl-4-carboxylic acid;

4'-{2-[(1R,2S)-2-hydroxy-2-(4-hydroxyphenyl)-1-methylethylamino]ethoxy}-2-propylbiphenyl-4-carboxylic acid;

3-sec-butyl-4'-{2-[(1R,2S)-2-hydroxy-2-(4-hydroxy-phenyl)-1-methylethylamino]ethoxy}biphenyl-4-carboxylic acid;

3-cyclopentyl-4'-{2-[(1R,2S)-2-hydroxy-2-(4-hydroxyphenyl)-1-methylethylamino]ethoxy}biphenyl-4-carboxylic acid;

4'-{2-[(1R,2S)-2-hydroxy-2-(4-hydroxyphenyl)-1-methylethylamino]ethoxy}-3-phenoxybiphenyl-4-carboxylic acid;

4'-{2-[(1R,2S)-2-hydroxy-2-(4-hydroxyphenyl)-1-methylethylamino]ethoxy}-3-methoxyphenoxy)biphenyl-4-carboxylic acid;

3-(4-chlorophenoxy)-4'-{2-[(1R,2S)-2-hydroxy-2-(4-hydroxyphenyl)-1-methylethylamino]ethoxy}biphenyl-4-carboxylic acid;

3-(4-fluorophenoxy)-4'-{2-[(1R,2S)-2-hydroxy-2-(4-hydroxyphenyl)-1-methylethylamino]ethoxy}biphenyl-4-carboxylic acid; and 4'-{2-[(1R,2S)-2-hydroxy-2-(4-hydroxyphenyl)-1-methylethylamino]ethoxy}-3-(p-tolyloxy)biphenyl-4-carboxylic acid.

14. A pharmaceutical composition which comprises, as an active ingredient, a compound according to claim 1 or a pharmaceutically acceptable salt thereof.

15. A therapeutic agent for obesity, diabetes mellitus, hyperlipidemia, pollakiurea, or urinary incontinence, which comprises, as an active ingredient, a compound according to claim 1 or a pharmaceutically acceptable salt thereof.

16. A pharmaceutical combination comprising a compound according to claim 1 or a pharmaceutically acceptable salt thereof and at least one selected from the group consisting of an antiobesity agent, an antidiabetic agent, a hypolipidemic agent and a therapeutic agent for urinary dysfunctions other than a β3-adrenoceptor agonist.

17. A method for treating obesity, diabetes mellitus, hyperlipidemia, pollakiurea or urinary incontinence which comprises administering an effective amount of a compound according to claim 1 or a pharmaceutically acceptable salt thereof.

18. A method of stimulating ⊖3-adrenoceptor in a mammal comprising administering an effective amount of compound according to claim 1 or a pharmaceutically acceptable salt thereof, wherein the said mammal suffers from obesity, diabetes mellitus, hyperlipidemia, pollakiurea, urinary incontinence, diseases caused by biliary calcus or biliary tract hypermotility, or diseases caused by intestinal hypermotility.

\* \* \* \* \*